United States Patent
Seeley et al.

(10) Patent No.: US 10,940,309 B2
(45) Date of Patent: Mar. 9, 2021

(54) TECHNIQUES FOR FORMING A MODULAR LEAD

(71) Applicant: Medtronic, Inc., Minneapolis, MN (US)

(72) Inventors: Dale F. Seeley, Spring Park, MN (US); Michael T. Hegland, Mounds View, MN (US)

(73) Assignee: Medtronic, Inc., Minneapolis, MN (US)

( * ) Notice: Subject to any disclaimer, the term of this patent is extended or adjusted under 35 U.S.C. 154(b) by 361 days.

(21) Appl. No.: 15/843,906

(22) Filed: Dec. 15, 2017

(65) Prior Publication Data

US 2018/0169404 A1 Jun. 21, 2018

Related U.S. Application Data

(60) Provisional application No. 62/435,618, filed on Dec. 16, 2016.

(51) Int. Cl.
*H01R 43/00* (2006.01)
*A61N 1/05* (2006.01)
(Continued)

(52) U.S. Cl.
CPC .......... *A61N 1/0534* (2013.01); *A61B 5/0408* (2013.01); *A61B 5/0478* (2013.01);
(Continued)

(58) Field of Classification Search
CPC .... A61B 2560/0214; A61B 2560/0443; A61B 2562/043; A61B 2562/125;
(Continued)

(56) References Cited

U.S. PATENT DOCUMENTS

| 7,326,083 B2 | 2/2008 | Mehdizadeh et al. |
| 8,171,621 B2 | 5/2012 | Swanson et al. |

(Continued)

FOREIGN PATENT DOCUMENTS

| WO | 2017/180827 A1 | 10/2017 |
| WO | 2017180827 A1 | 10/2017 |
| WO | 2017180831 A1 | 10/2017 |

OTHER PUBLICATIONS

Office Action from U.S. Appl. No. 15/843,941, dated Jun. 26, 2019, 11 pp.

(Continued)

*Primary Examiner* — Paul D Kim
(74) *Attorney, Agent, or Firm* — Shumaker & Sieffert, P.A.

(57) ABSTRACT

Systems, devices, and techniques are disclosed for forming an elongate lead body module of a modular lead. The method may comprise rotating a mandrel, wherein the mandrel extends through a through-hole of a conductor hub, wherein each conductor of a plurality of conductors extend through a respective channel of a plurality of channels of the conductor hub, wherein each conductor of the plurality of conductors extends from a respective bobbin of plurality of bobbins to the channels, wherein the plurality of bobbins are coupled to a carriage, the carriage defining a central opening through which the mandrel passes. The method may comprise moving the carriage away from the conductor hub along a length of the mandrel while the mandrel rotates causing the conductors to coil around the mandrel.

29 Claims, 29 Drawing Sheets

(51) Int. Cl.
*A61B 5/0408* (2006.01)
*A61B 5/0478* (2006.01)
*A61B 5/00* (2006.01)
*A61N 1/375* (2006.01)
*A61N 1/372* (2006.01)
*A61B 5/04* (2006.01)

(52) U.S. Cl.
CPC ............... *A61B 5/686* (2013.01); *A61N 1/05* (2013.01); *A61N 1/375* (2013.01); *A61N 1/37247* (2013.01); *A61B 5/0031* (2013.01); *A61B 5/04* (2013.01); *A61B 2560/0214* (2013.01); *A61B 2560/0443* (2013.01); *A61B 2562/043* (2013.01); *A61B 2562/125* (2013.01); *A61B 2562/182* (2013.01); *A61B 2562/222* (2013.01); *A61B 2562/227* (2013.01); *A61N 1/0551* (2013.01)

(58) Field of Classification Search
CPC ........ A61B 2562/182; A61B 2562/222; A61B 2562/227; A61B 5/0031; A61B 5/04; A61B 5/0478; A61B 5/0408; A61B 5/686; A61N 1/0534; A61N 1/0551; A61N 1/37247; A61N 1/375

See application file for complete search history.

(56) References Cited

U.S. PATENT DOCUMENTS

| | | | |
|---|---|---|---|
| 8,478,425 | B2 | 7/2013 | Klardie et al. |
| 8,634,936 | B2 | 1/2014 | Klardle et al. |
| 8,712,527 | B2 | 4/2014 | Seeley et al. |
| 8,792,995 | B2 | 7/2014 | Klardie et al. |
| 9,138,576 | B2 * | 9/2015 | Klardie ................ A61N 1/0534 |
| 9,550,056 | B2 | 1/2017 | Klardie et al. |
| 9,808,615 | B2 | 11/2017 | Klardie et al. |
| 2010/0057175 | A1 | 3/2010 | McDonald et al. |
| 2011/0072658 | A1 | 3/2011 | Dye et al. |
| 2011/0160815 | A1 * | 6/2011 | Brinkman ............. A61N 1/056 607/115 |
| 2011/0165785 | A1 | 7/2011 | Lindner et al. |
| 2014/0074214 | A1 * | 3/2014 | Raje ....................... A61N 1/05 607/137 |
| 2014/0213118 | A1 | 7/2014 | Glynn et al. |
| 2014/0316502 | A1 | 10/2014 | Seeley |
| 2015/0165217 | A1 | 6/2015 | Hughes |
| 2016/0287862 | A1 | 10/2016 | Shan et al. |

OTHER PUBLICATIONS

U.S. Appl. No. 15/843,941, filed by Dale F. Seeley et al., filed Dec. 15, 2017.
International Patent Application No. PCT/US2017/066724, filed by Medtronic, Inc. filed on Dec. 15, 2017.
Notice of Allowance from U.S. Appl. No. 15/843,941, dated Nov. 27, 2019, 5 pp.

* cited by examiner

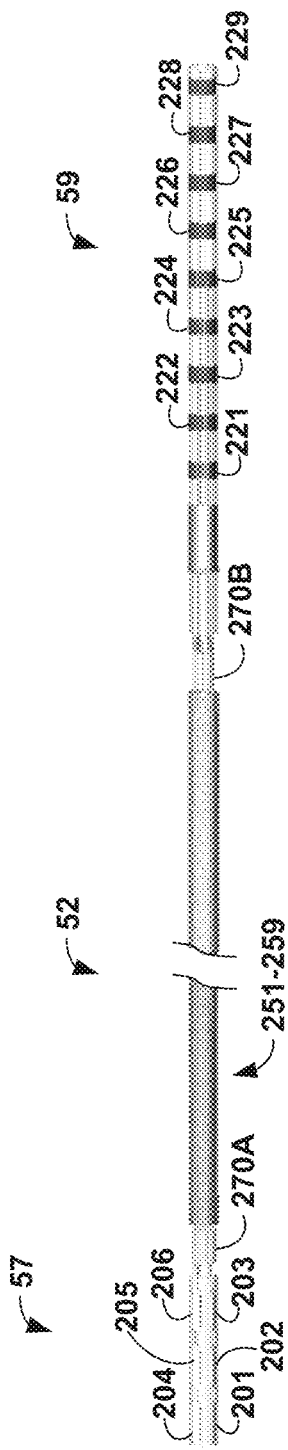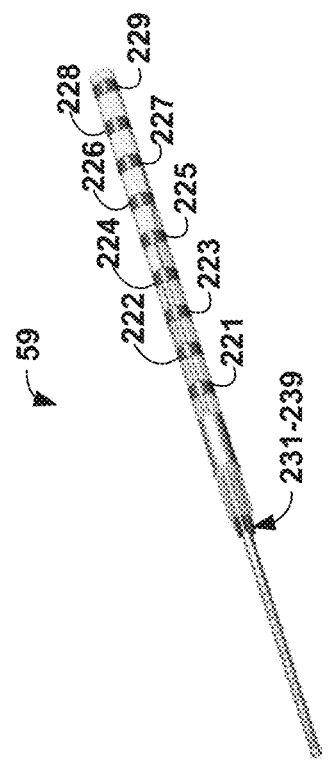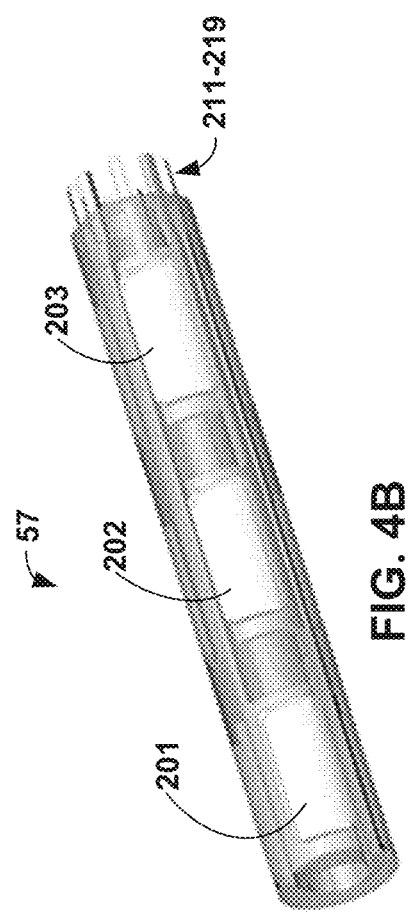
FIG. 4A
FIG. 4B
FIG. 4C

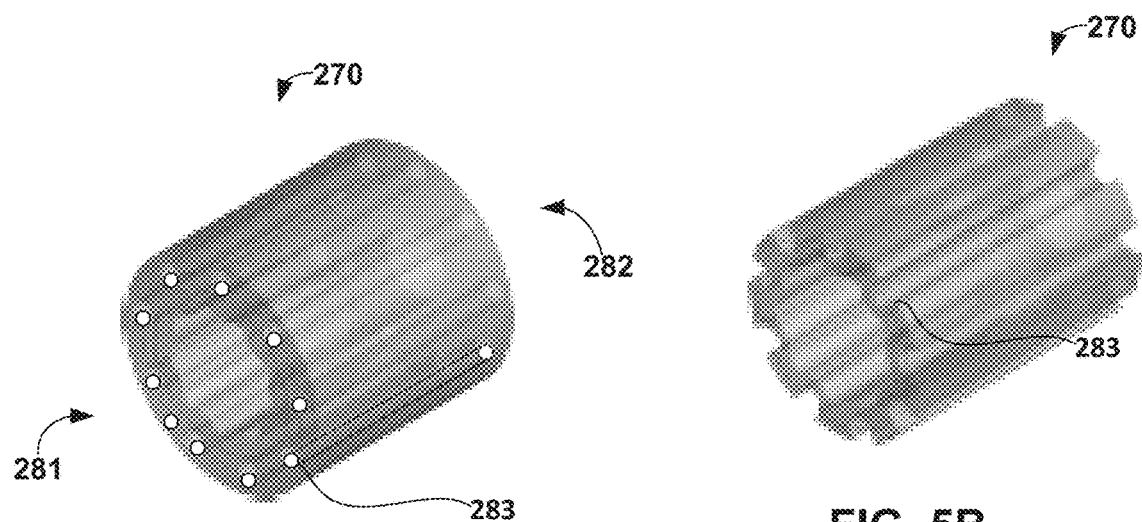
FIG. 5A
FIG. 5B
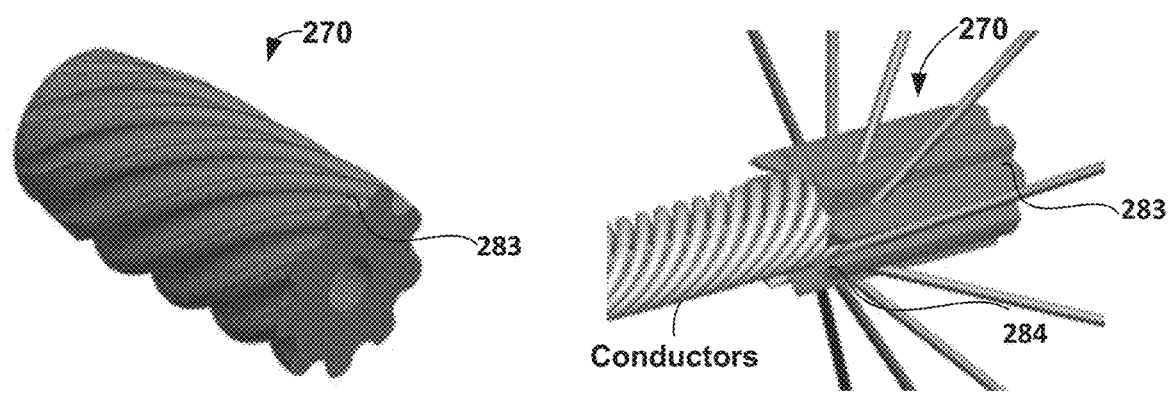
FIG. 5C
FIG. 5D

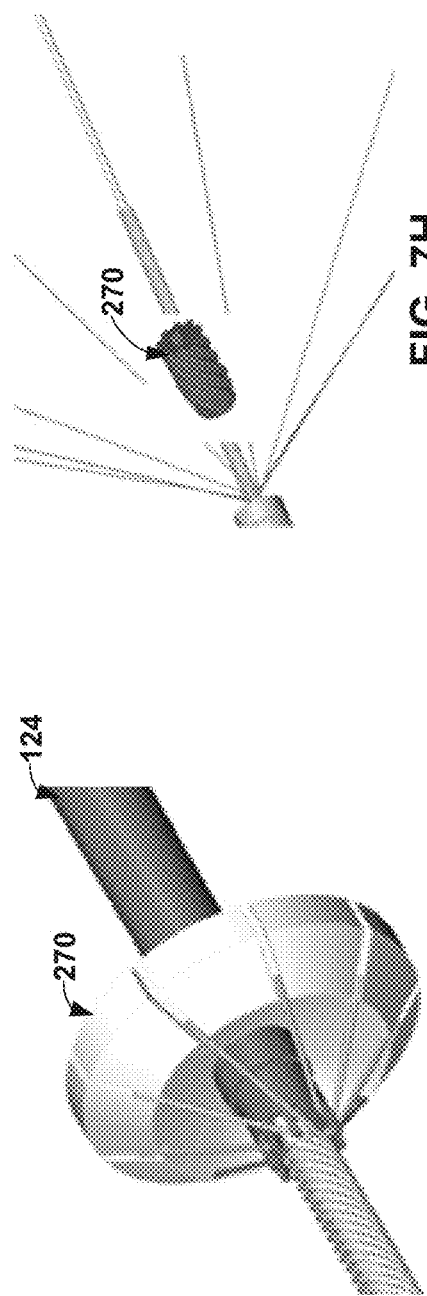
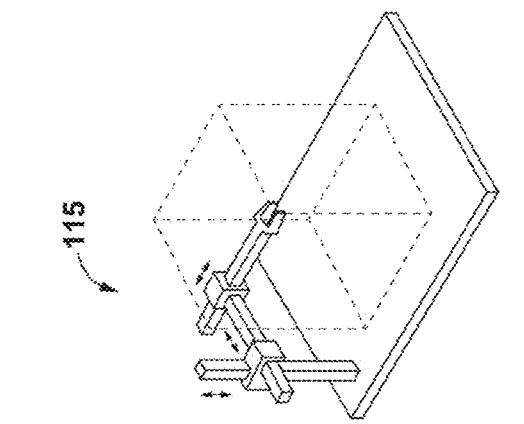
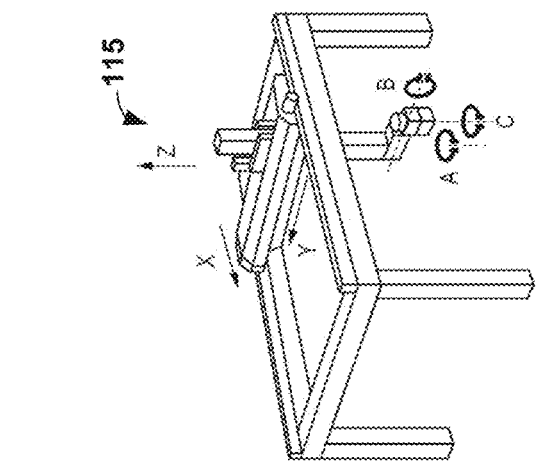
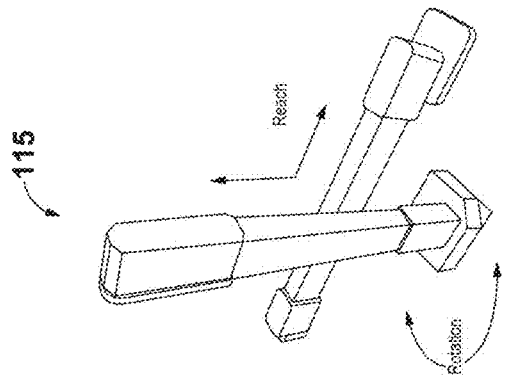

TECHNIQUES FOR FORMING A MODULAR LEAD

This application claims the benefit of U.S. Provisional Application Ser. No. 62/435,618, filed on Dec. 16, 2016, the entire content of which is incorporated herein by reference.

TECHNICAL FIELD

This disclosure relates to medical device systems including one or more leads.

BACKGROUND

Medical devices may be used to deliver therapy to a patient to treat symptoms or conditions such as chronic pain, seizure disorders (e.g., epilepsy), heart arrhythmias (e.g., fibrillation), tremor, Parkinson's disease, other types of movement disorders, obesity, mood disorders, urinary or fecal incontinence, or other types of symptoms or conditions. The therapy may be electrical stimulation therapy. Medical devices, such as implantable medical devices (IMDs), may be used for therapies such as deep brain stimulation (DBS), spinal cord stimulation (SCS), sacral neuromodulation, pelvic stimulation, gastric stimulation, peripheral nerve stimulation, cardiac stimulation, functional electrical stimulation, or other types of stimulation.

A medical device may include one or more leads carrying one or more electrodes. The medical device may deliver the electrical stimulation therapy to one or more target tissue sites within the patient and/or sense one or more electrical signals via the lead.

SUMMARY

In some examples, the disclosure describes devices and systems including modular medical leads, as well as techniques and systems for making and using such modular leads. Examples may include therapy systems (e.g., medical device systems) that employ a modular lead to deliver electrical stimulation therapy and/or sense electrical signals of the patient to treat a patient condition. A modular lead may include two or more distinct modules that may be manufactured independent of each other and subsequently joined to each other to form a lead as desired. When the respective modules are assembled to form a modular lead, the modular medical lead may be configured to be coupled to a medical device (e.g., an IMD) to deliver electrical stimulation to a tissue of a patient and/or sense electrical signals via one or more electrodes of the modular lead. The one or more electrodes may be electrically coupled to the medical device via one or more conductors extending distally within a lead body to the electrodes from one or more proximal electrical contacts.

In one example, a modular lead may include a lead body module including a plurality of conductors in a coiled configuration (also may be referred to as a coiled "arrangement") extending along a length of the lead. The plurality of conductors may be electrically isolated from each other in the lead body module to define a plurality of isolated conductive paths. The lead body module may also include a conductor hub (also may be referred to as a "distribution hub," a "starting hub" or a "hub") at one or more end portions of the lead body module. The conductor hub may be mechanically coupled to the plurality of coiled conductors to fix the ends of the conductors relative to each other in a desired arrangement (e.g., as opposed to being loose ends extending from a coiled portions). For example, each of the plurality of conductors may extend through a corresponding channel or other coupling feature of the hub located near an end of the lead body module along a desired path and position such that the distal ends of the respective conductors extend from the end of the hub in a desired direction with a desired spacing between the respective conductors.

In some examples, the arrangement of conductor ends extending from the hub may be selected such that the plurality of conductors may be aligned with corresponding conductive portions of another lead module to be coupled to the end of the lead body module, e.g., without an interconnector between the respective modules. Examples of such an additional lead module may include an electrode module or a connector module. In some examples, an electrode module includes a plurality of electrodes defining conductive surfaces configured to deliver electrical stimulation to a target site of the patient and/or sense electrical signal of the patient. The electrode module may be coupled to the lead body module via the plurality of conductors that run through the conductor hub in a configuration in which each of the respective conductors of the plurality of conductors of the lead body module are electrically coupled to a corresponding electrode of the electrode module. Likewise, for example, a connector module may include a plurality of electrical connectors configured to be coupled to a corresponding electrical connector of a medical device. The connector module may be coupled to the lead body module via the plurality of conductors that run through the conductor hub in a configuration in which each of the respective conductors of the plurality of conductors of the lead body module are electrically coupled to a corresponding electrical connector of the connector module. In some examples, a modular lead may include a connector module electrically connected to an electrode module via the elongate lead body module.

Additionally, examples of the disclosure relate to techniques and systems that may be used to manufacture an elongate lead body module. For example, during the manufacturing process, a plurality of conductors (e.g., each from a separate spool) may be first mechanically coupled to a conductor hub (referred to also as a starting hub) at a starting end and then the conductors may be wound about a mandrel using a winder to form a coiled portion of a desired length for the elongate lead body module. Once the wound coil section is complete, another conductor hub may be used to fix the conductors at the finishing end of the newly coiled conductors from the winder. In some examples, a stabilizer hub may be utilized in a multi-step process in which the conductors are initially mated with the stabilizer hub, which controls the unwinding of the coiled conductors (e.g., in terms of speed, amount, etc.) during manufacturing spring back of the coil and keeps the conductors in a desired arrangement. Subsequently, the conductors may be transferred from the stabilizer hub to a final distribution hub in the arrangement defined by the stabilizer hub.

In one aspect, the disclosure is directed to a modular medical lead system comprising an elongate lead body module including a plurality of coiled electrical conductors extending from a first end to a second end of the elongate lead body module, and a conductor hub adjacent the first end of the elongate lead body module. In some examples, one or more conductors (e.g., the plurality of conductors) may be in a straight arrangement or a sinusoidal arrangement. The plurality of conductors may be electrically isolated from one another and mechanically coupled to the conductor hub such that the plurality of conductors may be in a fixed arrangement relative one another. A first end of the conductor hub may be nearer the first end of the elongate lead body module than a second end of the conductor hub. Each of the plurality of conductors may extend from the first end to the second end of the conductor hub relative a longitudinal axis of the elongate lead body module such that a portion of the conductors extend beyond the first end of the conductor hub. For each conductor, the portion of the conductor that extends beyond the first end of the conductor hub is configured to be coupled to a respective electrical conductor of a lead end module to allow respective electrical signals to be conducted between the respective conductors of the lead end module and the conductors of the elongate lead body module.

In another aspect, the disclosure is directed to medical device system comprising a modular medical lead system described herein and a medical device. The medical device may be configured to at least one of deliver electrical stimulation to a patient or sense electrical signal of the patient via the plurality of conductors.

In another aspect, the disclosure is directed to a method may comprise at least one of delivering electrical stimulation to a patient or sensing electrical signals of the patient via a medical device system described herein.

In another aspect, the disclosure is directed to a method comprising forming a modular lead system described herein, wherein forming the modular lead system includes coiling or arranging the plurality of electrical conductors; and mechanically coupling the plurality of electrical conductors to the conductor hub such that the plurality of conductors are in a fixed arrangement relative one another.

In another aspect, the disclosure is directed to a conductor hub for a modular medical lead system comprising a hub body including a through-hole extending from a first end of the hub body to a second end of the hub body. The conductor hub may include a plurality of channels positioned around the conductor hub. Respective longitudinal axes of the plurality of channels may be substantially parallel to a longitudinal axis of the conductor hub. The plurality of channels may be positioned at a common radius from the longitudinal axis of the conductor hub.

In another aspect, the disclosure is directed to a method for forming an elongate lead body module of a modular lead, the method comprising rotating a mandrel. The mandrel may extend through a through-hole of a conductor hub, wherein a plurality of conductors may extend through a respective plurality of channels of the conductor hub, the conductors may extend from a respective plurality of bobbins to the channels, wherein the bobbins may be coupled to a carriage, the carriage may define a central opening through which the mandrel passes. The method may include moving the carriage away from the conductor hub along a length of the mandrel while the mandrel rotates causing the conductors to coil around the mandrel.

In another aspect, the disclosure is directed to a method for forming a modular lead comprising coiling a plurality of electrical conductors around a mandrel, wherein the mandrel may be coupled to a conductor hub, wherein the conductors may be mechanically coupled to the conductor hub such that the plurality of conductors may be in a fixed arrangement relative to one another. Coiling the conductors may include coiling the conductors along a length of the mandrel, wherein the plurality of conductors extend may from a respective plurality of bobbins coupled to a carriage, the carriage may define a central opening through which the mandrel extends. Coiling the conductors may include moving at least one of the mandrel and the carriage relative to each other angularly and longitudinally, wherein the relative longitudinal movement may occur along a longitudinal axis of the mandrel, and wherein the relative angular movement may occur such that an orientation of the mandrel and an orientation of the carriage rotate relative to each other.

In another aspect, the disclosure is directed to a system for assembling a modular medical lead, the system comprising a winder station including a mandrel extending from a first section to a second section of the winder station, a motor coupled to the mandrel in the first section, a carriage mount configured to couple to a carriage, wherein the mandrel extends through an opening defined by the carriage, and wherein the carriage mount is configured to move along in a direction of a longitudinal axis of the mandrel.

The details of one or more aspects of the disclosure are set forth in the accompanying drawings and the description below. Other features, objects, and advantages will be apparent from the description and drawings, and from the claims.

BRIEF DESCRIPTION OF DRAWINGS

FIGS. 4A-4F are conceptual diagrams illustrating an example components of a modular medical lead.

FIGS. 7A-7K illustrate examples of a modular medical lead system and an assembly system therefor.

DETAILED DESCRIPTION

Figure 1:
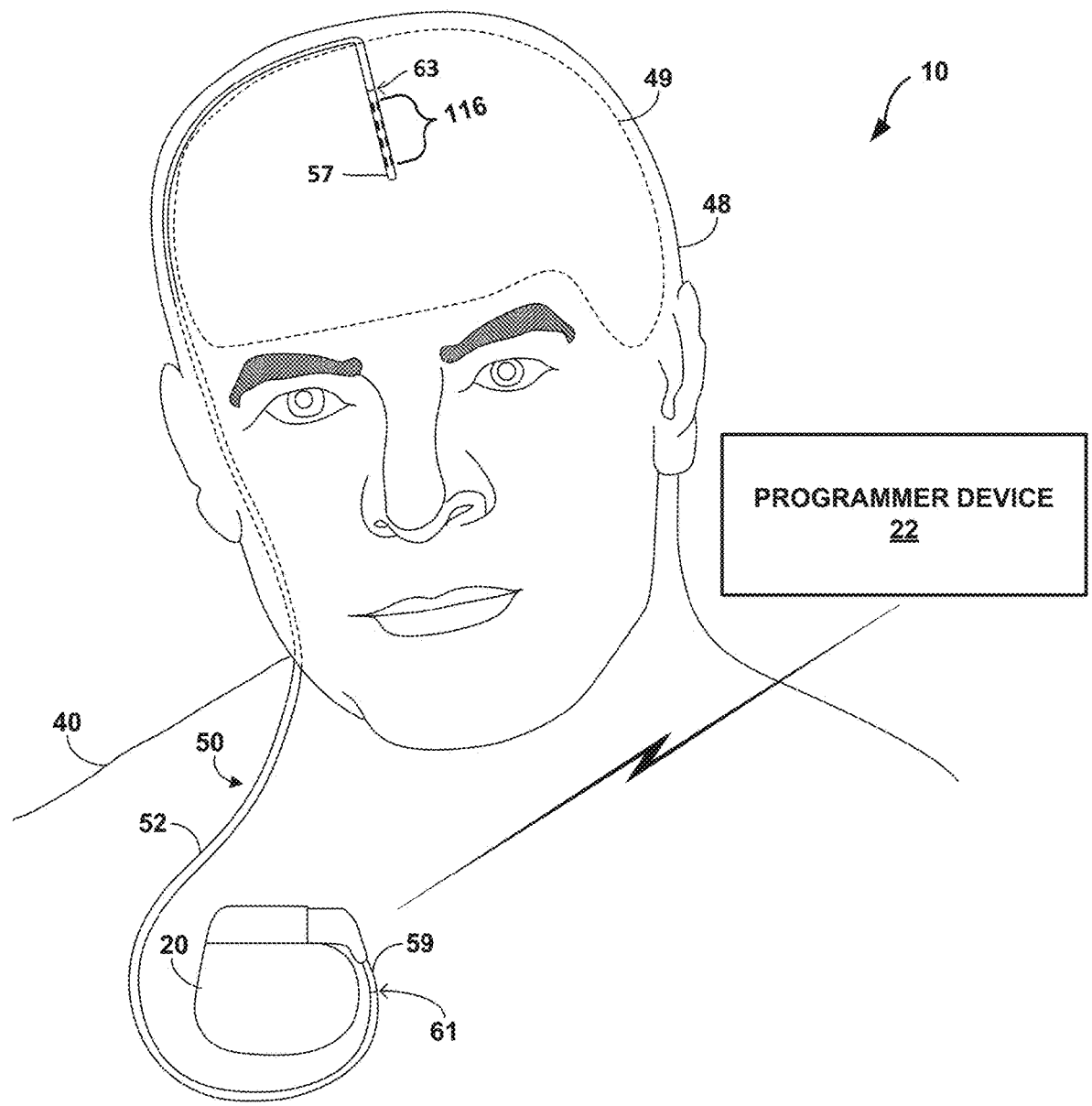
FIG. 1 is a conceptual diagram illustrating an example of a therapy system that delivers electrical stimulation therapy to a patient.

As described above, some examples of the disclosure relate to medical device leads (also referred to as "lead systems," "medical leads," or "leads") including one or more electrodes. Using the lead and electrode, a medical device may deliver or sense electrical signals to provide therapy to a patient to treat a patient condition. Medical leads may include a conductive electrode member electrically and mechanically connected to one or more conductive lead wires (also may be referred to as "conductors") extending through the lead body. Electrical stimulation from a medical device may be conductive along the lead wire to be delivered across the electrode surface.

In some examples, a medical device system includes a medical device, such as an ambulatory medical device (AMD) or an implantable medical device (IMD). The medical device system may include lead system, such as a modular medical lead system. In an example, the modular medical lead system includes an elongate lead body module, which may include a section having conductors in a coiled arrangement and one or more conductor hubs. In some examples, the elongate lead body module includes one or more conductor hubs, such as in the finished product to be implanted in a patient. The conductor hub may be used as a starting hub or a conductor distribution hub during the manufacture of the lead system. In some examples, the conductor hub may be used for starting the manufacture of the elongate lead body module, and in other examples may be used for finishing the manufacture of the elongate lead body module, such as once the conductors are in a coiled arrangement or another arrangement along a length of the elongate lead body module. In some examples, an arrangement of the conductors may not be maintained without the help of a device or other assistance. In one example, the conductor hub helps to maintain the arrangement of the conductors during and after manufacture of the elongate lead body module.

The modular medical lead system may include one or more lead end modules. In one example, the lead end module is an electrode module with an electrode arrangement configured to treat the patient condition or to sense the electrical signal. In another example, the lead end module is a connector module, such as may be configured to connect to the medical device. The connector module may have a plurality of electrical contacts, such as corresponding to the plurality of conductors in the elongate lead body module, where the electrical contacts couple to respective contacts of the medical device or a conductor (lead) extension which in turn coupled to a medical device. In some examples, the modular medical lead system includes a jacket module. The jacket module may be electrically insulated or biocompatible. The jacket module may cover the conductor hub. In some examples, the jacket module is over molded on the coiled arrangement of conductors.

The modular medical lead system may comprise two or more modules. In one example, the modular medical lead system includes the electrode module coupled to the elongate lead body module on a first end of the elongate lead body module, and the connector module coupled to a second end of the elongate lead body module. In another example, a lead body module may be coupled to an electrode module at a first end and the second end of the lead body module may include electrical contacts configured to couple the lead body module to the electronics of an IMD or other medical device, e.g., as opposed to a separate connector module being joined to the lead body module. In another example, a lead body module may be coupled to a contact module at a first end and the second end of the lead body module may include one or more electrodes configured to deliver electrical stimulation and/or sense electrical signals, e.g., as opposed to a separate electrode module being joined to the lead body module. In another example, the modular medical lead system includes two or more elongate lead body modules coupled directly to each other. In an example, a first elongate lead body module is coupled to the electrode module on a first end of the electrode module, and a second elongate lead body module is coupled to the electrode module on a second end of the electrode module. Other types of modules may be used in the modular medical lead system, such as may include a conductor extension module that may provide additional length to the lead, a sensor module that may be configured to sense a particular physiological parameter, a delivery module that may be configured to provide a therapeutic effect other than electrical stimulation, such as physically or mechanically. Other types of modules may be used for various purposes, and the modular medical lead system may include combinations or one or more types of modules.

Some aspects of the disclosure relate to a process including winding one or more conductors for the elongate lead body module to form a coiled arrangement of conductors between a first end and a second end of the elongate lead body module. The one or more conductors may be electrically conductive wires for use in the medical device system. In some examples, the conductors are electrically insulated from one another, such as may include using an insulated layer or coating. In some examples, the conductor may include a single strand, such as a "filar," a "wire," or another single strand that is electrically conductive. In other examples, the conductor may comprise a coil. The coil may include multiple conductive strands coiled or wound together, as by a mandrel. The one or more coiled conductors may have a diameter smaller than the overall coiled arrangement, such that the coiled arrangement of the elongate lead body module may comprise one or more smaller coils. In other examples, the conductor may refer to a cable. The cable may include multiple conductive wires, filars, other conductors, or a combination thereof, twisted, wrapped, or otherwise grouped together, such as to form a conductor. In some examples, a cable may include a bundle of strands of wire, such as may be referred to as a "BSW." In some examples, a coiled structure that is formed of the one or more cables may be referred to as a "coible."

In an example, a portion of the ends of individual conductors may extend beyond a conductor hub. The portion of the conductor that extends beyond the conductor hub may be used to couple the elongate lead body module to a lead end module. For example, the portion may be coupled to the lead end module. In another example, the portion may be coupled to a respective portion of a conductor extending from the lead end module. In some examples, coupling multiple modules includes welding, such as laser welding. Any other type of mechanism for coupling these modules may be used in addition to, or instead of, welding including, without limitation, conductive glue, crimping, or swaging. As such, the portion may be welded to the lead end module itself, or to the respective portion of the conductor extending from the lead end module.

In some examples, the elongate lead body module includes an arrangement of conductors between the first and the second ends of the elongate lead body module. In an example, the arrangement is a coiled arrangement, such that multiple conductors are wound around a longitudinal axis of the elongate lead body module. In another example, the arrangement includes a straight arrangement, such that one or more conductors are substantially straight relative to the longitudinal axis of the elongate lead body module. The conductors may be coupled to the conductor hub. And, in some examples, the conductors form a straight arrangement within channels of the conductor hub. In some examples, the portion of the conductor that extends beyond the conductor hub is in a straight arrangement, such as may be used to couple the elongate lead body module to another module.

As described herein, the conductors may be in the coiled arrangement up to the conductor hub, and then past the conductor hub, the portion of the conductors such as extending out of the channels of the conductor hub may be in the straight arrangement. In this way, the elongate lead body module may include a "coiled to straight" arrangement of the conductors. In another example, the plurality of conductors of the elongate lead body module includes a "straight to coiled to straight" arrangement. In some examples, the portion of the conductors extending out of the channels are in an angled arrangement, such as relative to the longitudinal axis of the elongate lead body module. In some examples, the portion of the conductors extending out of the channels are in a helical or coiled arrangement. In some examples, the portion of the conductors extending out of the channels define a diameter larger than a diameter of the coiled arrangement of the elongate lead body module. And in other examples, the portion of the conductors extending out of the channels define a diameter smaller than the diameter of the coiled arrangement of the elongate lead body module. The arrangement of the plurality of conductors at the first and second ends of the elongate lead body module may be sized or shaped to a desired arrangement, such as for coupling to another module.

The modular medical lead system may be manufactured using an assembly system. In some examples, the assembly system includes an assembly apparatus and a winder apparatus. The assembly apparatus may include a base, and a carriage may be placed on the base. In some examples, the carriage includes a plurality of bobbins. A plurality of conductors may be wound around the respective plurality of bobbins, such that each conductor may correspond to a particular bobbin. The bobbins may be coupled to the carriage, such as by being placed on a pin of the carriage. The carriage may comprise a circular shape, and the bobbins may be distributed in a circular shape including, for example, a smaller diameter than a diameter of the carriage. Using the assembly apparatus, for example, the conductors may be coupled to the conductor hub. In one example, each of the plurality of conductors is threaded into a respective channel of the conductor hub. In an example, the plurality of conductors are coupled to the respective plurality of channels of the conductor hub automatically, such as by using a robotic arm or a Cartesian gantry robotic arm, and computer vision.

In some examples, the winder apparatus includes a mandrel extending from a first section to a second section of the winder apparatus. The winder apparatus may include a motor coupled to the mandrel in the first section. The winder apparatus may include a carriage mount configured to couple to the carriage. The mandrel may extend through an opening defined by the carriage. The carriage mount may be configured to move along in a direction of a longitudinal axis of the mandrel.

In an example, when the carriage is coupled to the carriage mount on the winder apparatus, the conductor hub may be coupled to the mandrel such that when the motor is activated, the mandrel and the conductor hub rotate together. In an example, the coiled arrangement of the conductors of the elongate lead body module is formed by rotating the mandrel while the carriage mount moves away from the conductor hub, along a length of the mandrel. As such, the conductors may unwind from the bobbins as the conductors are wound around the mandrel, and a plurality of corresponding brakes coupled to the bobbins may control the angular speed of the bobbins, or the tensions of the conductors or the torque of the conductors.

In an example, modular lead construction may include discrete lead end modules that are connectable to an elongate lead body module. Modular architecture may provide agile product development and may improve manufacturability while increasing the features and performance known with legacy or conventional architectures. By using the modular medical lead system, such as described in this disclosure, a joint may be formed where two modules are connected, such as by including a desired presentation of conductors at one or more ends of the elongate lead body module, such as by using the conductor hub. The features described herein may be used with leads having diameters under 0.060 inches, for example. In some examples, the diameters may be 0.050 inches or less. In one example, such as for a lead including 16 conductors, a diameter may be about 0.060 inches or more. In other examples, medical devices manufactured using features described herein may have much larger diameters extending to 0.5 inches or more, such as when used in screening or diagnostic cable applications that are not intended for implantation. In some examples the construction of the medical lead system may not depend on operator skill.

In one example, the subject matter herein includes a modular lead system including eight or more conductors, and including a diameter of about 0.060 inches or less. The diameter will scale as more conductors are included in the system. For instance, a system having thirty or more conductors (e.g., thirty-two conductors) may have a diameter of 0.150 inches or greater. A conductor hub may be used as a starting hub to locate and fix the conductors into a desired presentation or arrangement. A method may include using with discrete lengths of conductors (e.g., conductive wires), such as may be preterminated as needed, on bobbins to facilitate lead assembly. The bobbins and the starting hub may be set-up on an assembly carriage. In an example, the carriage may be transferred to a wire insertion station (such as a winder apparatus) that utilizes mechanized fixtures or robotics to insert the wires into the guides. The carriage may then be transferred to a winding machine where the guide is driven to create the coiled arrangement of the elongate lead body module. A coil-to-straight wire presentation may be provided using the features and techniques herein. In an example, the other end can also be terminated with a guide (e.g., a second conductor hub) using similar fixtures insert the conductors and create wire termination presentations to connect both distal and proximal lead end modules. In some examples, one or more conductor hubs may be formed on the lead body during the winding process (e.g., while coiling conductors on the unfinished elongate lead body module on the winding apparatus). For example, a sleeve, such as a polyurethane sleeve, may be positioned over an area of the elongate lead body module where a hub is desired, and the sleeve may be heated, resulting in a molded hub (e.g., using a reflow process).

In an example the manufacturing process may include termination of conductors for a coil, such as may be located and controlled in a desired presentation before the winding of the coil begins. In some examples interfacing the yet-to-be-formed elongate lead body module with a winder apparatus is provided. In one example, coupling two modules in a side-by-side or over-under presentation for a weld joint is described herein.

As will be apparent from the disclosure, examples of the disclosure may provide one or more advantages. In some examples, by manufacturing a module lead according to some examples described herein, manufacturing costs for a lead may be reduced, or manufacturing efficiency or yield may be increased. In an example, the elongate lead body module may first be manufactured without electrodes and/or connectors for connection to an IMD. Subsequently, the lead body module may be coupled to one or more lead end modules, such as, e.g., an electrode module having a desired arrangement of electrodes selected from several different electrodes modules and/or a connector module have a desired arrangement of connectors selected from several different connector modules. Alternatively, the elongate lead body module may be used to form a lead extension, with a distal end being coupled to a connector for connection to a proximal end of a lead module, and a proximal end being coupled to a connector for connection to an IMD. As another example, the body module may be coupled to any other type of end modules to manufacture a modular device having an elongate body with one or more conductors that have one or more ends that transition into a fixed format, with each end coupling to a respective end module. In some cases, the resulting medical system may be a monitoring device intended for acute monitoring or diagnostic purposes rather than for chronic implantation in the body. In other cases, the system may comprise a screening device that delivers therapy acutely to determine efficacy (e.g., as priority implantation). Thus, methods, devices, structures, and system described herein may relate to any type of acute or chronic medical devices, including medical electrical or other leads, lead extensions, trialing devices, screening systems, diagnostic devices, monitoring devices, or any other systems comprising elongate bodies with one or more conductors that transition at one or more ends to predetermined configurations for attachment in a module manner to end modules. In some examples, these techniques may be applied to non-medical applications, such as manufacturing cables for the various purposes for electronics industry.

In this manner, each elongate body module may be coupled to any number of differently configured end connector modules and/or electrode modules, as compared to a non-modular lead in which the end connector and electrode configuration at the ends of the lead body. In some examples, the conductor hub of a lead body module may fix the arrangement of the conductors end in a manner that matches the arrangement of conductors of an electrode module and/or connector module. In this manner, the conductors of the lead body module may be directly joined to the corresponding conductors of the electrode module and/or connector module, e.g., with the use of a separate interconnector member.

In an example, the techniques to manufacture the modular medical lead system described in this disclosure may increase the reliability of the manufacturing process, such as may include providing more uniform end products. In an example, the features and techniques described in this disclosure may reduce the need to dispose of a non-usable portion of a coiled arrangement of a lead made using conventional techniques. In an example, by using the modular medical lead system described herein, a desired number of individual conductors may be used, such as, e.g., from eight to sixteen conductors, from two to four conductors, or from thirty-two to forty conductors. In other examples, even more conductors may be used, e.g., thirty-two or more conductors. In some examples, the techniques described in this disclosure may provide the ability to manufacture elongate lead body modules of a desired length, which may be subsequently joined with a connector module and/or electrode module as desired. In some examples, the elongate lead body module may include a coiled to straight arrangement for the conductors, where the conductors are in a coiled arrangement directly past one end of the conductor hub and in a straight arrangement past a second end of the conductor hub. The conductor hub may allow for a relatively short transition length form the coiled to straight arrangement of the conductors.

In some examples, modules of the modular architecture may be utilized with a variety of different lead designs (e.g., electrode modules and/or connector modules) without the need to repeat the regulatory process needed for approval of an entire non-modular lead assembly. This may allow quicker and less costly development cycles.

In some examples, the modular architecture may provide ease of manufacturability and lowering cost of goods. For example, the techniques and features herein may not rely on the skill of a human operator, e.g., in coiling or other manufacturing a medical lead by hand.

Quality, precision, consistency, and manufacturing efficiency may be obtained by use of automated or mechanized assembly rather than a human operator, or other features and techniques described herein.

FIG. 1 is a conceptual diagram illustrating an exemplary therapy system 10 including modular lead 50 implanted in the brain 49 of patient 40. For ease of illustration, examples of the disclosure will primarily be described with regard to implantable electrical stimulation leads and implantable medical devices that neurostimulation therapy to a patient's brain in the form of deep brain stimulation (DBS). However, the features and techniques described herein may be useful in other types of medical device systems which employ medical leads to deliver electricals stimulation to a patient and/or sense electrical signals via one or more electrodes of the lead. For example, the features and techniques described herein may be used in systems with medical devices that deliver stimulation therapy to a patient's heart, e.g., pacemakers, and pacemaker-cardioverter-defibrillators. As other examples, the features and techniques described herein may be embodied in systems that deliver other types of neurostimulation therapy (e.g., spinal cord stimulation or vagal stimulation), stimulation of at least one muscle or muscle groups, stimulation of at least one organ such as gastric system stimulation, stimulation concomitant to gene therapy, and, in general, stimulation of any tissue of a patient. The modular medical lead system may be used with human subjects or with non-human subjects.

As shown in FIG. 1, therapy system 10 includes medical device programmer 22, IMD 20, and modular lead 50. Modular lead 50 includes plurality of electrodes 116. IMD 20 includes a stimulation therapy module that includes an electrical stimulation generator that generates and delivers electrical stimulation therapy to one or more regions of brain 49 of patient 40 via one or more of electrodes 116. In the example shown in FIG. 1, therapy system 10 may be referred to as a DBS system because IMD 20 provides electrical stimulation therapy directly to tissue within brain 49, e.g., a tissue site under the dura mater of brain 49. In other examples, leads 50 may be positioned to deliver therapy to a surface of brain 49 (e.g., the cortical surface of brain 49).

In accordance with examples of the disclosure, modular lead 50 includes connector module 59, lead body module 52, and electrode module 57. Connector module 59 is coupled to one end of lead body module 52 at joint 61 and electrode module 57 is coupled to the other end of the lead body module at joint 63. As modular lead 50 is assembled, respective electrical connectors of connector module provide an electrical connection between IMD 20 and the conductive pathways of modular lead running to electrodes 16 of electrode module 57 defined by the plurality of conductors of lead body module 52. Using the conductive pathways, IMD 20 may deliver electrical stimulation to patient 40 and/or sense electric signals of patient 40 using modular lead 50.

In the example shown in FIG. 1, IMD 20 may be implanted within a subcutaneous pocket above the clavicle of patient 40. In other examples, IMD 20 may be implanted within other regions of patient 40, such as a subcutaneous pocket in the abdomen or buttocks of patient 40 or proximate the cranium of patient 40. Connector module 59 of modular lead 50 is coupled to IMD 20 via a connector block (also referred to as a header), which may include, for example, electrical contacts that electrically couple to respective electrical contacts on connector module 59 of lead 50. The electrical contacts electrically couple the electrodes 116 carried by electrode module 57 of lead 50. Lead 50 traverses from the implant site of IMD 20 within a chest cavity of patient 40, along the neck of patient 40 and through the cranium of patient 40 to access brain 49. Generally, IMD 20 is constructed of a biocompatible material that resists corrosion and degradation from bodily fluids. IMD 20 may comprise a hermetic housing to substantially enclose components, such as a processor, therapy module, and memory.

Lead 50 may be positioned to deliver electrical stimulation to one or more target tissue sites within brain 49 to manage patient symptoms associated with a disorder of patient 40. Lead 50 may be implanted to position electrodes 116 at desired locations of brain 49 through respective holes in cranium 48. Lead 50 may be placed at any location within brain 49 such that electrodes 116 are capable of providing electrical stimulation to target tissue sites within brain 49 during treatment. Although FIG. 1 illustrates system 10 as including a single lead 50 coupled to IMD 20, in some examples, system 10 may include more than one lead.

Lead 50 may deliver electrical stimulation via electrodes 116 to treat any number of neurological disorders or diseases in addition to movement disorders, such as seizure disorders or psychiatric disorders. Lead 50 may be implanted within a desired location of brain 49 via any suitable technique, such as through respective burr holes in a skull of patient 12 or through a common burr hole in the cranium 48. Lead 50 may be placed at any location within brain 49 such that electrodes 116 of lead 50 are capable of providing electrical stimulation to targeted tissue during treatment. In the examples shown in FIG. 1, electrodes 116 of lead 50 are shown as segmented electrodes. In other examples, electrodes 116 of lead 50 may have different configurations including ring or paddle electrodes. Electrodes 116 of lead 50 may have a complex electrode array geometry that is capable of producing shaped electrical fields. In this manner, electrical stimulation may be directed to a specific direction from lead 50 to enhance therapy efficacy and reduce possible adverse side effects from stimulating a large volume of tissue.

IMD 20 may deliver electrical stimulation therapy to brain 49 of patient 40 according to one or more stimulation therapy programs. A therapy program may define one or more electrical stimulation parameter values for therapy generated and delivered from IMD 20 to brain 49 of patient 40. Where IMD 20 delivers electrical stimulation in the form of electrical pulses, for example, the stimulation therapy may be characterized by selected pulse parameters, such as pulse amplitude, pulse rate, and pulse width. In addition, if different electrodes are available for delivery of stimulation, the therapy may be further characterized by different electrode combinations, which can include selected electrodes and their respective polarities. The exact therapy parameter values of the stimulation therapy that helps manage or treat a patient disorder may be specific for the particular target stimulation site (e.g., the region of the brain) involved as well as the particular patient and patient condition.

In addition to delivering therapy to manage a disorder of patient 40, therapy system 10 monitors electrical signals, such as, e.g., one or more bioelectrical brain signals of patient 40. For example, IMD 20 may include a sensing module that senses bioelectrical brain signals within one or more regions of brain 49. In the example shown in FIG. 1, the signals generated by electrodes 116 are conducted to the sensing module within IMD 20 via conductors within lead 50, including one or more conductors within lead body module 52 between electrode module 57 and connector module 59.

External programmer 22 wirelessly communicates with IMD 20 as needed to provide or retrieve therapy information. Programmer 22 is an external computing device that the user, e.g., the clinician and/or patient 40, may use to communicate with IMD 20. For example, programmer 22 may be a clinician programmer that the clinician uses to communicate with IMD 20 and program one or more therapy programs for IMD 20.

Alternatively, programmer 22 may be a patient programmer that allows patient 40 to select programs and/or view and modify therapy parameters. The clinician programmer may include more programming features than the patient programmer. In other words, more complex or sensitive tasks may only be allowed by the clinician programmer to prevent an untrained patient from making undesired changes to IMD 20.

Programmer 22 may be a hand-held computing device with a display viewable by the user and an interface for providing input to programmer 22 (i.e., a user input mechanism). In other examples, programmer 22 may be a larger workstation or a separate application within another multi-function device, rather than a dedicated computing device. For example, the multi-function device may be a notebook computer, tablet computer, workstation, cellular phone, personal digital assistant, or another computing device that may run an application that enables the computing device to operate as a secure medical device programmer 22.

As noted above, lead 50 may include electrode module 57 including a complex electrode array geometry, but may also include one or more single ring electrodes along the longitudinal axis in other examples. In one example, electrode module 57 includes a plurality of electrodes positioned at different axial positions along the longitudinal axis of the lead and a plurality of electrodes positioned at different angular positions around the circumference of the lead (which may be referred to as electrode segments). In this manner, electrodes may be selected along the longitudinal axis of lead 50 and along the circumference of the lead. Selectively activating electrodes of lead 50 can produce customizable stimulation fields that may be directed to a particular side of lead 50 in order to isolate the stimulation field around the target anatomical region of brain 49.

Again, while lead 50 is described here for use in DBS applications, lead 50 or other leads may be implanted at any other location within patient 40. For example, lead 50 may be implanted near the spinal cord, pudendal nerve, sacral nerve, or any other nervous or muscle tissue that may be stimulated. The user interface described herein may be used to program the stimulation parameters of any type of stimulation therapy. In the case of pelvic nerves, defining a stimulation field may allow the clinician to stimulate multiple desired nerves without placing multiple leads deep into patient 40 and adjacent to sensitive nerve tissue. Therapy may also be changed if leads migrate to new locations within the tissue or patient 40 no longer perceives therapeutic effects of the stimulation. The features or techniques of this disclosure may be useful in other types of medical applications.

Figure 3:
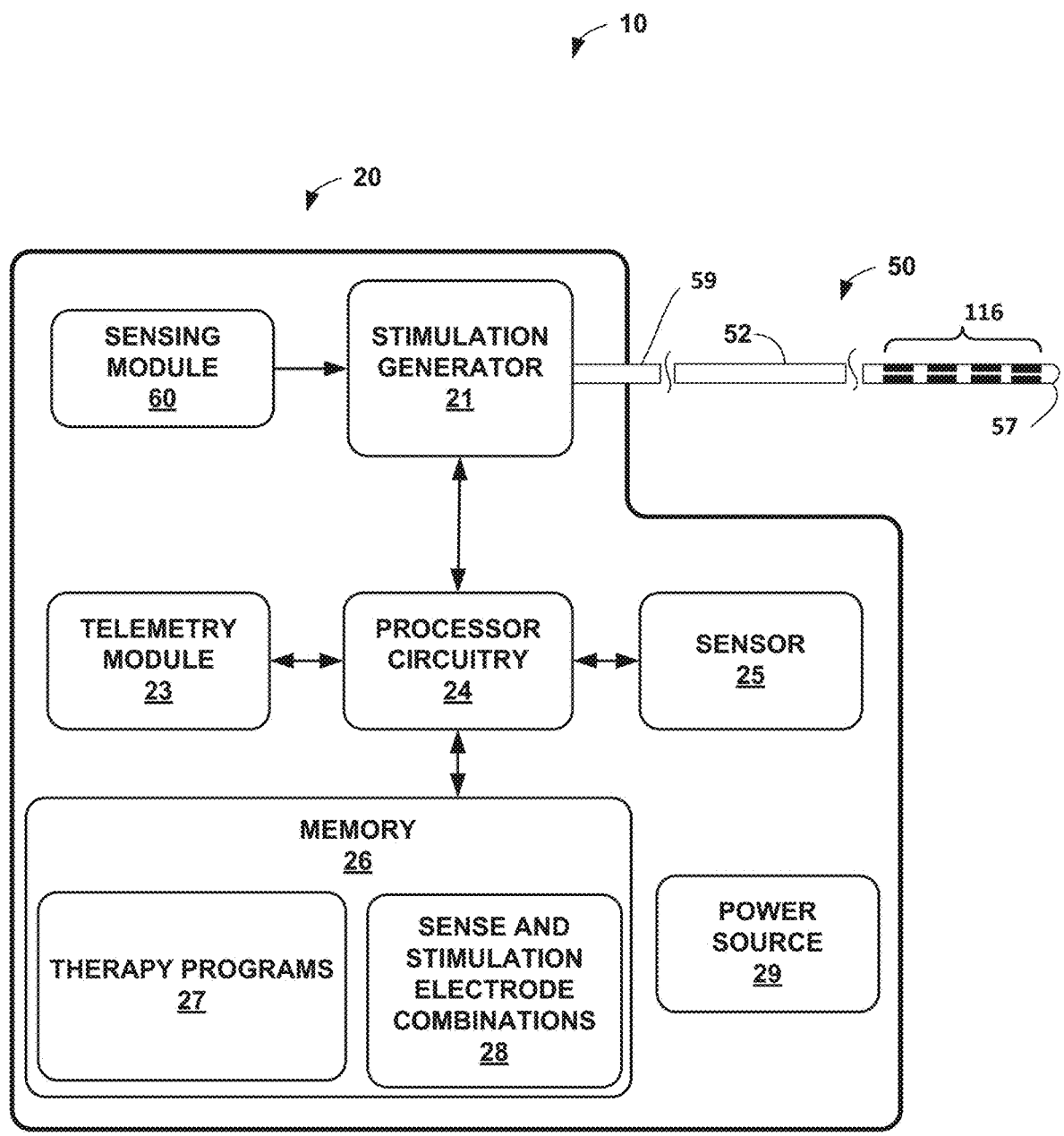
FIG. 3 is a functional block diagram illustrating components of an implantable medical device.

FIG. 3 is a functional block diagram illustrating components of IMD 20. As shown, medical device system 10 includes IMD 20 coupled to modular medical lead system

50. In the example of FIG. 3, IMD 20 includes processor circuitry 24 (also referred to as "processor"), memory 26, stimulation generator 21, sensing module 60, telemetry module 23, sensor 25, and power source 29. Each of these components (also referred to as "modules" may be or include electrical circuitry configured to perform the functions attributed to each respective module). For example, processor 24 may include processing circuitry, stimulation generator 21 may include switch circuitry, sensing module 60 may include sensing circuitry that may be electrically coupled to electrodes 116 to allow for sensing of, e.g., bioelectrical signals of the patient such as bioelectrical brain signals, and telemetry module 23 may include telemetry circuitry. Memory 26 may include any volatile or non-volatile media, such as a random access memory (RAM), read only memory (ROM), non-volatile RAM (NVRAM), electrically erasable programmable ROM (EEPROM), flash memory, and the like. Memory 26 may store computer-readable instructions that, when executed by processor 24, cause IMD 20 to perform various functions. Memory 26 may be a storage device or other non-transitory medium.

In the example shown in FIG. 3, memory 26 stores therapy programs 27 and sense electrode combinations and associated stimulation electrode combinations 28 in separate memories within memory 26 or separate areas within memory 26. Each stored therapy program 27 defines a particular set of electrical stimulation parameters (e.g., a therapy parameter set), such as a stimulation electrode combination, electrode polarity, current or voltage amplitude, pulse width, and pulse rate. In some examples, individual therapy programs may be stored as a therapy group, which defines a set of therapy programs with which stimulation may be generated. The stimulation signals defined by the therapy programs of the therapy group include stimulation pulses that may be delivered together on an overlapping or non-overlapping (e.g., time-interleaved) basis. Stimulation signals may be of any form, such as pulses, continuous-time signals (e.g., sine waves) or the like.

Processor 24 may include any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processor 24 herein may be embodied as firmware, hardware, software or any combination thereof. Processor 24 controls stimulation generator 21 according to therapy programs 27 stored in memory 26 to apply particular stimulation parameter values specified by one or more of programs, such as amplitude, pulse width, and pulse rate.

In the example shown in FIG. 3, modular medical lead system 50 includes one or more electrodes 116 located on electrode module 57. Processor 24 also controls stimulation generator 21 to generate and apply the stimulation signals to selected combinations of electrodes of the electrode module. In some examples, stimulation generator 21 includes a switch module that couples stimulation signals to selected conductors within lead 50, which, in turn, delivers the stimulation signals across selected electrodes. Such a switch module may be a switch array, switch matrix, multiplexer, or any other type of switching module configured to selectively couple stimulation energy to selected electrodes and to selectively sense bioelectrical neural signals of the spine with selected electrodes.

In other examples, however, stimulation generator 21 does not include a switch module. In these examples, stimulation generator 21 comprises a plurality of pairs of voltage sources, current sources, voltage sinks, or current sinks connected to each of electrodes such that each pair of electrodes has a unique signal generator. In other words, in these examples, each of electrodes is independently controlled via its own signal generator (e.g., via a combination of a regulated voltage source and sink or regulated current source and sink), as opposed to switching signals between electrodes.

Stimulation generator 21 may be a single channel or multi-channel stimulation generator. In particular, stimulation generator 21 may be capable of delivering a single stimulation pulse or multiple stimulation pulses at a given time via a single electrode combination or multiple stimulation pulses at a given time via multiple electrode combinations. In some examples, however, stimulation generator 21 may be configured to deliver multiple channels on a time-interleaved basis. For example, a switch module of stimulation generator 21 may serve to time divide the output of stimulation generator 21 across different electrode combinations at different times to deliver multiple programs or channels of stimulation energy to patient 40. In another example, the stimulation generator 21 may control the independent sources or sinks on a time-interleaved bases.

Electrodes 116 of electrode module 57 of modular lead 50 may be constructed of a variety of different designs. For example, one or more leads 50 may include two or more electrodes at each longitudinal location along the length of the lead, such as multiple electrodes at different perimeter locations around the perimeter of the lead at each of the locations, such as by using electrode modules. In one example, the electrodes may be electrically coupled to the switch module via respective conductors that are straight or coiled within the housing the lead, such as in elongate lead body module 52, and run to connector module 59 at the proximal end of the modular lead 50.

Although sensing module 60 is incorporated into a common housing with stimulation generator 21 and processor 24 in FIG. 3, in other examples, sensing module 60 may be in a separate housing from IMD 20 and may communicate with processor 24 via wired or wireless communication techniques. Example bioelectrical signals include, but are not limited to, a signal generated from local field potentials within one or more regions of the brain, for example.

Sensor 25 may include one or more sensing elements that sense values of a respective patient parameter. For example, sensor 25 may include one or more accelerometers, optical sensors, chemical sensors, temperature sensors, pressure sensors, or any other types of sensors. Sensor 25 may output patient parameter values that may be used as feedback to control delivery of therapy. IMD 20 may include additional sensors within the housing of IMD 20 and/or coupled as a separate module via one of lead 50 or other leads. In addition, IMD 20 may receive sensor signals wirelessly from remote sensors via telemetry module 23, for example. In some examples, one or more of these remote sensors may be external to patient (e.g., carried on the external surface of the skin, attached to clothing, or otherwise positioned external to the patient).

Telemetry module 23 supports wireless communication between IMD 20 and an external programmer (e.g., such as programmer device 22) or another computing device under the control of processor 24. Processor 24 of IMD 20 may receive, as updates to programs, values for various stimulation parameters such as amplitude and electrode combination, from programmer 22 via telemetry module 23. The updates to the therapy programs may be stored within therapy programs 27 portion of memory 26. Telemetry module 23 in IMD 20, as well as telemetry modules in other devices and systems described herein, such as programmer 22, may accomplish communication by radiofrequency (RF) communication techniques. In addition, telemetry module 23 may communicate with external medical device programmer 22 via proximal inductive interaction of IMD 20 with programmer 22. Accordingly, telemetry module 23 may send information to external programmer 22 on a continuous basis, at periodic intervals, or upon request from IMD 20 or programmer 22.

Power source 29 delivers operating power to various components of IMD 20. Power source 29 may include a small rechargeable or non-rechargeable battery and a power generation circuit to produce the operating power. Recharging may be accomplished through proximal inductive interaction between an external charger and an inductive charging coil within IMD 20. In some examples, power requirements may be small enough to allow IMD 20 to utilize patient motion and implement a kinetic energy-scavenging device to trickle charge a rechargeable battery. In other examples, traditional batteries may be used for a limited period of time.

Figure 2A:
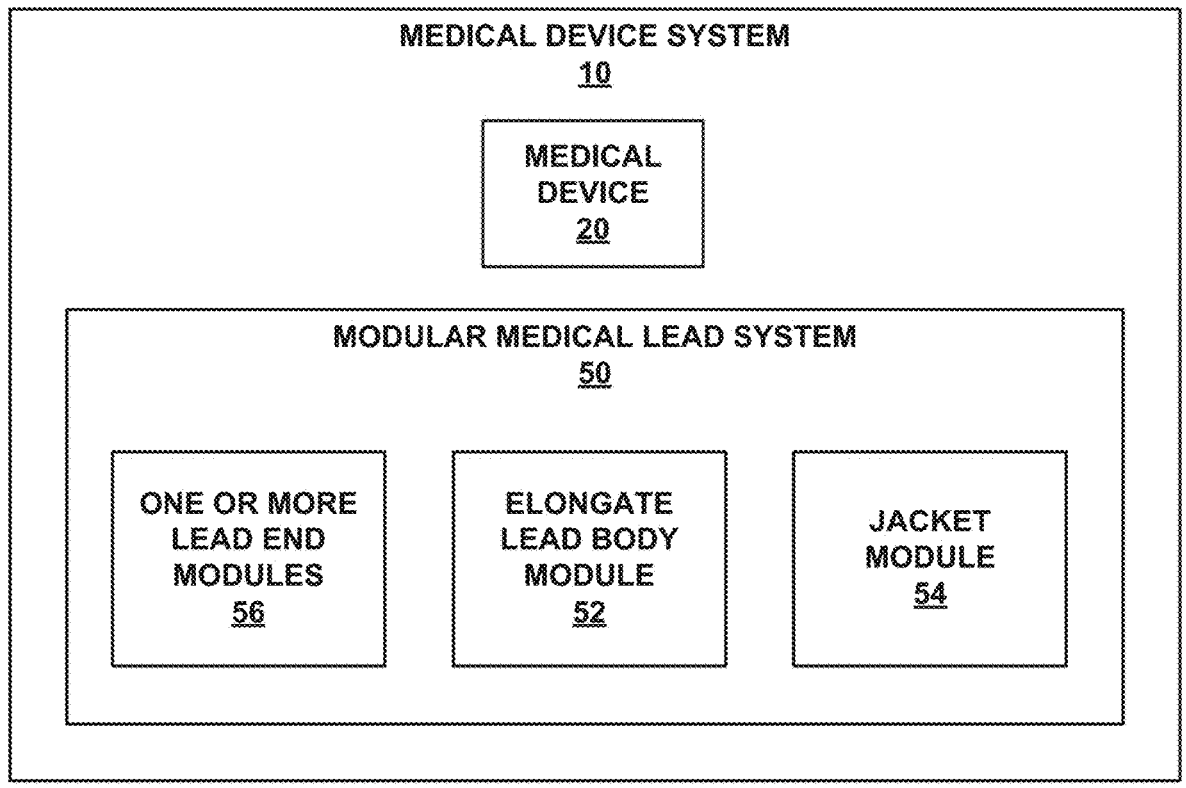
FIG. 2A is a conceptual block diagram of an example of a medical device system.

FIG. 2A is a block diagram of medical device system 10. Medical device system 10 may include medical device 20. Medical device system 10 may include modular medical lead system 50. In some examples, modular medical lead system 50 includes two or more modules to form a medical lead. As described herein, a medical device may deliver electrical stimulation therapy to patient 40 and/or to sense an electrical signal of patient 40 using the medical lead. Modular medical lead system 50 may provide flexibility in manufacturing medical leads, such as by leveraging economies of scale in making modules, rather than making a non-modular lead system.

Modular medical lead system 50 may include one or more lead end modules 56. In one example, lead end module 56 is an electrode module configured to be placed at a target site within patient 40. As another example, lead end module 56 may be a connector module configured to couple the modular medical lead system 50 to corresponding electrical connectors of medical device 20. Other example types of lead end modules may be used.

Modular medical lead system 50 also includes an elongate lead body module 52. In some examples, elongate lead body module 52 includes a plurality of conductors electrically isolated from one another to form separate channels, circuits, or conductive paths through the lead body although techniques described herein also apply to a body module carrying one a single conductor. In some example the plurality of conductors includes eight to sixteen conductors although other numbers of conductors are contemplated, including more than sixteen (e.g., 32 or more). In one example, lead body module 52 includes nine conductors. Elongate lead body module 52 may include conductors in a coiled arrangement. The coiled arrangement of conductors may by wound around a longitudinal axis of elongate lead body module, such as when elongate lead body module is placed on a table and is in a straight position.

In some examples, the coiled arrangement has a diameter of about 0.25 millimeters to about 10 millimeters, such as, e.g., about 0.7 millimeters to about 1.5 millimeters, although other values are contemplated. For instance, the diameter may scale based on the number of conductors and may depend on the application of use. For applications that are non-implantable, such as for use with trialing or monitoring cables that will remain outside a patient's body, the diameters may be 0.50 inches or more. The coiled arrangement of conductors may be made by winding the plurality of conductors around a mandrel, such as described in this disclosure. In some examples, elongate lead body module includes a conductor hub. In other examples, the elongate lead body module includes one or more conductor hubs, such as a first conductor hub positioned near a first end of elongate lead body module 52 and a second conductor hub positioned near a second end of elongate lead body module 52.

Modular medical lead system 50 may include a jacket module 54. Jacket module 54 may be coupled to all or part of other modules of modular medical lead system 50. For example, jacket module 54 may be positioned on the entire elongate lead body module 52 and also on a portion of one or more lead end module 56, such as to insulate portions of the modules from patient (e.g., patient 40). In some examples, jacket module 54 covers a partial portion of elongate lead body module 52. In some examples, multiple jacket modules may be positioned or otherwise coupled to other modules of modular medical lead system 50. Jacket module 54 may be shielded for magnetic resonance imaging. Jacket module 54 may comprise a biocompatible material. Jacket module 54 may comprise a mechanically resilient material. When jacket module 54 surrounds elongate lead body module 52, the modules together may have a total diameter of about 1 millimeter to about 12 millimeters, such as, e.g., about 1 millimeter to about 1.6 millimeters, although other values are contemplated.

The one or more conductor hubs of elongate lead body module 52 may be used as a starting hub in manufacturing modular elongate lead body module 52. The one or more conductor hubs of elongate lead body module 52 may be used as wire distribution hub in manufacturing modular elongate lead body module 52. The conductor hub may include a plurality of channels, where the number of channels correspond to the number of conductors being used in elongate lead body module 52. In an example where lead body module 52 includes only a single conductor, conductor hub may include only a single channel. The conductors may generally be in the coiled configuration on one side of the conductor hub, and may generally be in a straight configuration on the other side of the conductor hub.

Elongate lead body module 52 may be sized and shaped to allow a stylet to pass through an inner lumen defined by the coiled electrodes. As such, in an example, the connector module includes a stylet pass feature. The conductor hub may be sized to fit within jacket module 54. In some examples, where elongate lead body module 52 includes the first conductor hub and the second conductor hub, only one of the two conductor hubs is sized to fit within jacket module 54, such that the other of the two conductor hubs is larger (e.g., has a larger diameter). Yet, in other examples, each of the two conductor hubs are sized and shaped to fit within jacket module 54.

As will be described further below, the conductor hub may include a drive feature. The conductor hub may define an opening, such as may form the drive feature. In an example, the drive feature is an opening configured to couple to a component of a winder apparatus or an assembly apparatus. For example, the drive feature may be configured to couple to a motor of the winder apparatus, whether directly or indirectly. As such, a component of the winder apparatus may couple to the conductor hub, such as by being disposed inside the drive feature. In other examples, the conductor hub includes an external drive features, such that a component of the winder apparatus may couple to the outside of the conductor hub (e.g., such as by using ridges or grooves to form a mechanical connection).

The conductors of elongate lead body module 52 may extend from a first end to a second end of elongate lead body module 52. In an example, a portion of one or more of the plurality of conductors extends past the conductor hub. In an example, the portion is an ablated insulation end. For example, the portion is ablated such that the electrically insulated layer of the conductor is stripped away, such as for coupling to other modules. This may include a welded coupling, such as to the lead end module.

Figure 2B:
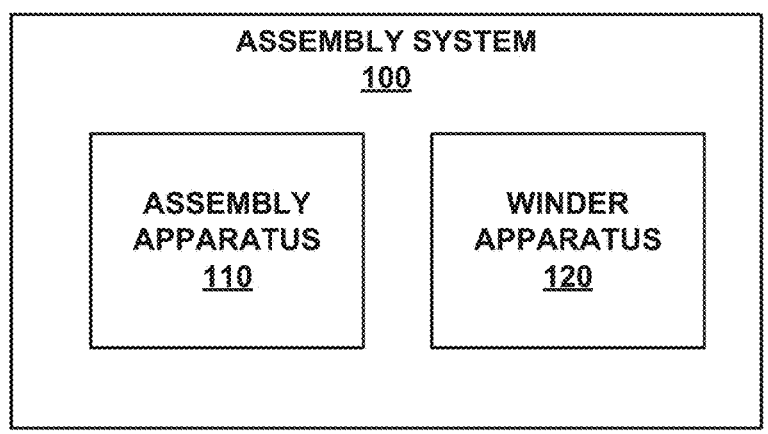
FIG. 2B is a conceptual block diagram of an example of an assembly system.

FIG. 2B is a conceptual block diagram of an example of an assembly system 100. Assembly system 100 may include an assembly apparatus 100. Assembly system 100 may include a winder apparatus 120. In some examples, these apparatuses may be positioned at a single station (e.g., a work station or a manufacturing station). In some examples, these apparatuses may be positioned at separate stations (e.g., two different stations). Yet in other examples, assembly system 100 comprises a combined assembly/winder apparatus. Assembly system 100 may include automated portions, such as by using robotic arms, mechanized fixtures, automated computer systems, or the like. Example operation of assembly system 100, e.g., to form an elongate lead body module, is described further below.

FIG. 4A is a conceptual diagram illustrating an example of modular medical lead 50. Modular lead 50 may include elongate lead body module 52, electrode module 57, and connector module 59 joined with each. In the example of FIG. 4A, elongate lead body module 52 includes two conductor hubs 270A and 270B. In this example, there are nine conductors corresponding to nine electrodes and nine electrical contacts, such that the modular lead 50 defines nine isolated electrical paths or channels for delivery of therapy and/or sensing of electrical signals. For example, electrodes 201-206 are illustrated on electrode module 57 (electrodes 207-209 not shown). In this example, there are three sets of three electrodes on the electrode module, such that each set is aligned along a longitudinal axis of the electrode module and the sets are placed circumferentially around outer surface of electrode module 57. Likewise, for example, electrical contacts 221-229 are positioned along connector module 59. Conductors 251-259 may be in a coiled arrangement, such as may be seen in elongate lead body module 52 of FIG. 4A. In this example, conductor 251 interconnects electrode 201 and electrical contact 221. As such, conductor 252 interconnects electrode 202 and electrical contact 222, and so on for the plurality of conductors.

Figure 4D:
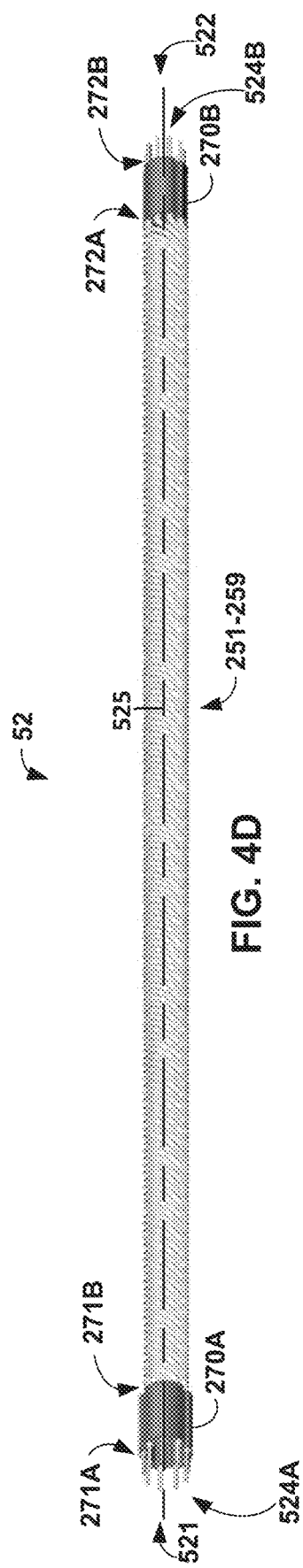

FIG. 4D is a conceptual diagram of the example elongate lead body module 52 shown in FIG. 4A prior to be joined to electrode module 57 and connector module 59, and without jacket module 54. As shown, each conductor of plurality of conductors 251-259 extends from first end 27A to second end 271B of first conductor hub 270A relative to a longitudinal axis 525 of elongate lead body module 52 such that a portion 524A of conductors 251-259 extends beyond first end 271A of first conductor hub 270A. In some examples for each conductor of conductors 251-259, the portion 524A that extends beyond first end 271A of first conductor hub 270A is coupled (not shown in FIG. 4D) to a respective electrical conductor of a lead end module (e.g., such as electrode module 57 as in the examples of FIG. 4A), to allow respective electrical signals to be conducted between the respective conductors of the lead end module and the conductors 251-259 of elongate lead body module 52. Elongate lead body module 52 also includes second conductor hub 270B. Plurality of conductors 251-259 are electrically isolated from one another and mechanically coupled to second conductor hub 270B such that conductors 251-259 are in a fixed arrangement relative to one another (such as may be seen at second end 522). In some examples a second end 272B of second conductor hub 270B is nearer second end 522 of elongate lead body module 52 than a first end 272A of second conductor hub 270B. In some examples, conductors 251-259 extend from first end 272A to second end 272B of second conductor hub 272 relative to longitudinal axis 525 of elongate lead body module 52. In some examples, each conductor of plurality of conductors 251-259 extend from first end 272A to second end 272B of second conductor hub 270B, such that a second portion 524B of conductors 251-259 extend beyond second end 272B of second conductor hub 272. In some examples, lengths of the conductors of second portion 524B may be long enough to reach a corresponding electrode or connector contact or ring itself, such as may not require the use of a joint between modules.

In the example of FIG. 4D, conductors 251-259 are in a coiled arrangement between first end 521 of elongate lead body module 52 and second end of elongate lead body module 52. More particularly, in this example, the coiled arrangement extends between first conductor hub 270A and second conductor hub 270B. In some examples first conductor hub 270A may have a larger cross-sectional dimension (e.g., diameter) than second conductor hub 270B. In some examples, second conductor hub 270B may have a larger cross-sectional dimension than first conductor hub 270A. First conductor hub 270A and second conductor hub 270B may be sized and shaped to for a desired purpose. In some examples, one or both of first conductor hub 270A and second conductor hub 270B may not be required to fit inside an outer jacket (e.g., jacket module 54 or another sheath or cover). In some examples, one end of a conductor hub may include a larger outer cross-sectional dimension (e.g., diameter) than an inner diameter of the outer jacket, such that only one end of the conductor hub may need to be inside (e.g., strung or passed through) the lumen of the outer jacket (e.g., the conductor hub may be further covered by a molding or a separate covering process). Elongate lead body module 52 may have a straight arrangement of conductors 251-259 at first end 521 and second end 522, such as to form a "straight to coiled to straight" arrangement of the conductors. Each of conductors 251-259 extends through closed channels or conduits formed in hubs 270A and 270B to fix the conductors 251-259 to the hubs. In other examples, the arrangement at first end 521 may be different than the arrangement at second end 522. Likewise, first conductor hub 270A may include a different design than second conductor hub 270B. Different examples of designs of conductor hubs are disclosed herein, such as with reference to FIG. 5 generally (e.g., FIG. 5A, FIG. 5B, etc.). As such, the arrangement of the conductors may be in a fixed arrangement on first end 521 and in a different fixed arrangement on second end 522. In some examples, the winding apparatus described herein may secure both of first end 521 and second end 522 to a structure of the winding apparatus during winding.

In some examples, individual conductors 251-259 includes a single filar configuration. In other examples, the conductor includes a multi-filar configuration. In yet other examples, the conductor includes coils of multi-filar coils. For example, a first set of coiled filars and a second set of coiled filars may be wound together, such as to form the conductor. The coiled arrangement of conductors of the elongate lead body module may include one or more configurations of filars. For example, the coiled arrangement may include a single filar conductor, a multi-filar conductor, multiple sets of multi-filar conductors, or any combination thereof.

FIG. 4B is a conceptual diagram illustrating an example of a portion of modular medical lead system 50 including electrode module 57. In one example, respective conductors 211-219 may extend from electrode module 57. The respective conductors 211-219 may be coupled to corresponding conductors 251-259 of lead body module 52, for example. As discussed herein, the portion of the conductors that extend from conductor hubs 270A or 270B may couple to other conductors of other modules (such as in the example of FIG. 4B), or may connected directly to electrode module 57, such as directly to electrodes 201-203, where electrodes 204-209 are not shown, or directly to a portion of a housing or body of electrode module 57.

FIG. 4C is a conceptual diagram illustrating an example of a portion of a modular medical lead system 50 that includes connector module 59. Respective conductors 231-239 of connector module 59 may be used to connect conductors 251-259 of lead body module 52 to electrical contacts 221-229. In another example, the portion of the conductors that extend beyond conductor hub 270B may be directly coupled to electrical contacts 221-229, or to a portion of a housing or body of connector module 59. Respective conductors 211-219 and 231-239 may comprise the same material or insulated configuration as conductors 251-259.

Figure 4E:

FIG. 4E is a conceptual diagram illustrating an example of a portion of a modular medical lead 50 including jacket module 54 surrounding a portion of elongate lead body module 52. Here it can be seen that jacket module 54 may be configured to cover conductors of module 52 to insulate the conductors from environments such as inside patient 40. In an example, the coiled arrangement of elongate lead body module 52 supports the modular architecture of the examples herein. In an example, conductors in the form of one or more cables (e.g., multiple grouped wires) may be used instead of the coiled arrangement of the example of FIG. 4D, such as to provide an elongate lead body module. In other examples, one or more of the conductors is a cable and one or more of the conductors is a single wire. In one example, elongate lead body module 52 includes a single cable comprising a plurality of wires (e.g., nine wires), and the plurality of wires of the single cable may extend through one or more conductor hubs. In another example, the single cable itself may be used to connect two modules of modular medical lead system 50.

In an example, for a coiled arrangement in elongate lead body module 52, such as after coil construction is completed, both ends may terminate and stabilized for presentations suitable to connect (e.g., weld) to distal and proximal ends (e.g., modules) of elongate lead body module 52. In an example, the coiled arrangement may be strung into jacket module 54.

Figure 4F:

FIG. 4F is a conceptual diagram illustrating an example of a portion of a modular medical lead system. In this example, electrode module 57 is coupled to elongate lead body module 52. Conductor hub 271 presents the plurality of conductors in an arrangement suitable to weld or otherwise electrically couple to corresponding portions of electrode module 57.

Figure 5E:
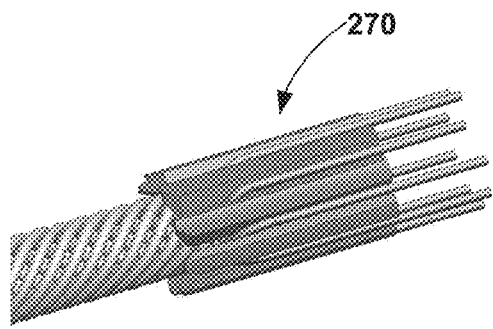
FIGS. 5A-5U illustrate examples of portions of a modular medical lead system.
Figure 5F:
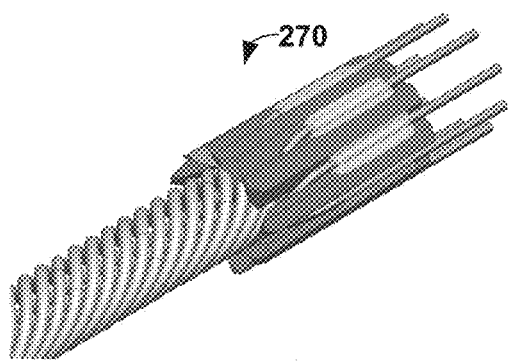
Figure 5G:
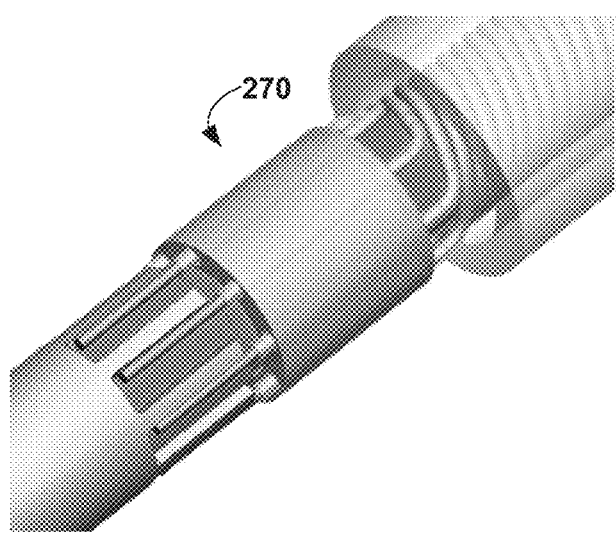

In the example of FIG. 5G, a plurality of conductors are coupled conductor hub 270. Conductor hub 270 may maintain a desired presentation ("arrangement") of the conductors. A portion of the conductors that extend beyond conductor hub 270 may be ablated, such as may result in removing an electrically insulating layer of the conductors. Conductor hub 270 may provide a circular presentation of the conductors, such as for ease of coupling the conductors to another module. Other presentations may be used, such as to correspond to a cross-sectional profile of other modules. In the example of FIG. 5G, after exiting the channels of conductor hub 270, conductors are positioned adjacent electrically conductive portions of another module, such as for electrically coupling the conductors to respective electrodes on an electrode module. Conductors may be in coiled arrangement on one side of conductor hub 270 and in a straight arrangement on the other side of conductor hub 270.

In some examples, the channels of conductor hub 270 are through-hole channels. Conductor hub 270, in the example of FIG. 5G, is illustrated as partially transparent. As such channels of conductor hub 270 may be seen. In some examples, such as the channels shown are straight, such as may be substantially parallel to the longitudinal axis of elongate lead body module 52 or of conductor hub 270. In other examples, the channels include a spiral shape, where the channels spiral around conductor hub 270. The channels of conductor hub 270 may allow for handling of an individual conductor of the plurality of conductors, such as to weld the individual conductor to a respective conductor of another module, or to a portion of a housing of another module. Such handling may be controlled, such as by providing the ability to manipulate the conductors without disturbing the coiled arrangement of conductors of the medial portion of elongate lead body 52.

Figure 7A:
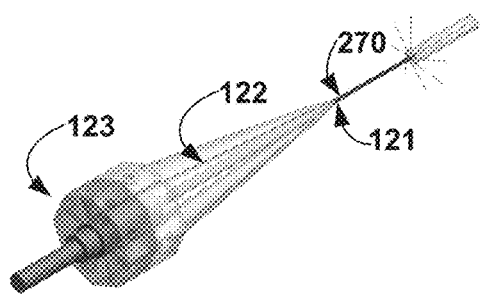
Figure 7B:
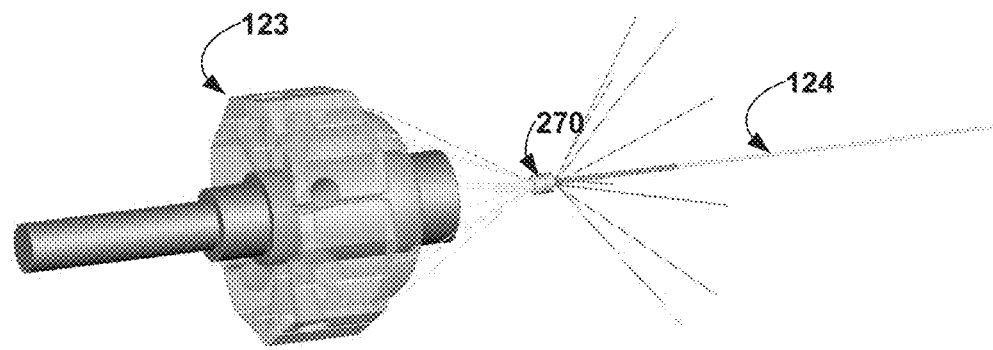
Figure 7C:
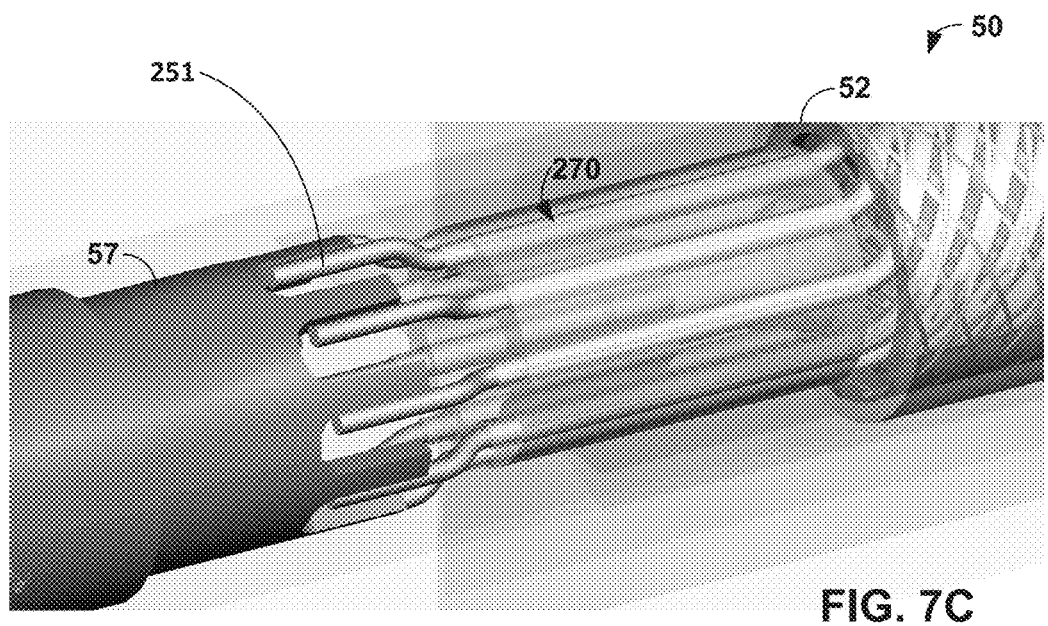

FIG. 7C is a conceptual diagram illustrating an example portion of modular medical lead system 50. In the example shown, the distal ends of the plurality of conductors (e.g., conductor 251) extending beyond hub 270 are aligned and joined with corresponding conductors of electrode module 57, e.g., via laser welding or other suitable technique. As described herein, conductor hub 270 may be used to form elongate lead body module 52. Some examples of conductor hub 270 may be used as a starting conductor hub, such as for beginning to wind conductors around mandrel 124. Other examples of conductor hub 270 may be used as a finishing (or "terminating") conductor hub, such as for securing a second end of elongate lead body module 52 after a desired coiled arrangement is formed in the medial section of elongate lead body module 52.

Figure 7D:
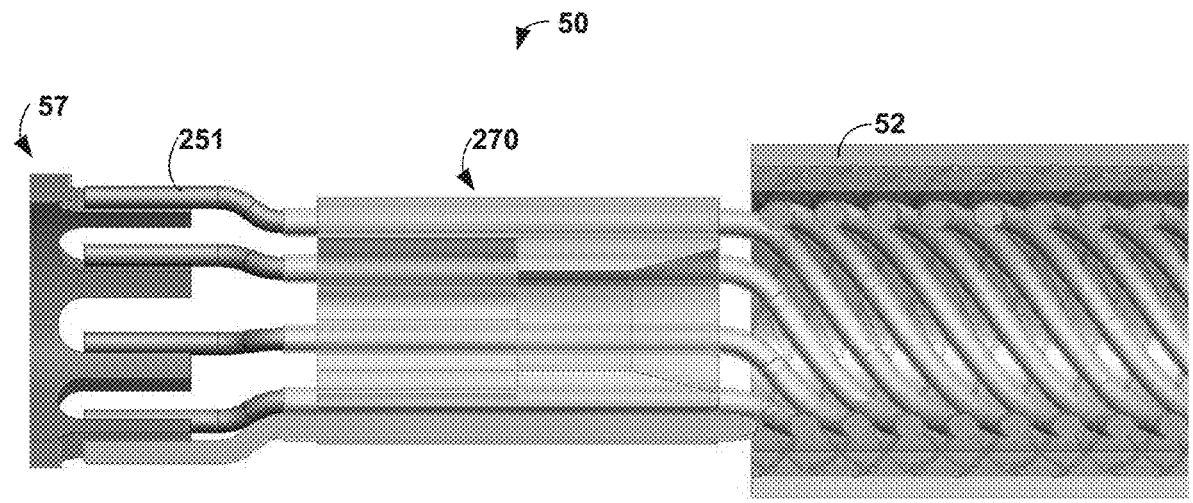

FIG. 7D is a conceptual diagram illustrating a cross section of an example of modular medical lead system 50 shown in FIG. 7C. As shown, the conductors (e.g., conductor 251) having a radially symmetric arrangement past the conductor hub. The conductors of elongate lead body module may transition, via conductor hub 270, from a straight arrangement to a straight arrangement of the electrode module 57 (e.g., a "straight to straight" arrangement).

Figure 7E:
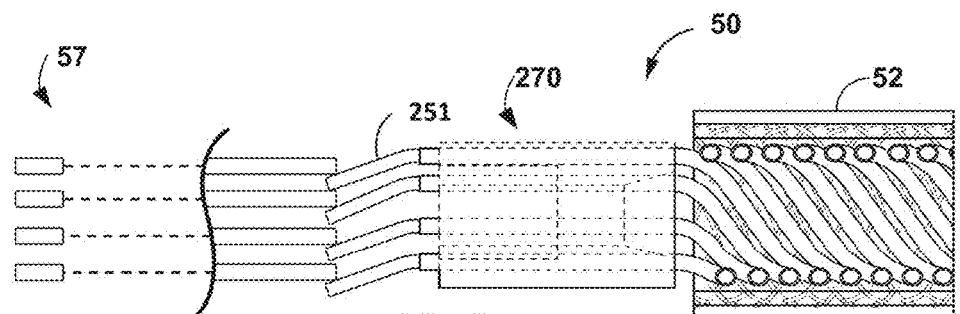

FIG. 7E illustrates another example cross section of modular medical lead system 50, such as may include conductors having an angled or helical arrangement extending from the elongate lead body module 50. In an example, respective conductors of an electrode module 57 (or connector module 59), for example, may be in a straight arrangement, angled arrangement, or helical arrangement. As such, the conductors of elongate lead body module 52 and respective conductors one or more other modules may mate to each one another with a desired geometry. In some examples, such a geometry may increase provide better accessibility to weld the conductors to one another. In the example of FIG. 7E, the conductors of the elongate lead body module 52 are shown in an angled arrangement, while the conductors of the electrode module 57 are shown in a straight arrangement (e.g., parallel to a longitudinal axis of the electrode module 57) (e.g. a "angled to straight" arrangement).

Figure 7F:
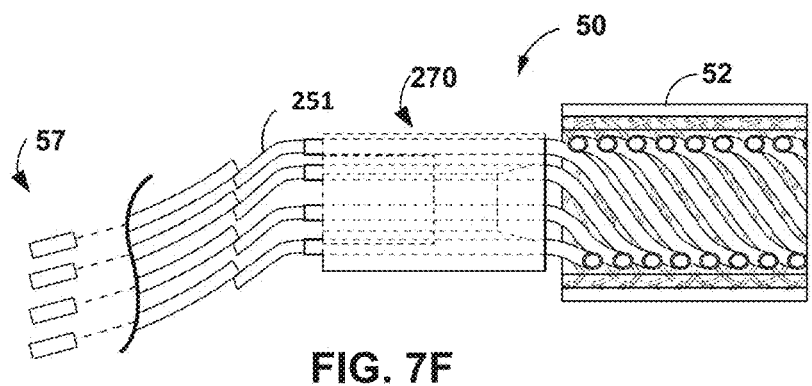

In the example of FIG. 7F, the conductors (e.g., conductor 251) of the elongate lead body module 52 are shown in an angled arrangement, and the conductors of electrode module 57 are also shown in an angled arrangement (e.g., an "angled to angled" arrangement).

As noted above, some aspects of the disclosure relate to the example assembly system 100 shown in FIG. 2B. In some examples, assembly system 100 may be used to manufacture a module lead body, such as, e.g., module lead body 52. As described above, assembly system 100 may include an assembly apparatus 100. Assembly system 100 may include a winder apparatus 120. In some examples, these apparatuses may be positioned at a single station (e.g., a work station or a manufacturing station). In some examples, these apparatuses may be positioned at separate stations (e.g., two different stations). Yet in other examples, assembly system 100 comprises a combined assembly/winder apparatus. Assembly system 100 may include automated portions, such as by using robotic arms, automated computer systems, or the like. Example operation of assembly system 100, e.g., to form an elongate lead body module, is described further below.

Figure 9A:
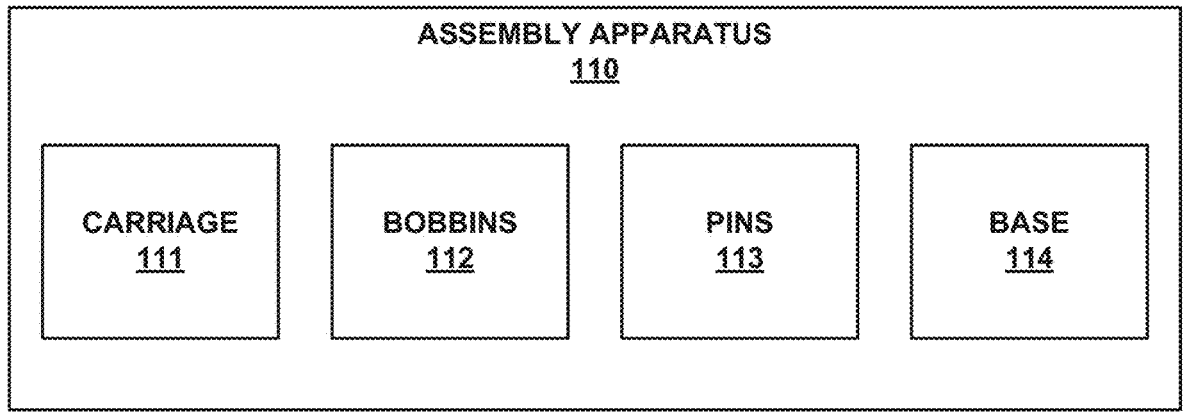
FIGS. 9A-C illustrate examples of an assembly system.
Figure 9B:
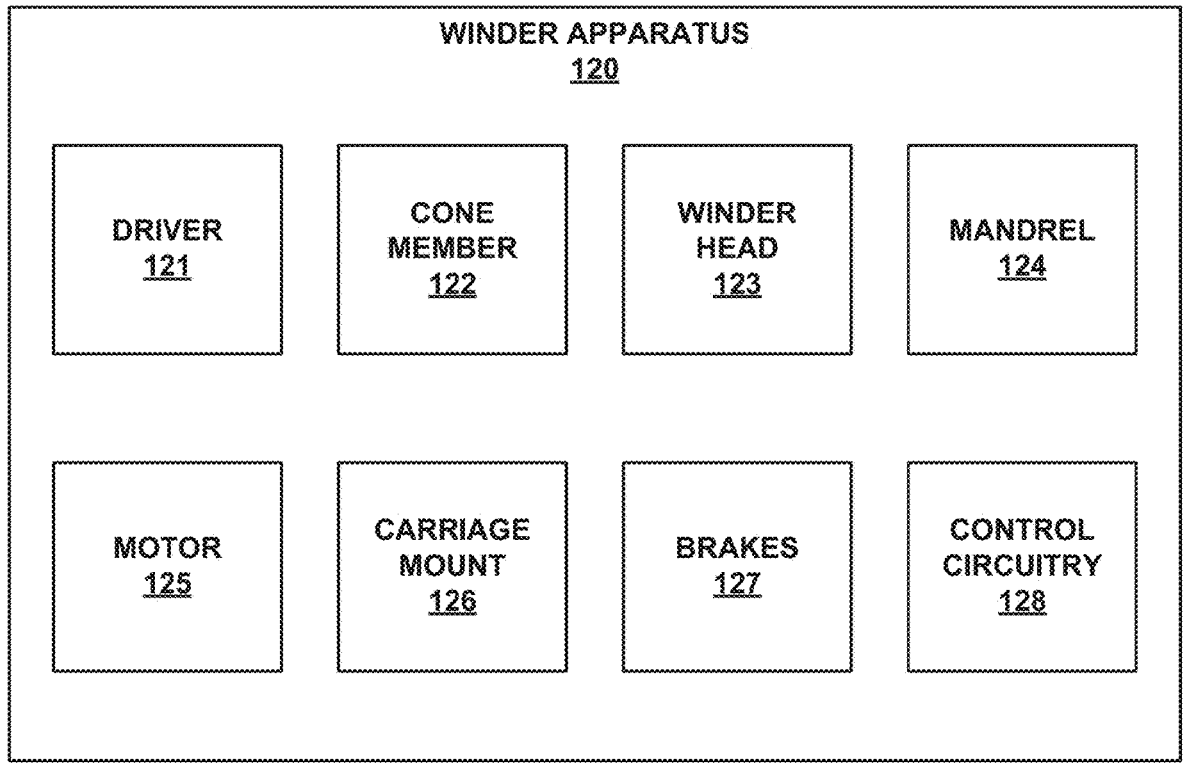

FIGS. 9A-B are conceptual block diagrams of examples assembly apparatus 110 and winder apparatus 120, respectively, of an assembly system, such as assembly system 100 of FIG. 2B). As shown, assembly apparatus 110 may include carriage 111, bobbins 112 rotatably coupled to carriage 111 via pins 113 extending from carriage 111. Assembly apparatus 110 may include a base 114. In an example, base 114 is used to secure the carriage for coupling conductors to the conductor hub. In some examples, assembly apparatus 110 include robotic arm 115.

Winder apparatus 120 may include driver 121, such as may be coupled to cone member 122. Cone member 122 may be coupled to winder head 123. Winder apparatus 120 may include mandrel 124. In an example, winder apparatus 120 includes one or more motors 125. In one example, there is a motor at each end of winder apparatus 120, such that two motors rotate in sync with each other to rotate mandrel 124 during the winding process to create the coiled arrangement of elongate lead body module 52. In some examples, another motor is used, such as may be coupled to carriage mount 126. Carriage 111 may be mounted to carriage mount 126. And using another motor, carriage mount 126 may be moved along a longitudinal axis of mandrel 124. Mandrel 124 may extend through an opening defined by carriage 111.

In an example, coiling the conductors around mandrel 124 includes rotating mandrel 124 with one or more motors 125, and creating distance between carriage mount 126 and the conductor hub comprises moving carriage mount 126 away from the conductor hub causing the conductors to unwind from bobbins 112 and wind around mandrel 124. Bobbins 112 may be controlled using brakes 127, in some examples. In some examples, winder apparatus 120 may not necessarily require brakes 127 (e.g., winder apparatus 120 may comprise a torque control system, a pad, a tensioning system, or an additional motor, such as to control the rate of bobbins 112 angular motion). In other examples, coiling the conductor around mandrel 124 includes one or more of rotating carriage mount 126 in addition to, or instead of rotating mandrel 124 or creating distance between the carriage mount 126 and the conductor hub is accomplished by moving the mandrel and conductor hub away from carriage mount 126. In some examples, the mandrel may move while the carriage mount 126 remains in place (e.g., any relative motion of the mandrel and the carriage mount). Brakes 127 may be coupled to carriage mount 126. Assembly system 100 may include control circuitry 128, such as to control portions of winder apparatus 120. In some examples, control circuitry 128 may control portions of assembly apparatus 110, such as robotic arm 115.

In some examples, assembly apparatus 110 and winder apparatus 120 are a part of a manufacturing line, such as at two separate stations. In some examples, assembly apparatus 110 and winder apparatus 120 are a part of the same apparatus (or same station), that may be partially or fully automated, such as may include using machine vision (e.g., video cameras and computers), to manufacture the elongate lead body module, for example. In some examples, in forming elongate lead body module 52, assembly apparatus 100 and winder apparatus 120 may automatically, continue forming lead 50, such that the techniques described herein may include forming lead 50 without necessarily requiring coupling more than two modules to one another as separate steps.

Figure 9C:
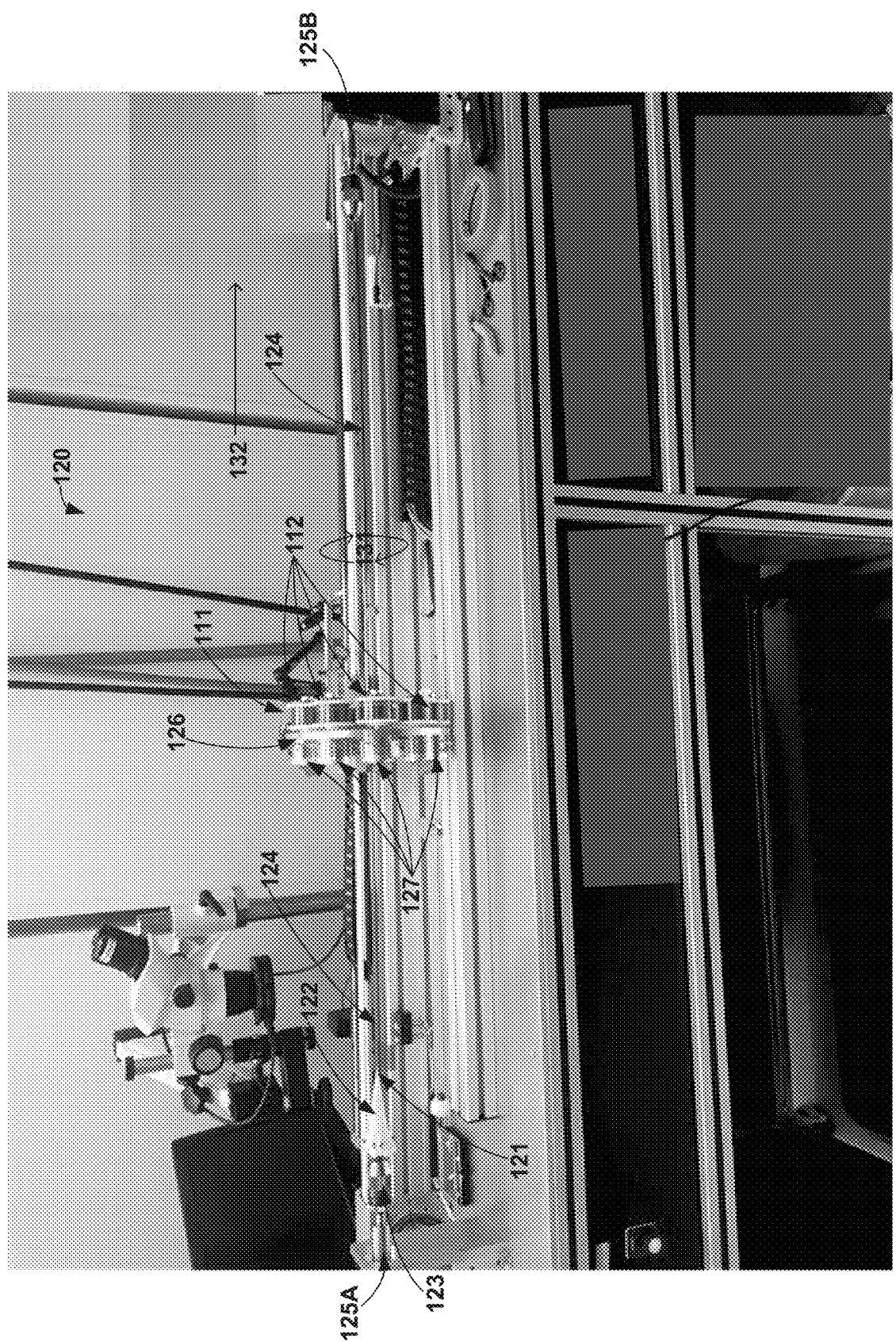

FIG. 9C is an image illustrating an example assembly system 100 including winder apparatus 120 and portions of assembly apparatus 110 for manufacturing a lead body module, such as, e.g., lead body module 52. In FIG. 9C, winder apparatus 120 is shown on a table or a workstation. Winder apparatus 120 may include motors 125A and 125B on opposite ends of winder apparatus 120. Mandrel 124 may extend from one end to the other of winder apparatus 120. Winder head 123 may be mechanically coupled to motor 125A. Cone member 122 may be mechanically coupled to winder head 123. Driver 121 may be coupled to cone member 122. In other examples driver 121 is coupled to winder head 123 or motor 125A. In some examples, mandrel 124 is coupled to driver 121. In other examples, mandrel 124 is coupled to cone member 122 or winder head 123. In some examples, carriage 111 may include an interfacer to couple, align, register, or otherwise engage motor 125 and winder head 123, such as may include not using a cone member (e.g., such as by using hub holder 275 as may be seen in FIG. 6F).

Carriage 111 may include a plurality of bobbins 112, such as may be arranged with radial symmetry on a side of carriage 111. Carriage 111 may be mounted to carriage mount 126. Carriage mount 126 may be coupled to a plurality of brakes 127. Each brake of plurality of brakes 127 may correspond to a respective bobbin of plurality of bobbins 112. Carriage mount 126 may be coupled to another motor to move carriage mount 126 in a straight direction 132 away from the beginning side (e.g., with motor 125A, as shown). Mandrel 125 may be rotated, such as by motors 125A and 125B, in a rotational direction 131. In the example of FIG. 9C, rotational direction 131 is clockwise. In some examples, rotational direction 131 is counter-clockwise.

During the process to wind conductors around mandrel 124, mandrel 124 rotates in rotational direction 131 and carriage mount moves in straight direction 132, such as to cause the conductors wound around bobbins 112 to coil around mandrel 124.

Figure 6B:
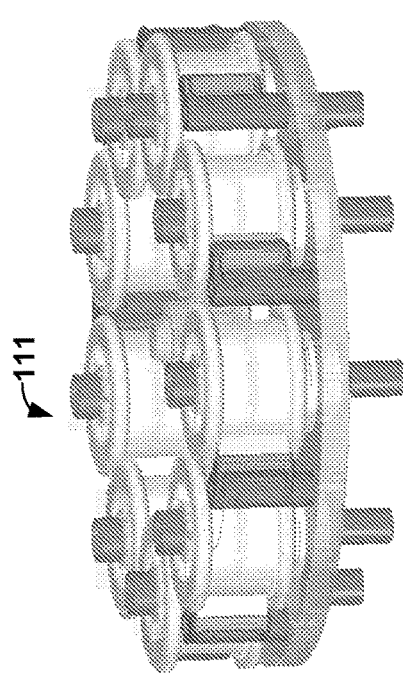
FIGS. 6A-6R illustrate examples of portions of an assembly system.
Figure 6D:
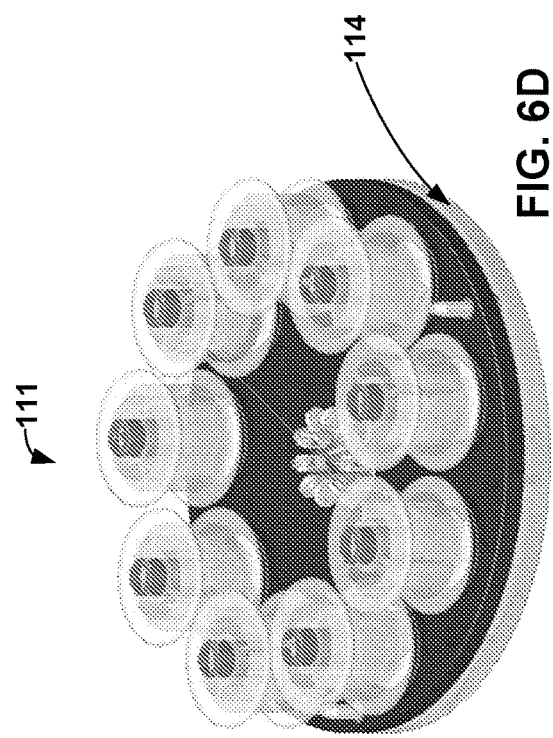
Figure 6A:
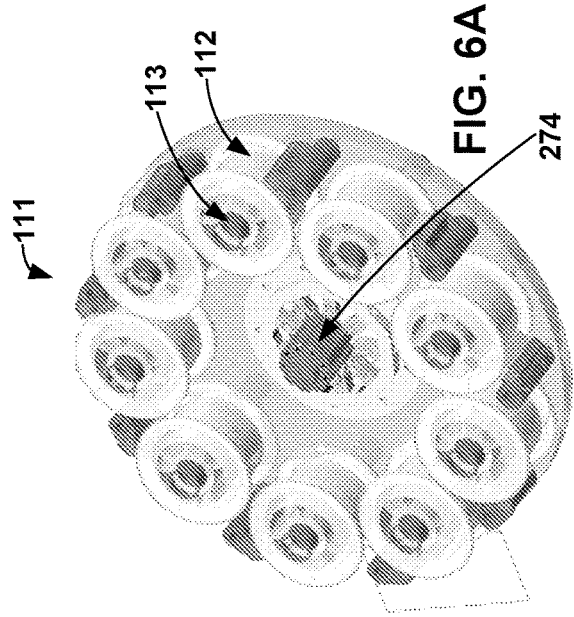
Figure 6C:
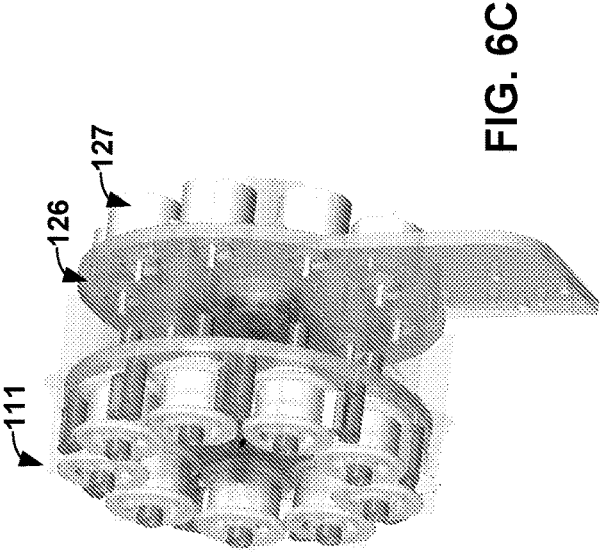
Figure 6F:
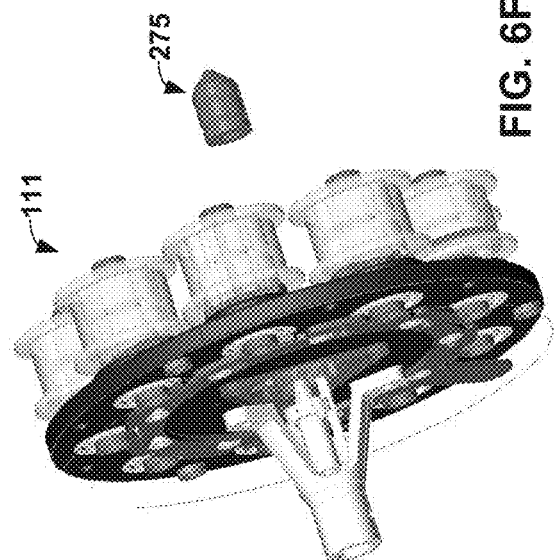
Figure 6H:
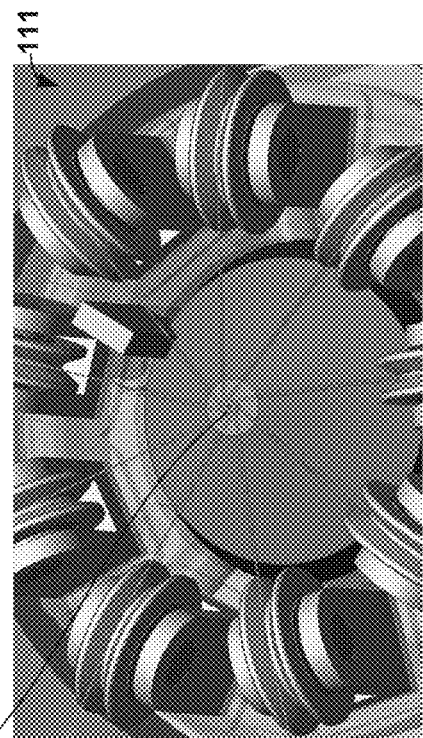
Figure 6E:
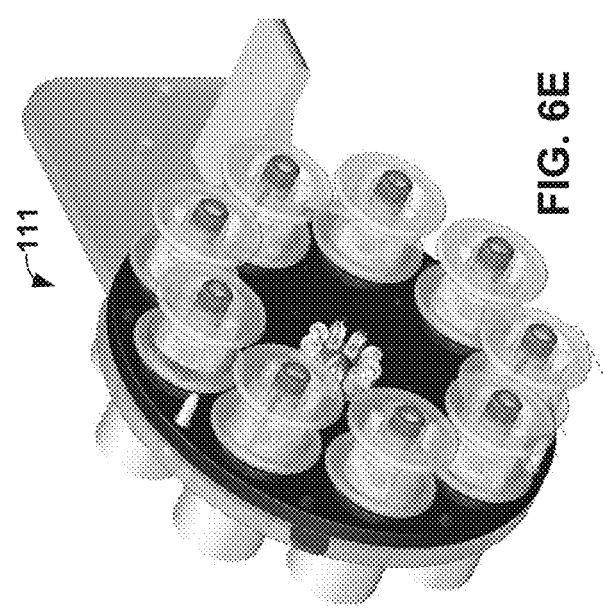
Figure 6G:
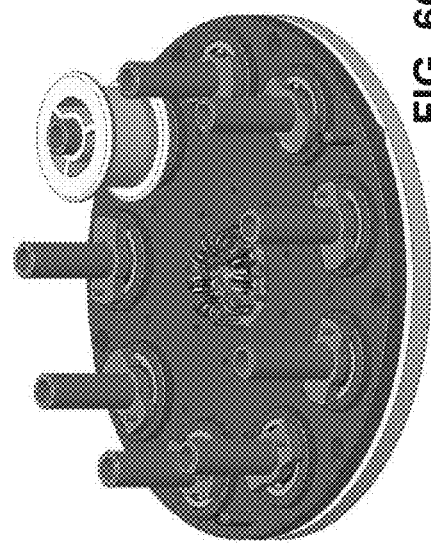
Figure 6J:
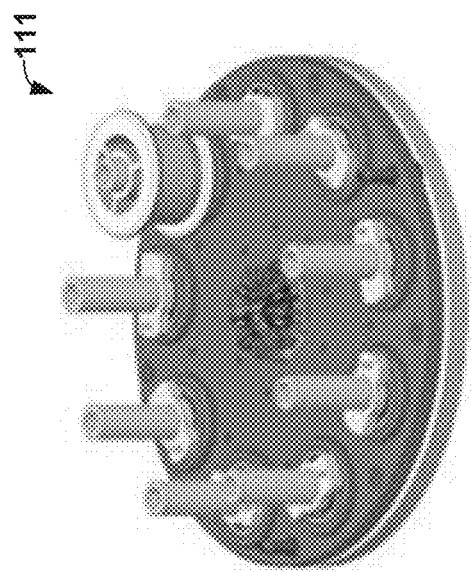
Figure 6L:
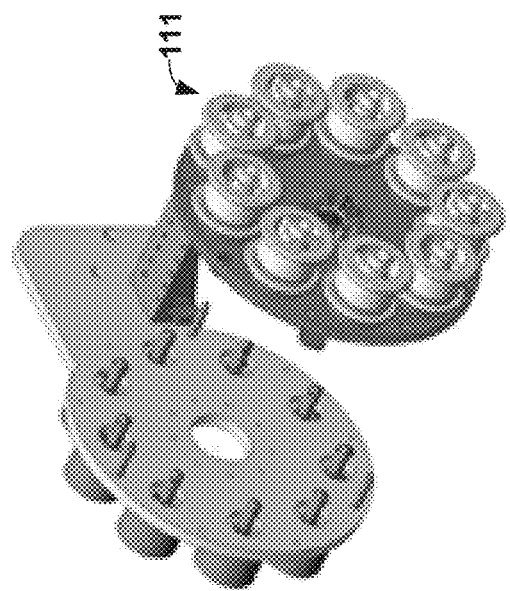
Figure 6I:
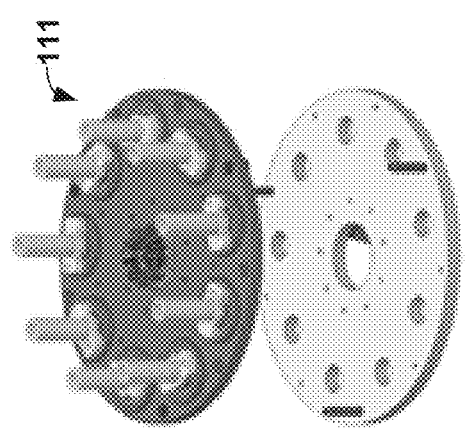
Figure 6K:
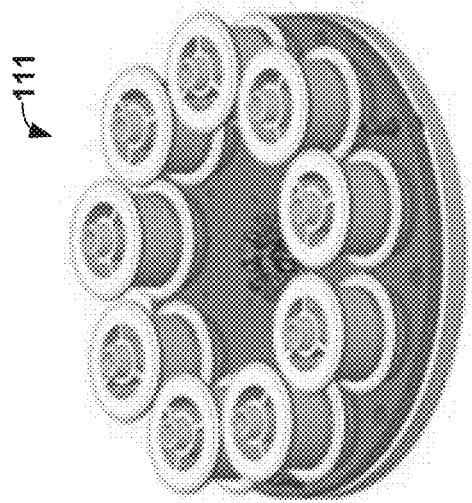
Figure 6M:
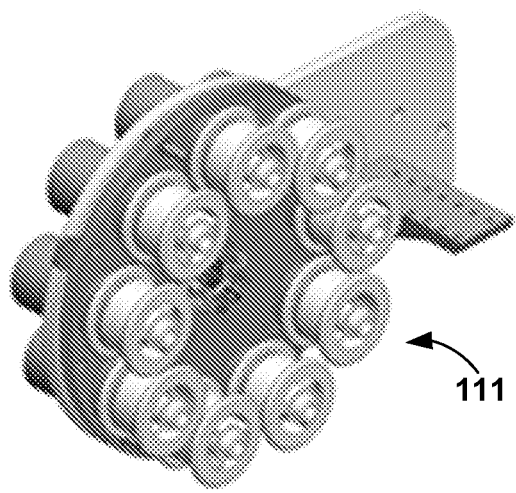
Figure 6N:
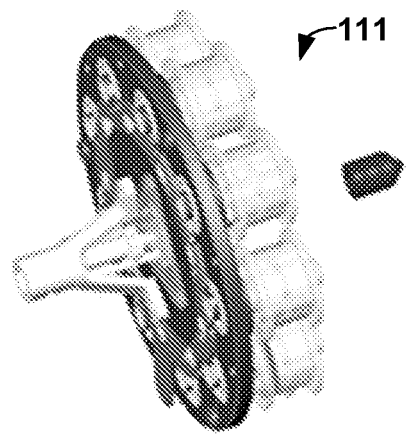
Figure 6O:
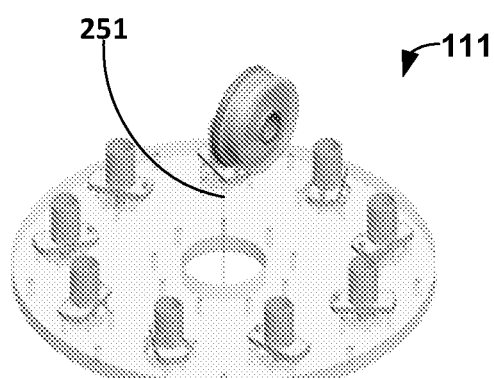
Figure 6P:
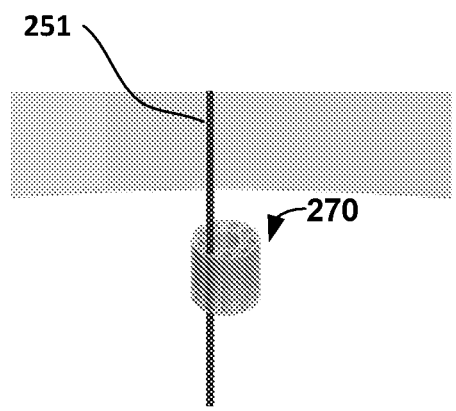
Figure 6Q:
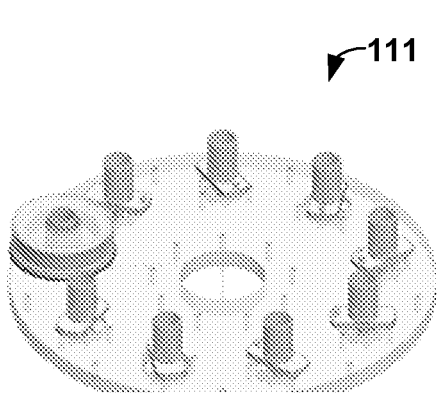
Figure 6R:
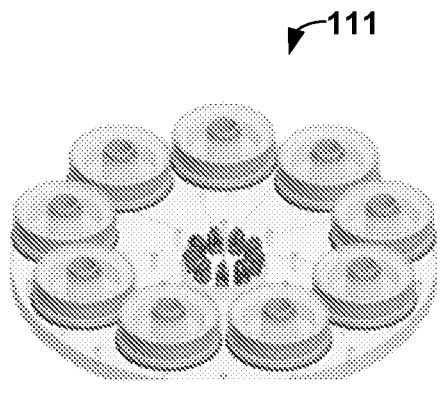

FIGS. 6A-R illustrate examples of components of assembly apparatus 110 of assembly system 100. As shown in FIG. 6A, carriage 111 includes a plurality of pins, such as pin 113. A respective plurality of bobbins may be positioned on the plurality of pins, such as bobbin 112. In some examples, conductor hub 270 is positioned within a central opening of carriage 111, such as before the winding process begins. FIG. 6B illustrates an example of carriage 111 from another view.

FIG. 6C illustrates an example of carriage 111 aligned to be mounted to carriage mount 126 of a winder apparatus. Winder apparatus may include a plurality of brakes, such as brake 127. Each brake may correspond to a respective bobbin, such as to control a rotation rate during the winding process to manufacture the elongate lead body module.

FIG. 6D illustrates an example of carriage 111, such as coupled to a carriage base 114. Base 114 may be used to secure carriage 111, such as when mating the respective conductors to conductor hub 270. As can be seen from FIGS. 6C and 6D, carriage 111 may be coupled to a portion of assembly apparatus in some examples, and may be coupled to a portion of a winder apparatus in other examples. Generally, assembly apparatus 110 may be used to position the conductors within the conductor hub 270. Generally, winder apparatus 120 may be used to coil the conductors to form the elongate lead body module, such as by using conductor hub 270 as a starting hub or ending hub.

FIGS. 6E-H illustrate examples of carriage 111. For example, FIG. 6H illustrates a central portion of carriage 111, such as may include guide wheels, where each individual conductor extends from the respective bobbin, to a respective guide wheel, to a respective channel of conductor hub 270.

FIGS. 6O-N illustrate examples of carriage 111. For examples FIG. 6L illustrates an exploded view showing how brakes may be coupled to bobbins.

FIG. 6O illustrates an example of carriage 111. In this example, an individual conductor extends from a single bobbin. As can be seen in the conceptual example of FIG. 6P, the individual conductor may mate with conductor hub 270, such as by being thread into a channel of conductor hub 270. A robotic arm may be automated to thread the conductor into the channel of conductor hub 270, such as by using machine vision. In other non-automated examples, a human operator may thread the conductor into the channel. Such a process may be completed for each of the conductors 251-259 of lead body module 52.

FIGS. 6Q-R illustrate examples of carriage 111. In some examples, the number of bobbins and pins may correspond to the number of conductors to be included in the elongate leady body module.

FIG. 7A illustrates coiled conductors and conductor hub 270 for an elongate lead body module coupled to a portion of winder apparatus 120 during a manufacturing step. Winder head 123 may be mechanically coupled to cone member 122. A motor (not shown) may be coupled to winder head 123. A driver 121 may be coupled to cone member 122. Driver 121 may be coupled to conductor hub 270. In some examples, driver 121 is inserted into an opening of conductor hub 270. In other examples, driver 121 is an external driver, such that conductor hub 270 fits within a portion of driver 121 (e.g., hub holder 274, such as may be seen in FIG. 6A). As the motor rotates, winder head 123, cone member, 122, driver 121, conductor hub 270, and a mandrel, such as shown in FIG. 7B, also rotate with the motor.

FIG. 7B illustrates a conceptual example of a part of a method for assembling modular medical lead system 50. For example, as winder head 123 is driven by a motor (not shown), a mandrel 124 rotates to wind conductors around mandrel 124. In some examples, mandrel 124 is coupled to winder head 123 at least via conductor hub 270. In other examples, mandrel 124 is directly coupled such as to driver 121, such that conductor hub 270 is slidably coupled to mandrel 124.

In the example of FIG. 7G, conductor hub 270 is a stabilizer hub. The stabilizer hub may be coupled to mandrel 124 before winding begins. Or, in other examples, the stabilizer hub may be coupled to mandrel 124 after winding the conductors into the coiled arrangement and before spring-back of the coiled conductors occurs after the winding process has stopped. In some examples, spring-back naturally occurs due to the coiled arrangement of conductors.

As will be described below, a stabilizer hub may be temporarily used during a manufacturing process of lead body module 52 to drive and control the unwinding (e.g., speed, amount, etc.) during spring back after the coiling of conductors 251-259 is complete. From the stabilizer hub, the ordered conductors may be transferred to final hub or finishing hub used for lead body module 52, e.g., when joined with other modules of modular lead 50.

In the conceptual example of FIG. 7H, conductor hub 270 is a spiral hub, such that the spiral hub includes grooved channels that are spiraled around conductor hub 270. In an example, the spiral hub is used as a finishing conductor hub, such as to wind the plurality of conductors over the hub. In some examples, the spiral hub is coupled to the coiled arrangement to form the second end of elongate lead body module 52. In an example, the spiral hub is used to secure the conductors during the winding process. In an example, the spiral hub presents the portion of the conductors that extend from the hub in an arrangement, such as a straight arrangement or a corresponding spiraled (e.g., helical) arrangement.

In the conceptual example of FIG. 7I, robotic arm 115 is configured to include a reach, an upward-downward movement, a rotation, such as to move the arm in three dimensions. In some examples, robotic arm 115 is used to couple each conductor to a respective channel of conductor hub 270. In one example, robotic arm 115 may thread the conductor into a channel of conductor hub 270, such as shown in FIG. 6P. Robotic arm 115 may grasp the conductor, such as may extend from the bobbin of FIG. 6O, and guide the conductor to the channel of FIG. 6P, such as by using assembly apparatus 100. In the conceptual illustration of FIG. 7J, portions of assembly apparatus 100 are shown. Examples of robotic arm 115 may control one or more conductors, and position the conductors in desired locations. In other examples, a human operator may perform all or a portion of such functions. FIG. 7K includes another conceptual robotic arm 115 configured to operate as described with respect to FIG. 7I.

In some examples, the conductor hub fits the conductor pattern from the winder apparatus before the tension is released, such as to match to the conductor pattern to the conductor hub. A tool and technique may be used to move the wires into the conductor hub grooves before the tension is released. Once the conductor hub and presentation of conductors are captured, the tension or spring back may be allowed to happen.

Figure 10A:
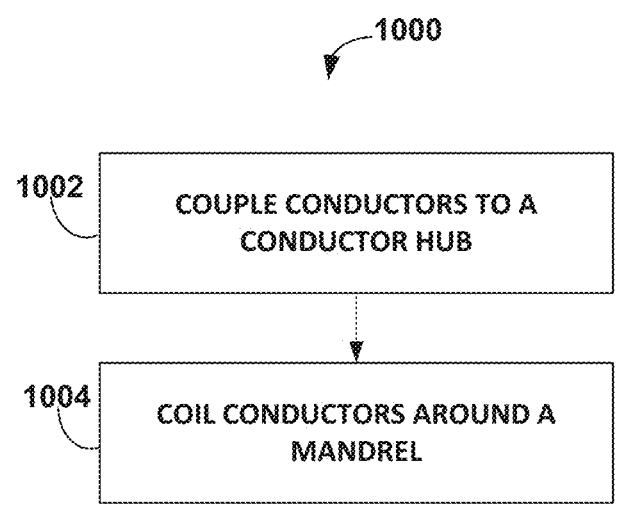
FIGS. 10A-B illustrate examples of a method for assembling a modular medical lead system.
Figure 10B:
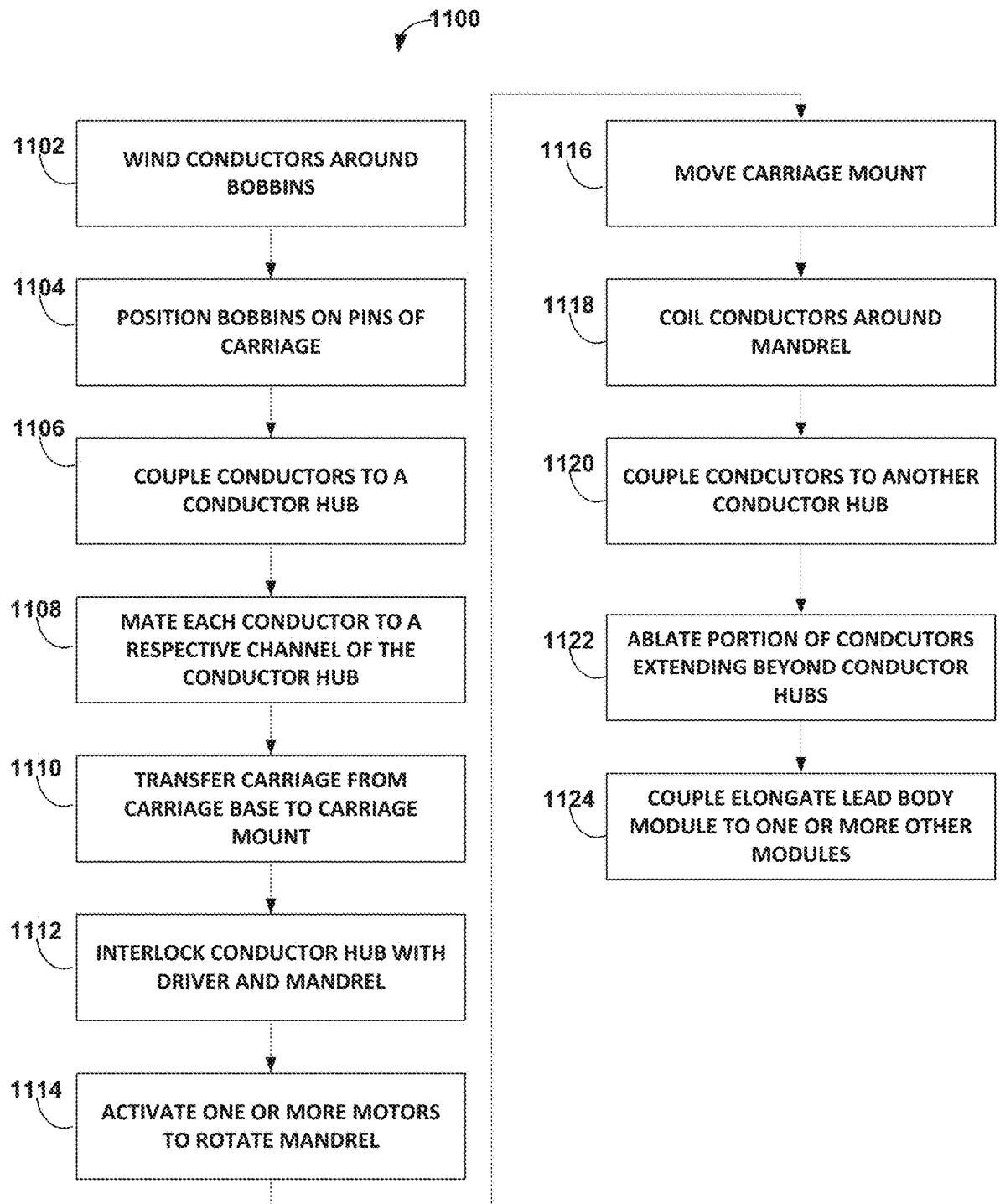

FIGS. 10A-B illustrate examples of a method for assembling a modular medical lead system. In the example of FIG. 10A, method 1000 is shown. At 1002, a plurality of conductors are coupled to a conductor hub. At 1004, the plurality of conductors are coiled around a mandrel, such as to form the coiled arrangement of elongate lead body module 52. Features or techniques described herein may be used for steps 1002 and 1004, such as one or more conductor hubs.

FIG. 10B illustrates an example of method 1100. Method 1100 may include one or more of the following steps, and the steps may be rearranged to manufacture, for example, elongate lead body module 52. At 1102, the plurality of conductors are wound around a respective plurality of bobbins 112. At 1104, the bobbins 112 are positioned on pins 113 of carriage 111. At 1106, each conductor may be mated to a respective channel of conductor hub 270. In some examples, at 1110, carriage 111 is transferred from base 114 to carriage mount 126. At 1112, conductor hub 270 may be interlocked with driver 121 and mandrel 124.

At 1114, one or more motors 125 may be activated, and the motors may rotate the mandrel 124, such as through a connection between the motor 125, the cone member 122, the driver 121 and the connector hub 270. At 1116, carriage mount 126 may be moved, such as by using another motor, such as described herein. While the carriage mount 126 moves away from conductor hub 270 and while mandrel rotates, at 1118 the conductors are coiled around mandrel 124. Conductor hub 270 maintains the arrangement of the conductors for winding the conductors around the mandrel. At 1120, the conductors are coupled to another conductor hub, such as the second conductor hub. In one example, this may include mating the conductors to channels of a stabilizer hub. In some examples, the conductors may be coupled to a finishing hub (e.g., the second conductor hub), and a subsequent step to secure the conductors to the finishing hub may include applying adhesive (e.g., glue) to secure the conductors to the second hub, applying heat to reflow material around the conductors, snap fitting the conductors to the channels, performing a short cleanup step, such as after applying a glue (e.g., to remove excess glue), or any combination thereof. In some examples, coupling the conductors to the conductor hub may include temporarily clamping the conductors in place with a clamp configured to fit around the conductor hub and conductors to secure the conductors in place, and such a clamp may be removed in subsequent steps. At 1122, portions of the conductors that extend beyond the conductor hub can be sized to a desired length and ablated, such as to remove an electrically insulating coating. At 1124, elongate lead body module is coupled to one or more other modules, such as to form modular medical lead system 50.

Method 1100 may include that two conductor hubs 270 are used, such as for a starting hub and a finishing hub. In some examples, conductors form a coiled arrangement after being coupled to conductor hub 270. In some examples, conductors are couple to conductor hub 270 after being formed into a coiled arrangement. In some examples, the conductors are fixed within the channels of conductor hub 270. In some examples, the conductors may slide or otherwise move within the channels as the conductor hub maintains the desired conductor arrangement provided by the distribution of channels. After forming elongate lead body 52, mandrel 124 may be pulled out of the space defined by the coiled arrangement, and may be pulled out through a central opening of conductor hub 270.

In some examples, the techniques and features herein may be combined with "hand winding" the conductors into the coiled arrangement. As such the conductor hub may aid in winding any coiled arrangement of conductors.

In some examples, at 1120, the order of the conductors may be captured, such as by sliding conductor hub over mandrel 124 (e.g., as in FIG. 5D). In some examples, conductors are pulled or advanced from the winder apparatus (e.g., the mandrel) to form a bend (e.g., as FIG. 5E). In some examples, conductors are locked, such as by adding a surrounding ring that may be pressed, snap-fit, staked with heat or mechanically, glued or molded to conductor hub 270 (e.g., as in FIG. 5F), such as may include ordering the conductors to be ready for final conductor distribution hub. In some examples, a relatively small spring-back unwind process may occur after the desired presentation of conductors is locked.

In some examples, at 1120, stabilizer hub may capture the distribution of conductors while on the mandrel. The stabilizer hub may keep conductors ordered and in a known position as part of the winding process to aid in position the conductors for final presentation. In some examples, final presentation may then be completed after winding, spring-back, and removal from the winder apparatus. The conductor hub may be slid into the elongate lead body module after winding. In some examples, conductor hub 270 may include a fingers shape that may act as a forming die as the conductors are pulled and locked into the grooves. In some examples, a stabilizer hub may include features to control the conductor forming transition from coil to desired presentation such as straight or helix. It may also have a feature to immobilize the coil transition area and protect it from being malformed during spring-back. In some examples, locking the transition area may be done by design variants of the conductor hub 270, such as may include tape, adding a split flexible surrounding ring, pressed, snap fit, staking with heat or mechanical, glued or molded (i.e. low temperature reflow). In some examples, the stabilizer hub may be used with other mechanisms to drive and control the unwinding (speed, amount, etc.) during the spring-back. In some examples, after winding the coiled arrangement a mesh stabilize feature with or without fingers may be coupled into winding pattern. The conductor may be advanced to mesh stabilize feature to form the conductor arrangement. In some examples, an interim lock and controlled spring-back may allow spring-back and then the conductors will be ready for final wire distribution.

Figure 8A:
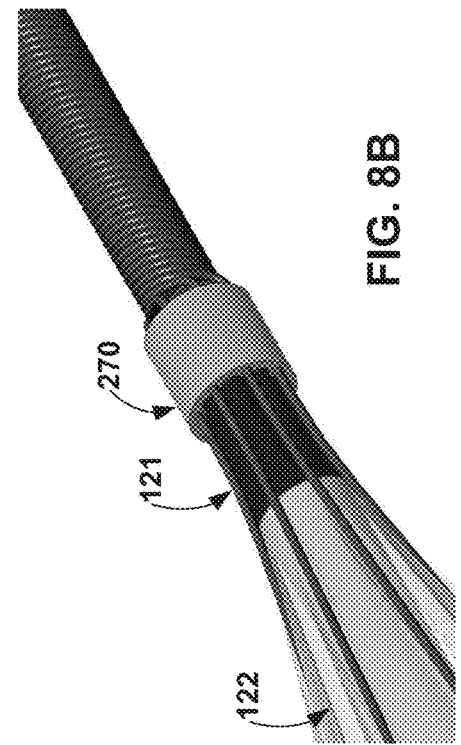
FIGS. 8A-H illustrate examples of a modular medical lead system.
Figure 8B:
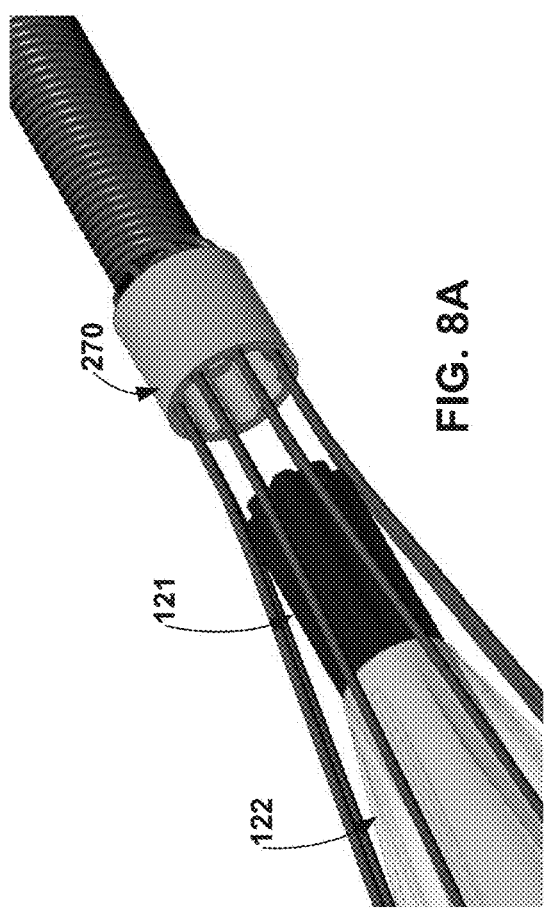

FIGS. 8A-H are conceptual diagrams illustrating example aspects of a modular medical lead and systems during the manufacture of such modular leads. In an example, cone member 122 may include channels (such as in the form of grooves as shown in the example of FIG. 8A), and conductors may extend from conductor hub 270, to be secured on cone member 122. Driver 121 may include channels, such as grooved channels. As can be seen from the transition from FIG. 8A to FIG. 8B, conductor hub 270 may be interlocked with driver 121. Conductor hub 270 may be interlocked with mandrel 124, such as before or after interlocking conductor hub 270 with driver 121. Likewise, this coupling may allow for ease of removal after elongate lead body 52 is formed. In the example of FIG. 8B, the conductors mate with the grooves of driver 121 and cone member 122. In some examples, the grooves of driver 121 and cone member 122 align with one another, such as to secure the ends of the conductors during the coil winding process.

Figure 8C:
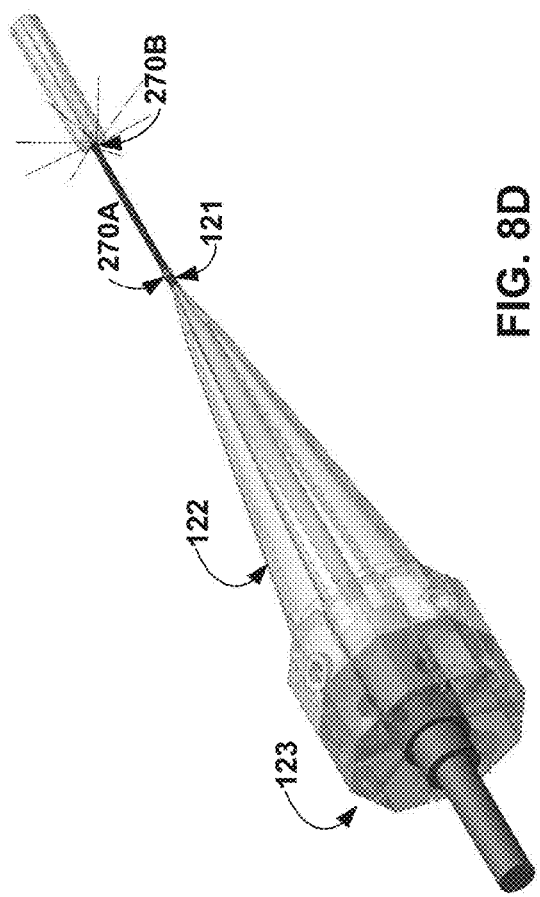
Figure 8D:
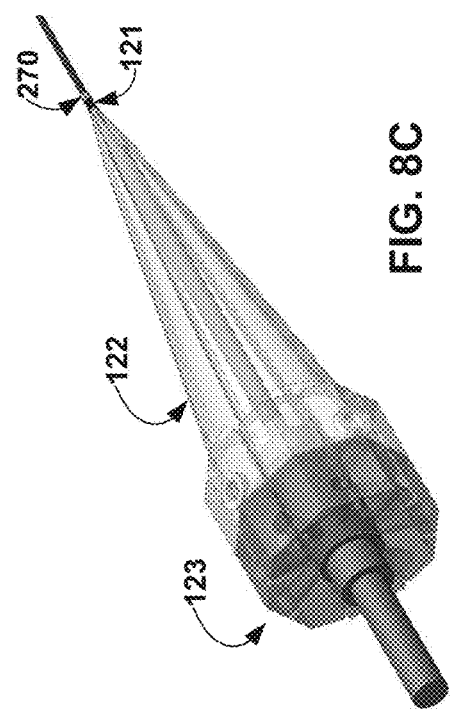

FIG. 8C illustrates a conceptual example of portions assembly system 100 and elongate lead body module 52 during the coiling process (also referred to as winding process). In the example of FIG. 8D, first conductor hub 270A may be coupled to driver 121. In an example, second conductor hub 270B is used to form the second end of elongate lead body module 52. For example, conductor hub 270B may be a stabilizer hub, a spiral hub, a hub having grooves, or another hub. In some examples, the excess lengths of conductors may be cut, and portions of the remaining conductors extending from the respective conductor hubs 270A and 270B may be ablated, such as to remove electrically insulating material.

Figure 8E:
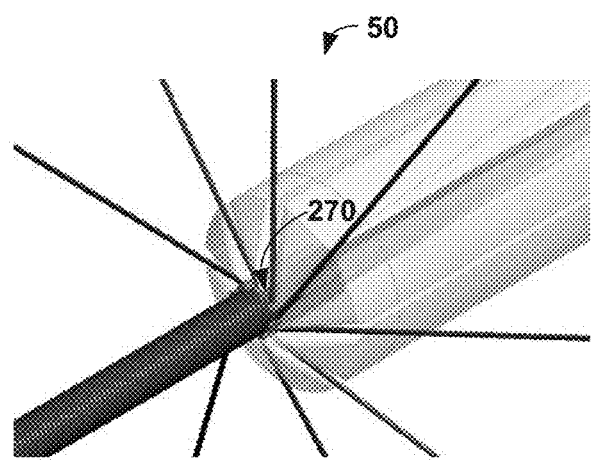
Figure 8F:
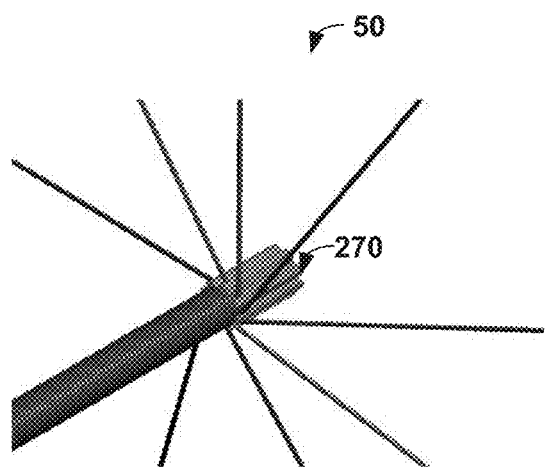
Figure 8G:
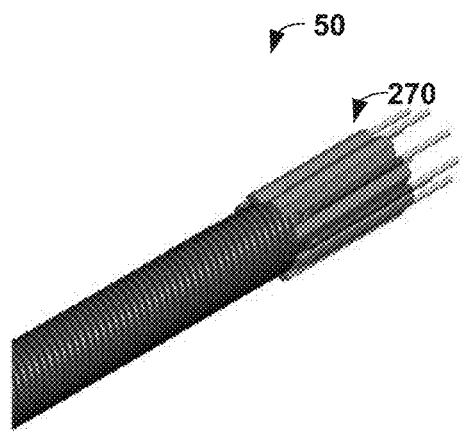
Figure 8H:
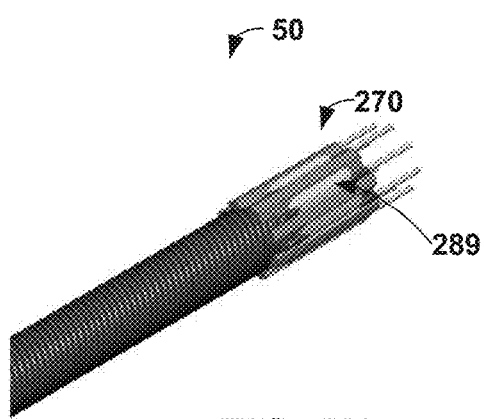

FIGS. 8E-H illustrate examples of the second conductor hub (e.g., also may be referred to as conductor hub 270, such as shown) toward the end of the winding process. The conductors may be organized using the fingers of the conductor hub. In the examples of FIGS. 8E and 8F, the conductors may be controlled using conductor hub 270, such as to maintain the coil formed during the winding process. In the examples of FIGS. 8G and 8H, conductor hub 270 may be configured to hold the conductors in place, as shown. In an example, a snap-member 289 may be coupled to each conductor, such as shown in FIG. 8H. The snap member 289 may be an adhesive or a plastic ring or cylinder, in some examples. The snap-member 289 may help secure the conductors within the grooves of the conductor hub, such as in FIG. 8H.

Figure 5H:
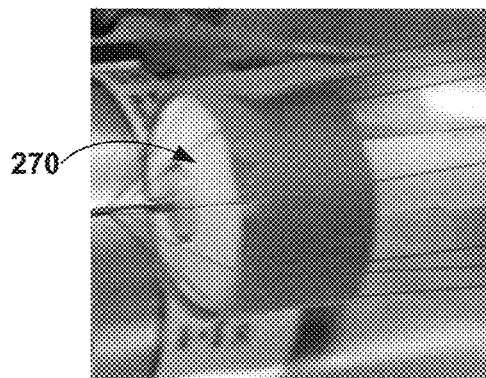
Figure 5J:
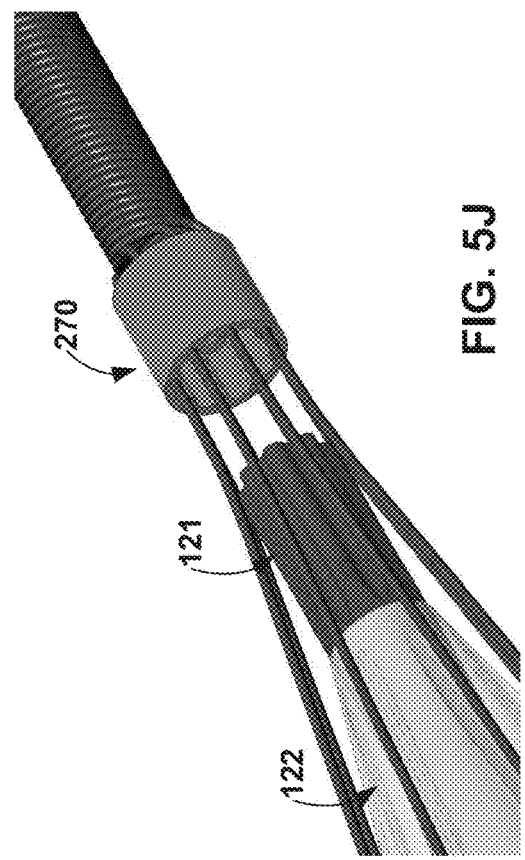
Figure 5L:
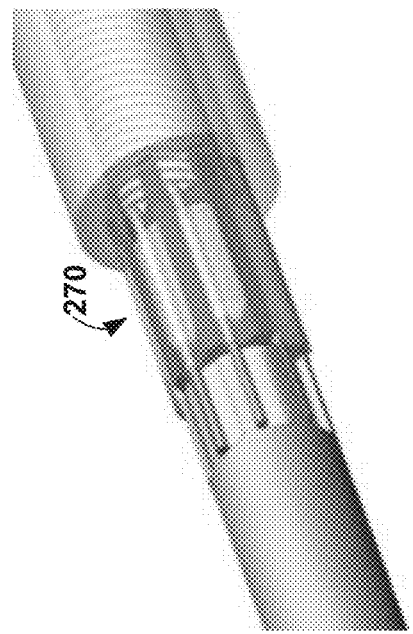
Figure 5I:
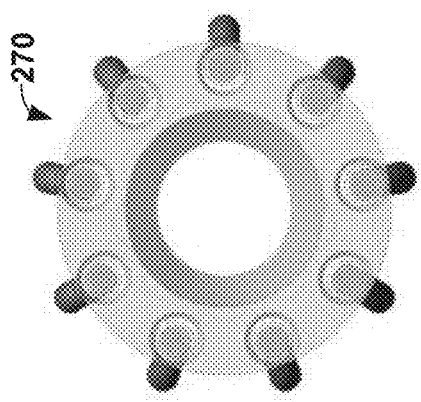
Figure 5K:
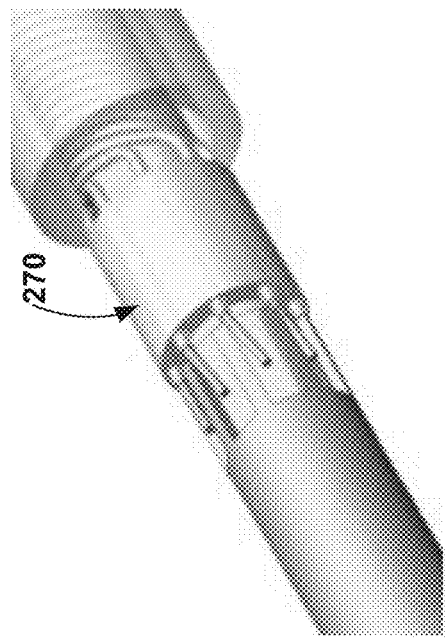
Figure 5N:
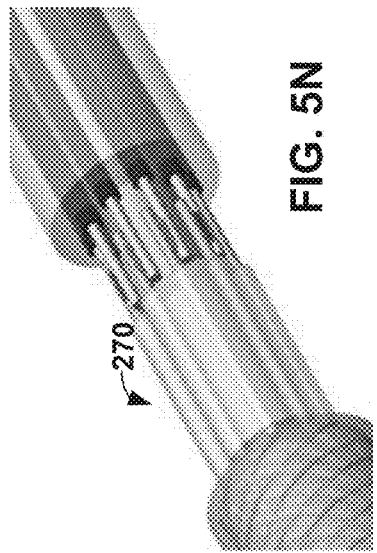
Figure 5Q:
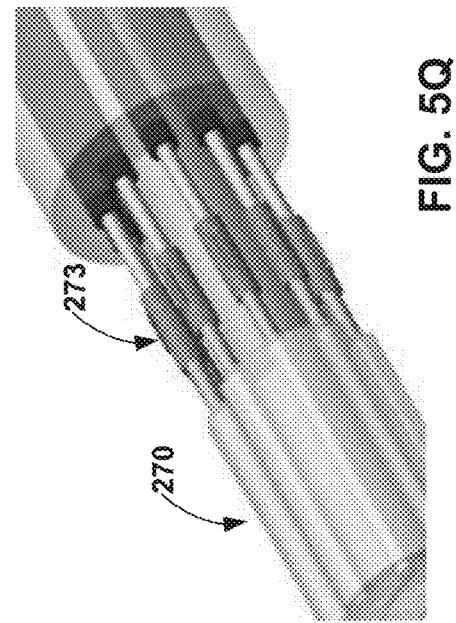

FIGS. 5A-Q illustrate examples of portions of a modular medical lead system. In some examples of FIGS. 5A-Q, there are different designs of conductor hub 270. In an example, conductor hub 270 includes a plurality of channels 283 (only a single channel is labeled) extending between a first end 281 and a second end 282 of conductor hub 270, such as may be seen in FIG. 5A. In the example of FIG. 5A, each channel 283 is a through-hole type channel or conduit. Each channel 283 may correspond to a conductor of the elongate lead body module 52. The conductor may be fixed in place within the channel 283. Or in some examples, the conductor is movably coupled to conductor hub 270, such that the conductor may slide relative to the conductor hub.

In the example of FIG. 5B, conductor hub 270 include channels 283 that are grooved or recessed as compared to forming a closed channel as in FIG. 5A. To lock or otherwise fix the conductors within channels 283 of hub 270 in an arrangement, design variants may include adding a surrounding ring or tape, which may be pressed, snap-fit, staked with heat or mechanically staked, glued, or molded (e.g., such as with a low temperature reflow). In some examples conductors of the elongate lead body module are coupled to another module past conductor hub 270. In other examples, conductors of the elongate lead body module are coupled to respective conductors of another module within a length of the grooved channels, such as by welding or other coupling.

In the example of FIG. 5C, conductor hub 270 includes grooved channels 283 that are spiraled around conductor hub 270, e.g., as opposed to substantially straight configuration between ends 281 and 282 for hub 270 shown in FIG. 5A. In some examples, a density of the spirals (e.g., rotations per length) is less than that of the coiled arrangement of conductors of elongate lead body module 52. In some examples, the density of the spiral is substantially similar to or less than that of the coiled arrangement.

In the examples of FIGS. 5D-F, conductor hub 270 includes grooved channels 283 (individual channel 283 labelled in FIG. 5D). In these examples, conductor hub 270 may be used as a conductor distribution hub for coil winding, e.g., during the manufacturing process of lead body module 52. In an example, conductor hub 270 with grooved channels (also referred to as "grooves") may include extensions 284 (or "fingers 284") to capture and lock conductors, such as to provide a specified presentation (or arrangement) while the conductors are ordered (such as on a winding head during manufacture). In some examples, the shape of fingers 284 act as a forming die, such as when the individual conductors are pulled and locked into the grooves 283. In some examples, to lock the conductors in an arrangement, design variants may include adding a surrounding ring, which may be pressed, snap-fit, staked with heat or mechanically staked, glued, or molded (e.g., such as with a low temperature reflow). In an example, such a process includes, after winding the conductors in the coiled arrangement, the conductors may be advanced straight to mesh into the grooves, locked into position, and may allow for a spring-back due to the coil. In some examples, conductor hub 270 may not include protrusions 284 (or fingers 284), such as for ease of manufacturing. In some examples, the grooves may bow, such as to bend conductors within the grooves. The grooves and the edges of conductor hub 270 (such as at first and second ends 281, 282), may be used to form (e.g., bend) the conductors. In some examples, conductor hub 270 is used as an assembly tool, and removed after the desired presentation of the conductors is locked or secured.

In some examples, a conductor arrangement includes a straight arrangement, such as past conductor hub 270. In some examples, a conductor arrangement includes a helix. Other arrangements past the first end 281 or the second end 282 of conductor hub 270 may be used. Conductor hub 270 may be used to capture or secure conductors during the coiling process of elongate lead body module 52. As such, conductor hub may assure the presentation of the conductors before spring-back (e.g., unwind) effect occurs. In some examples, conductor hub 270 forms wires during or after winding in short transition and diameters beyond 'bending' (yield).

In the example of FIG. 5D, conductor hub 270 may capture an order of the conductors from a winder apparatus. Conductor hub 270 may slide over a mandrel of the winder apparatus and into position next to the coiled arrangement, such as to secure the conductors. Conductor hub 270 may include the finger shape to provide a forming die, such as for finishing the winding process of the elongate lead body module.

In the example of FIG. 5E, conductors may be pulled or advanced from the winder apparatus to form a bend over conductor hub 270. In some examples, conductors may be pulled or advanced from the winder apparatus to form a bend without conductor hub 270, such as by bending the conductors themselves.

In the example of FIG. 5F, conductor hub 270 includes a lock feature. In some examples, conductors may be secured to conductor hub 270, such as by adding a surrounding ring or tape, by pressing the conductors into place within grooves, by snap-fitting the conductors within grooves, by staking with heat or staking mechanically, or glued or molded. In an example, once the conductors are secured, the conductors may be ordered and ready to be coupled to another wire distribution hub, or another module. A spring-back unwinding process may occur after the desired presentation is locked or secured.

In the example of FIG. 5H, conductor hub 270 may comprise a stabilizer hub. In an example, the stabilizer hub may include fingers to help in capturing the wire distribution on a winder. In an example, the fingers shape may act as a forming die as the wires are pulled and locked into the grooves. In an example, the fingers may protect the transition area from unwanted bends during the spring-back unwind process, such as may be a feature to immobilize the conductors in the coiled arrangement. In an example, the stabilizer hub may include features to control the wire forming transition from coil to desired presentation such as straight or helix. In an example, securing the transition area may be done by design variants such as may include taping, adding a split flexible surrounding ring, or other techniques described herein. In another example, the stabilizer may be used with other techniques or features to drive and control the unwinding (speed, amount, etc.) during the spring-back. In an example, conductor hub 270 may include lengthwise support for wires used in next wire manufacturing process.

In the example of FIG. 5I, conductor hub 270 is illustrated in a side view. Conductor hub 270 may include a through-hole extending from the first end to the second end of conductor hub 270. The plurality of wires may form an arrangement, such as may include having a diameter greater than the diameter of conductor hub 270.

In the example of FIG. 5J, conductor hub 270 includes an internal drive feature. A driver 121 of winder apparatus 120 may be inserted inside the internal drive feature, such as to couple conductor hub 270 to the motor of winder apparatus 120. Driver 121 may be coupled to a cone member 122 of winder apparatus 120. In one example, cone member is a part of a winding head that may include the motor, such as to couple the motor to the conductor hub 270. In another example, a mandrel of winder apparatus 120 (not shown) may be coupled on the opposite end of conductor hub 270 as driver 121, such that when the motor is activated, conductors may be wound around the mandrel as the motor rotates conductor hub 270.

In the example of FIG. 5K, conductor hub 270 is illustrated with conductors extending past its end, such as in an angled arrangement, such as to couple the conductors to respective portions of another module.

Figure 5O:
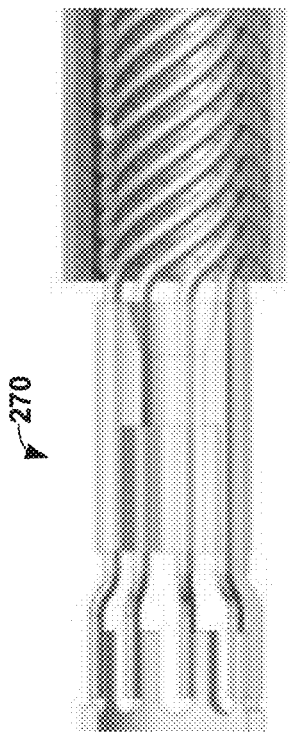

In the example of FIG. 5L, conductor hub 270 is illustrated with conductors extending past its end, such as in a straight arrangement, such as to couple the conductors to respective portions of another module. In the example of FIG. 5L, the portions of the conductors that extend past conductor hub 270 are shown as coupling to a lead end module in a side-by-side arrangement. For example, the conductors of extending out of conductor hub 270 may be positioned in the same radial layer of the lead as the conductors of the lead end module. In some examples, the conductors that extend out of conductor hub 270 may be in an over-under arrangement with another module. FIG. 5T illustrates a top view of a conceptual example of a conductor and an electrode in such an over-under arrangement, as further described below. For example, the conductors extending out of conductor hub 270 may be positioned at a larger radius than the conductors or connection contacts of the lead end module. In an example, the conductors extending out of conductor hub 270 may be positioned at a smaller radius than the conductors of the lead end module. In an example, during assembly, using the over-under arrangement may allow for pushing the conductors into contact, which may make angular orientation positioning of the modules easier.

Figure 5M:
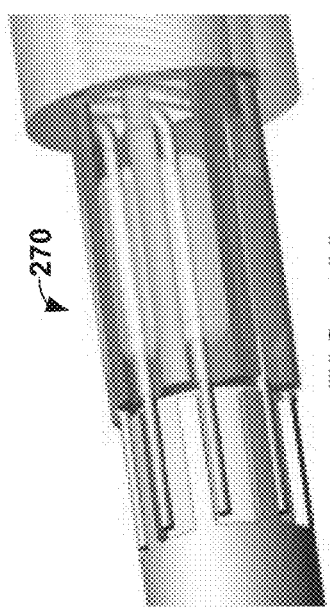

In the example of FIG. 5M, conductor hub 270 is illustrated with conductors extending past its end, such as in a straight arrangement, such as to couple the conductors to respective portions of another module. In this example, a snap-fit feature may be within grooves of conductor hub 270.

In the example of FIG. 5N, conductor hub 270 is illustrated with conductors extending past its end, such as in a straight arrangement, such as to couple the conductors to respective conductors of another module.

In the example of FIG. 5O, conductor hub 270 is illustrated with conductors extending past its end, such as in a circular arrangement, where the circular arrangement has a greater diameter than a diameter of the channels of conductor hub 270.

Figure 5P:
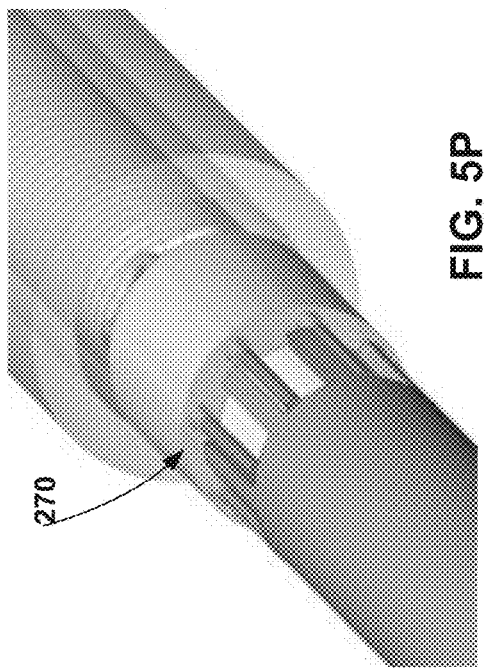

In the example of FIG. 5P, conductor hub 270 is illustrated with conductors extending past its end, such as in a straight arrangement, such as to couple the conductors to respective conductors of another module.

In the example of FIG. 5Q, conductor hub 270 is illustrated with conductors extending past its end, such as in a straight arrangement, such as to couple the conductors to respective conductors of another module. In this example, conductor connectors 273 may be used to couple conductors of different modules to each other. This connection may include a welded connection. In some examples, the connection is a mechanical connection, such as by mechanically mating the conductors to each other.

Figure 5R:
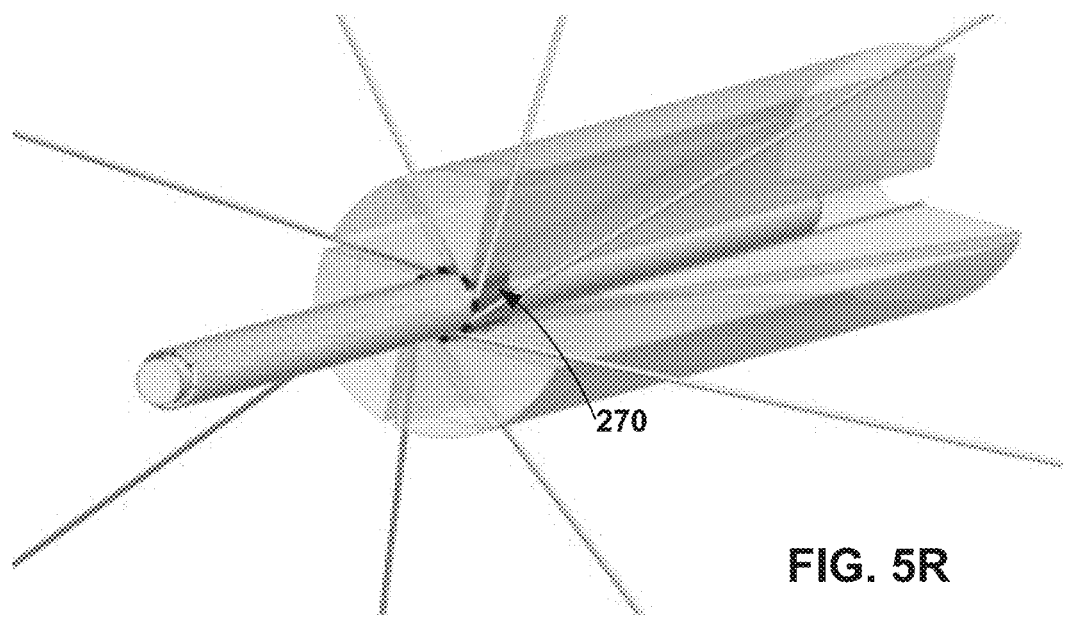
Figure 5S:
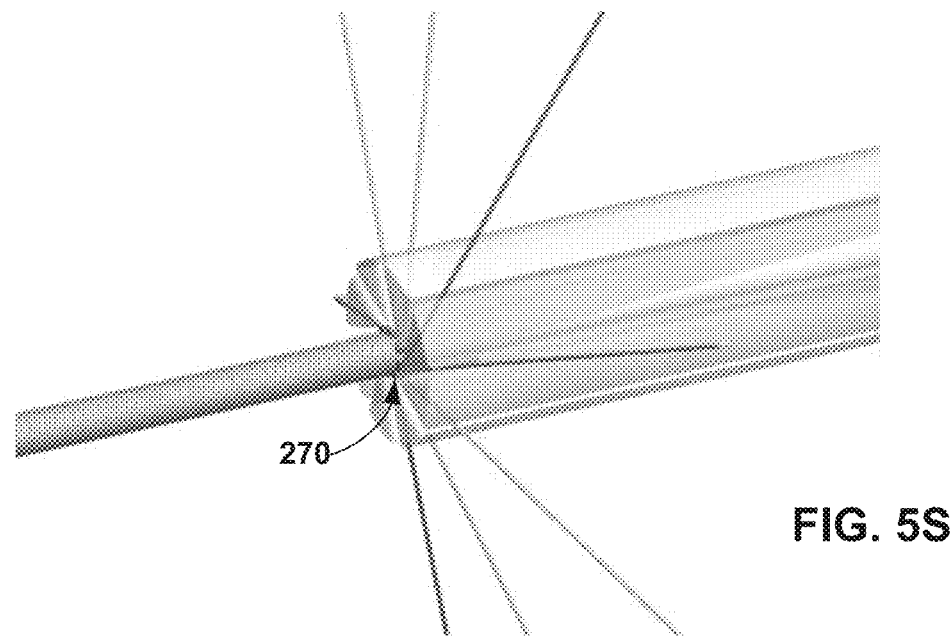
Figure 5T:

In the examples of FIGS. 5R and 5S, conductor hub 270 may be grooved. Conductor hub 270 may include an interlocking hub that may mate with the conductors on the winder apparatus, such as at an end of the wind length (e.g., the end of the coiled arrangement). FIG. 5R shows a portion of hub 270 removed to illustrate the mating the mandrel about a center aperture in hub 270. A tool may be used to assist the conductor hub to interlock with the winder apparatus, and provide assistance to mate with other components of the assembly system. Conductor hub 270 may capture conductors before spring-back, such as to stabilize the terminating end of the coiled arrangement. As such, in an example, the conductors may not move after spring-back (e.g., the coiled arrangement is substantially secured after the initial spring-back). In one example, while the conductors are under tension, the tool may mesh the conductor hub into the coiled arrangement from the winder apparatus.

In the examples of FIGS. 5A-Q, conductor hub 270 may include an internal drive feature or an external drive feature, such as for use as a starting hub when winding the coil around a mandrel. In these examples, conductor hub 270 may include an implant stylet lumen feature, such as an opening defined by a body of conductor hub 270. The opening of conductor hub 270 may extend partially or fully through a length of conductor hub 270. In an example, conductor hub 270 fits conductors or crimped conductors. In an example, conductor hub 270 is machined. In an example, conductor hub 270 is extruded. In an example, conductor hub 270 is rigid. In an example, conductor hub 270 is elastomeric. In an example, conductor hub 270 is a separate component from elongate lead body module 52. In an example, conductor hub 270 is molded in place, such as starting mold hub or finishing mold hub, such as during the manufacture of elongate lead body module 52.

Figure 5U:
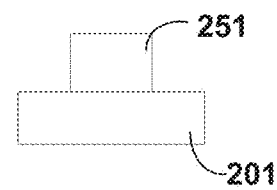

In the example, of FIG. 5T, conductor 251 is positioned over electrode 201 in the over-under arrangement (e.g., presentation) described herein. Although conductor 251 is shown as having a smaller cross-sectional dimension (e.g., diameter) than a width of electrode 201, any dimension for the electrodes (e.g., electrode 201) or conductors (e.g., conductor 251) described herein may be used. In some examples, an electrical contact of a lead-end module may be over the conductor of the lead module 50. FIG. 5U is an end view of the example over-under arrangement of conductor 251 and electrode 201 of FIG. 5T. Although illustrated as a rectangle, conductor 251 may generally have a round cross-section.

In some examples, conductor hub 270 may stabilize or register conductors so that the conductors are in a precise, known position. In these examples, conductor hub 270 may be configured to allow conductors to extend from conductor hub 270 in straight or angled arrangements. In these examples, conductors may be expanded, such that a diameter of the arrangement of the conductors is larger than a diameter of a medial portion of the elongate lead body module. Or, in these examples, an arrangement of the conductors extending form conductor hub 270 has a substantially similar shape (e.g., diameter) as the medial portion of the elongate lead body module.

Conductor hub 270 may assist in coil winding termination, such as in a stable, precise, and registered presentation. Channels of conductor hub 270 may include through-hole, grooved, straight, angled, helical, locking, press or snap fit, other types of channels. Conductors may be coupled to conductor hub 270, such as by locking the transition area with tape or another adhesive system. In some examples, a split flexible surrounding ring is coupled to a termination end of the elongate lead body module during winding of conductors (e.g., such as by surrounding conductor hub 270 or directly onto the conductors).

In some examples, conductor hub 270 may be interlocked with the mandrel of the winder apparatus, such as during the manufacture of elongate lead body module 52. In an example, conductor hub 270 captures the arrangement (e.g., the order) of the plurality of conductors before the winding process begins. As such, conductor hub 270 may allow for automation and mechanized assembly of modular medical lead system 50. In one example this includes an automated robotic arm configured to couple the plurality of conductors from bobbins at an assembly apparatus to conductor hub 270, such as at a respective plurality of channels of conductor hub 270. In an example, a desired conductor arrangement is formed immediately adjacent to conductor hub 270, such as by using the techniques and features disclosed herein. In an example, by using the techniques and features herein (e.g., such as conductor hub 270), during the manufacture of elongate lead body module 52, irregular or long transition sections may be reduced, such as relative to conventional lead manufacturing processes.

In some examples, the stabilizer hub may be installed before allowing spring-back. In some examples, the stabilizer hub maintains the order or arrangement of the conductors (e.g., a wound coil assembly of the elongate lead body module). In yet other examples, the techniques and features disclosed herein allows the transfer or ordered conductor arrangement to termination of winding and presentation of an end portion of the conductors.

Figure 11A:
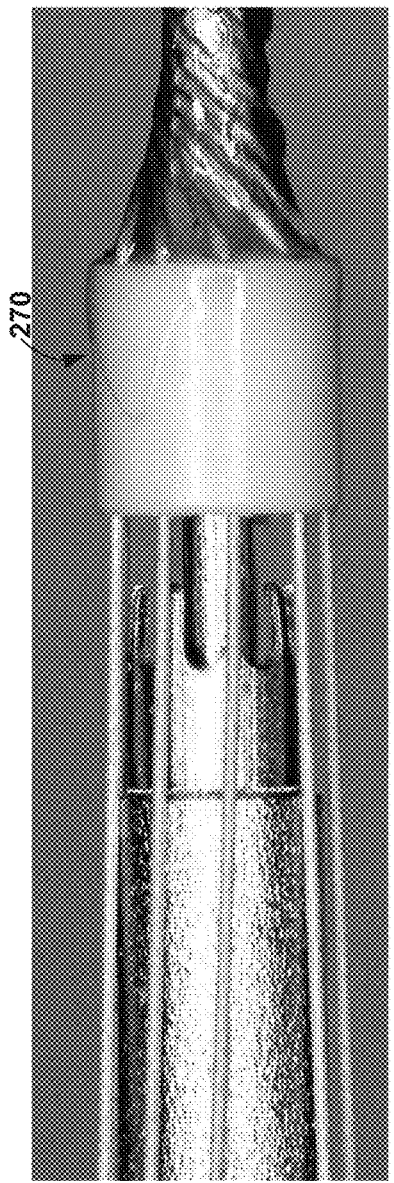
FIGS. 11A-11I illustrate examples of a modular medical lead system.
Figure 11B:
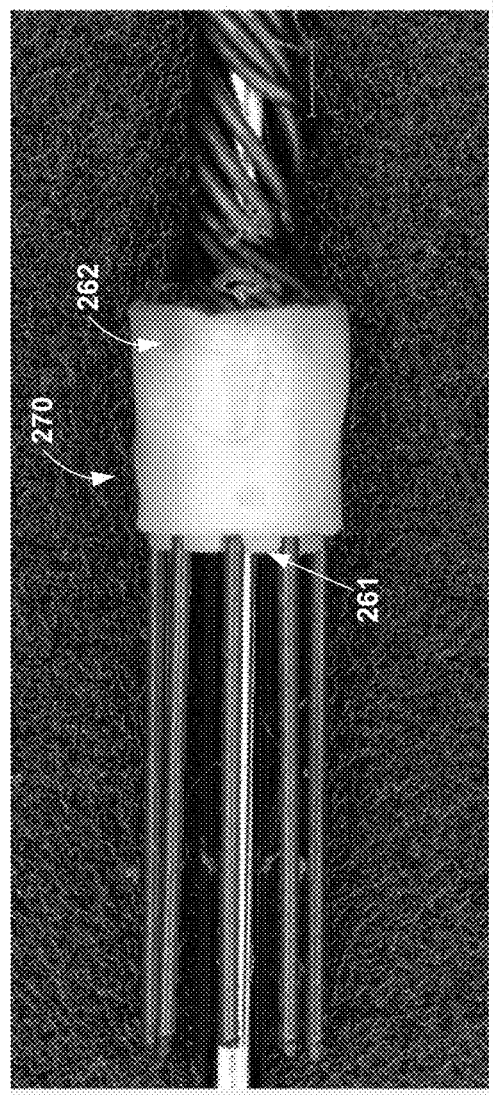
Figure 11C:
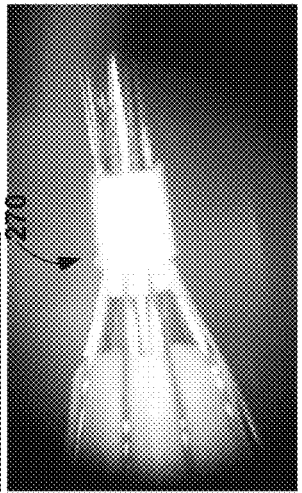
Figure 11D:
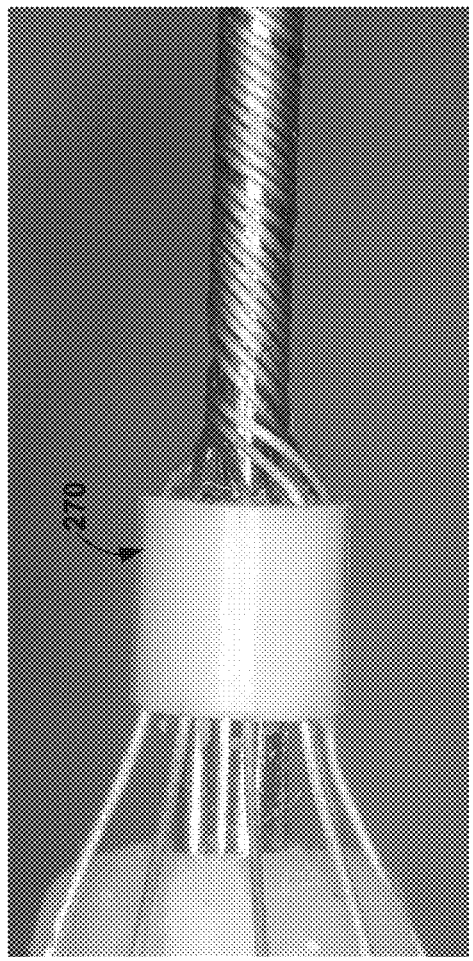
Figure 11F:
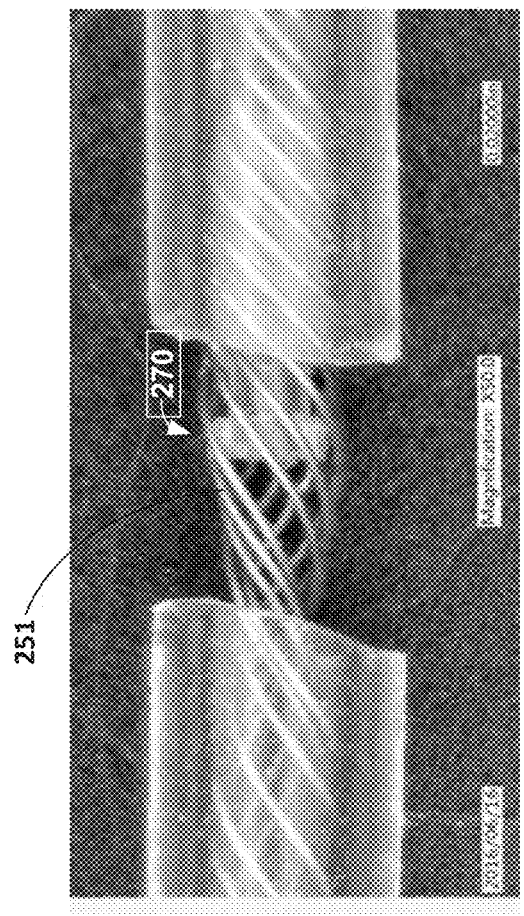
Figure 11E:
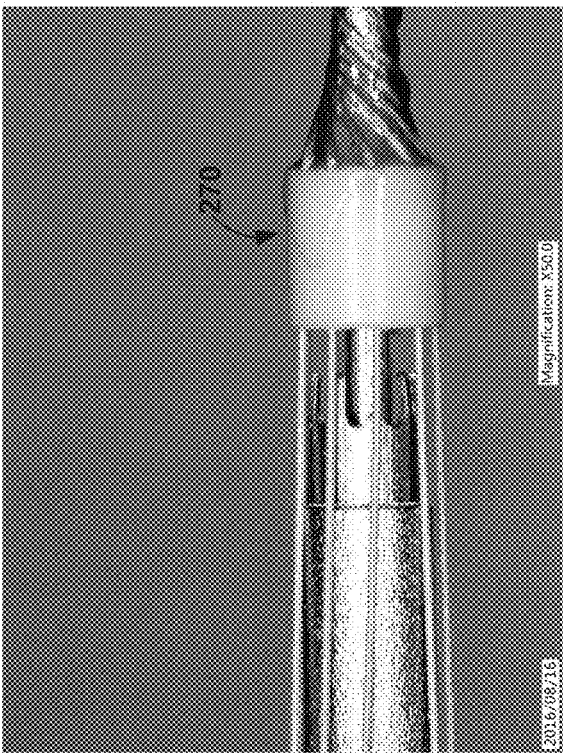
Figure 11H:
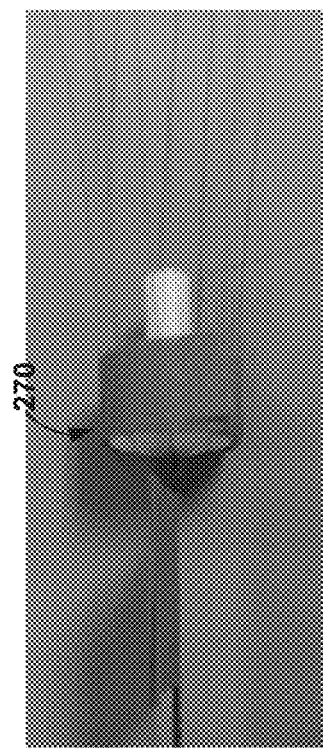
Figure 11G:
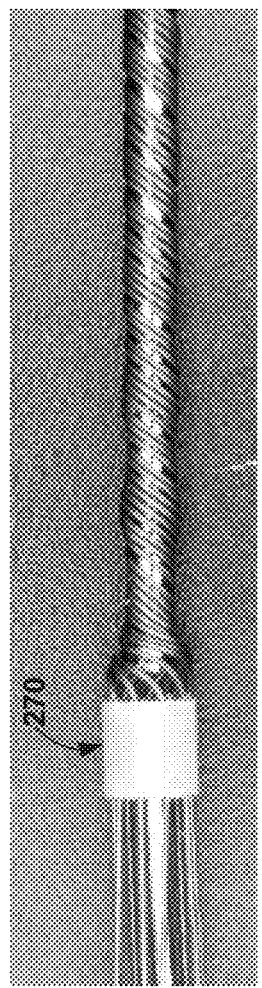
Figure 11I:
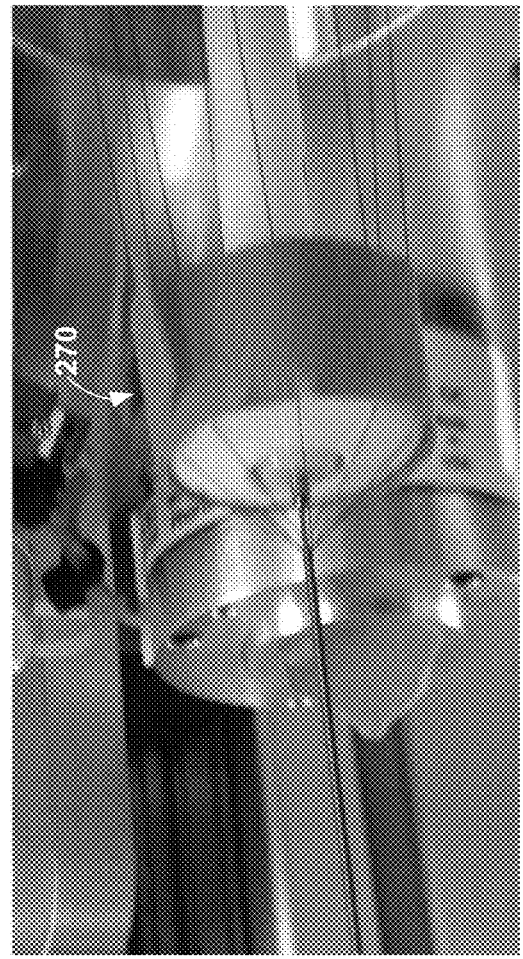
Figure 12A:
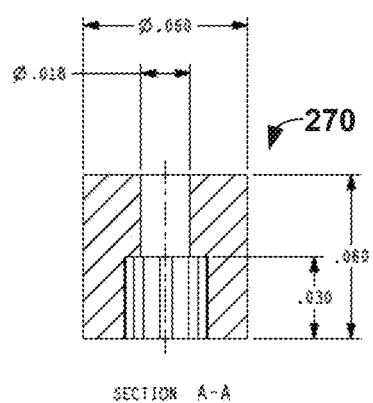
FIGS. 12A-H illustrate examples of a conductor hub.
Figure 12B:
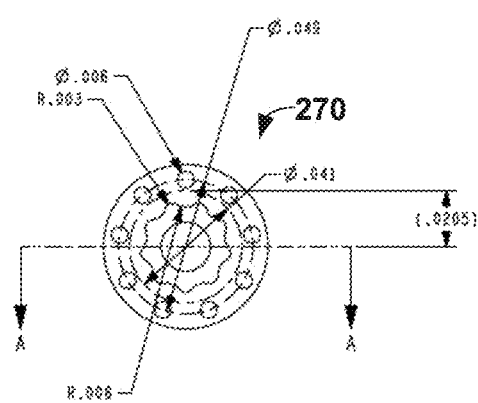
Figure 12C:
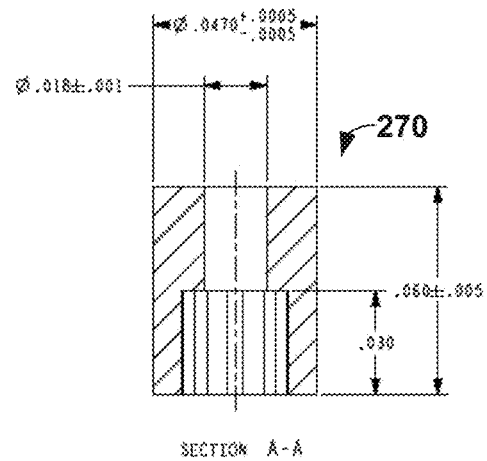
Figure 12D:
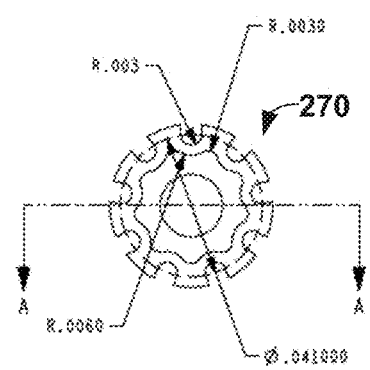
Figure 12E:
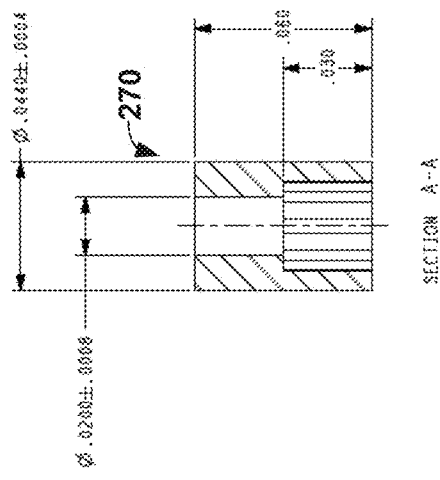
Figure 12F:
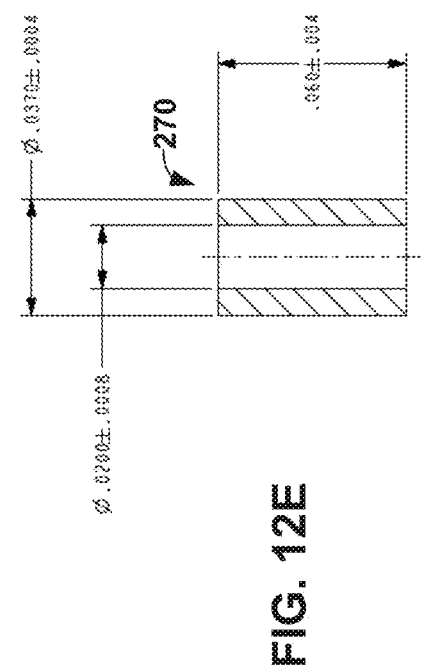
Figure 12G:
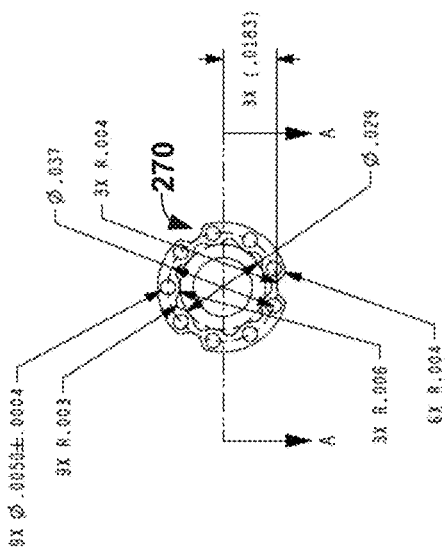
Figure 12H:
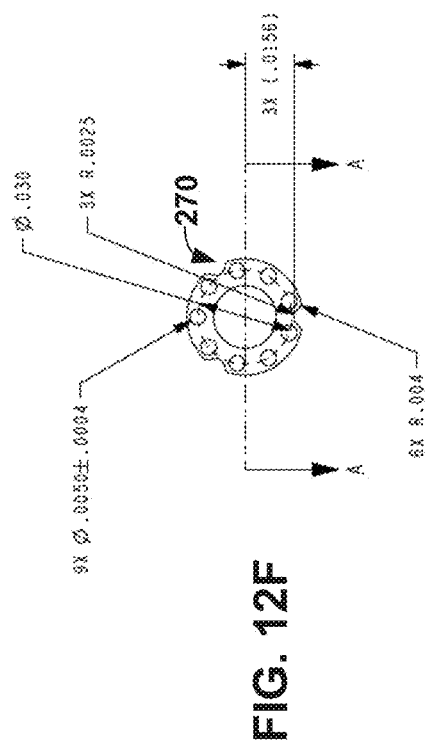

FIGS. 11A-11I illustrate examples of modular medical lead system 50. FIGS. 11A-11G show examples of an enlarged view (e.g., taken with a zoom camera) of conductor hub 270. FIGS. 11H-11I are examples of a stabilizer hub. For example, FIGS. 11A, 11B, 11D, and 11E each illustrate an enlarged view of conductor hub 270. Conductors extend from the conductor hub 270. In some examples, such as shown in FIG. 11B, conductor hub 270 may comprise more than one structure. In the example of FIG. 11B, conductor hub 270 may comprise a hub body component 261 and a hub sleeve component 262. For example, hub sleeve component 262 may be positioned over hub body component 261 to secure the conductors in place, such as before or after winding as described herein. In an example hub sleeve component 262 may be heat shrunk over hub body component 261. In some examples, hub sleeve component 262 may comprise an elastic material, such as may be stretched over hub body component 261 and released to tightly secure the conductors into place. In some examples, tape may be wound around stabilizer hub to secure the conductors. Any step herein may be performed either by automation or not by automation. For example, portions of method 1100 may be done by hand, such as by a human operator. In the example of FIG. 11F, conductor hub 270 is shown with conductors (e.g., conductor 251) in a coiled configuration.

FIGS. 12A-12H illustrate examples of conductor hub 270. In the examples of FIGS. 12A-12D, conductor hub 270 is diagrammatically illustrated with dimensions having illustrated values. Each of the examples of FIGS. 12A-12H include example dimensions that may be used for conductor hub 270. In examples of FIGS. 12A-12H, conductor hub 270 includes an internal drive feature (e.g., a component of conductor hub 270 having an aperture, such as described with respect to FIG. 5R), such as to couple to driver 121. In the examples of FIGS. 12E-12H, an external driver 121 may be used.

In some examples, a length of the elongate lead body module may include about 8 inches to about 36 inches. In some examples, the one or more conductors are coiled for a length between the second end of the first conductor hub and the first end of the second conductor hub, and wherein the length is about 1 inch to about 50 inches, about 6 inches to about 31 inches, or about 6 inches to about 36 inches. Other lengths are contemplated. In some examples, elongate lead body module 52 may be used for different purposes, such as for one or more different electrode arrangements on different electrode modules. A stylet may be positioned inside elongate lead body 52.

While many of the foregoing examples consider use of multiple conductors within the elongate body, it will be understood that techniques according to this disclosure apply with an elongate body having a single conductor. Also, while many of the examples consider an implantable lead or lead extension, these techniques apply to a module design for a medical system having one or more conductors carried by an elongate body, with one or more ends of the one or more conductors being electrically isolated from any other of the one or more conductors and mechanically coupled to the conductor hub such that the one or more conductors are in a fixed arrangement. These one or more conductors may be coupled to any type of end module, such as an end module for delivering electrical, optical, magnetic, chemical, or other type of therapy, for providing optical, electrical or any other type of monitoring, for providing electrical and/or mechanical connectivity, or any other type of end module.

In some examples, a number of conductors may be different than a number of channels in the conductor hub. For example, a modular medical lead system may include 8 conductors, and one or more conductor hubs may include 9 channels each. In some examples, two conductor hubs of a modular medical lead system include different numbers of channels (e.g., such as 8 channels in the first, and 9 channels in the second).

In some examples, at least one end of the conductor hub includes a smaller outer diameter than an inner diameter of the outer jacket (e.g., a jacket module).

The above features and techniques are examples. Any suitable techniques may be used to fabricate the structures described herein and may vary based on the particular materials employed for the respective components.

The above detailed description includes references to the accompanying drawings, which form a part of the detailed description. The drawings show, by way of illustration, specific embodiments of the disclosure be practiced. These embodiments are also referred to herein as "examples." Such examples may include elements in addition to those shown or described. However, the present inventors also contemplate examples in which only those elements shown or described are provided.

Clause 1: In one example, a modular medical lead system includes an elongate lead body module including a plurality of coiled electrical conductors extending from a first end to a second end of the elongate lead body module, and a conductor hub adjacent the first end of the elongate lead body module. The plurality of conductors are electrically isolated from one another and mechanically coupled to the conductor hub such that the plurality of conductors are in a fixed arrangement relative one another. A first end of the conductor hub is nearer the first end of the elongate lead body module than a second end of the conductor hub. Each of the plurality of conductors extend from the first end to the second end of the conductor hub relative a longitudinal axis of the elongate lead body module such that a portion of the conductors extend beyond the first end of the conductor hub, and wherein, for each conductor, the portion of the conductor that extends beyond the first end of the conductor hub is configured to be coupled to a respective electrical conductor of a lead end module to allow respective electrical signals to be conducted between the respective conductors of the lead end module and the conductors of the elongate lead body module.

Clause 2: In some examples of the modular medical lead system of clause 1, the conductor hub comprises a first conductor hub, the elongate lead body module further comprising a second conductor hub adjacent the second end of the elongate lead body, wherein the plurality of conductors are electrically isolated from one another and mechanically coupled to the second conductor hub such that the plurality of conductors are in a fixed arrangement relative to one another, wherein a second end of the second conductor hub is nearer the second end of the elongate lead body module than a first end of the second conductor hub, and wherein the plurality of conductors extend from the first end to the second end of the second conductor hub relative to the longitudinal axis of the elongate lead body module.

Clause 3: In some examples of the modular medical lead system of clause 2, each of the plurality of conductors extend from the first end to the second end of the second conductor hub such that a second portion of the conductors extend beyond the second end of the second conductor hub.

Clause 4: In some examples of the modular medical lead system of clause 3, the modular medical lead system further comprises another lead end module, wherein, for each conductor, the second portion of the plurality of conductors that extend beyond the second end of the second conductor hub is coupled to a respective electrical conductor of the another lead end module to allow the electrical signals to be conducted between the respective electrical conductor of the another lead end module and the conductor of the elongate lead body module.

Clause 5: In some examples of the modular medical lead system of any of clauses 1-4, the conductor hub includes a plurality of channels extending between the first end and the second of the conductor hub, wherein, each conductor is configured to mate with a corresponding channel of the plurality of channels of the conductor hub.

Clause 6: In some examples of the modular medical lead system of clause 5, the plurality of channels comprises at least one through-hole extending from the first end of the conductor hub to the second end of the conductor hub.

Clause 7: In some examples of the modular medical lead system of clause 5 or 6, the plurality of channels comprises at least one groove into an outer surface of the conductor hub from first end of the conductor hub to the second end of the conductor hub.

Clause 8: In some examples of the modular medical lead system of any of clauses 5-7, the plurality of channels includes 8 channels to 16 channels.

Clause 9: In some examples of the modular medical lead system of any of clauses 5-8, a total number of channels of the conductor hub is equal to a total number of conductors of the plurality of coiled electrical conductors.

Clause 10: In some examples of the modular medical lead system of any of clauses 1-9, the conductor hub exhibits an annular cross section along a plane substantially orthogonal to the longitudinal axis of the elongate lead body module.

Clause 11: In some examples of the modular medical lead system of clause 10, an outer diameter of the annular cross section is smaller than an outer diameter defined by the plurality of channels.

Clause 12: In some examples of the modular medical lead system of any of clauses 1-11, the plurality of conductors are arranged substantially circumferentially equidistant from one another around the conductor hub.

Clause 13: In some examples of the modular medical lead system of any of clauses 1-12, the plurality of conductors extend from the first end to the second end of the conductor hub in a direction substantially parallel to the longitudinal axis of the elongate lead body module.

Clause 14: In some examples of the modular medical lead system of any of clauses 1-13, the portion of the plurality of conductors that extend beyond the first end extend in a direction relative to the longitudinal axis of the elongate lead body module.

Clause 15: In some examples of the modular medical lead system of clause 14, the direction relative to the longitudinal axis is a non-zero angle relative to the longitudinal axis.

Clause 16: In some examples of the modular medical lead system of clause 14 or 15, the direction relative to the longitudinal axis is substantially parallel to the longitudinal axis.

Clause 17: In some examples of the modular medical lead system of any of clauses 1-16, the plurality of coiled conductors in the elongate portion define an inner lumen, and wherein the conductor hub includes an aperture that is aligned substantially co-axially with the inner lumen.

Clause 18: In some examples of the modular medical lead system of any of clauses 1-17, each conductor comprises a single conductive filament.

Clause 19: In some examples of the modular medical lead system of any of clauses 1-18, at least one of the plurality of conductors comprises a cable, wherein the cable includes more than one conductive filar.

Clause 20: In some examples of the modular medical lead system of any of clauses 1-19, an outer jacket covering the plurality of coiled conductors and the conductor hub of the elongate lead body module, and wherein the jacket is comprised of an electrically non-conducting material, and wherein the jacket is biocompatible.

Clause 21: In some examples of the modular medical lead system of any of clauses 1-20, the first end of the conductor hub has a different outer diameter than the second end of the conductor hub.

Clause 22: In some examples of the modular medical lead system of any of clauses 1-21, the through-hole of the hub body includes a portion with an increasing diameter, wherein the diameter of the portion with the increasing diameter increases from a distal fiducial relative to the proximal end of the hub body toward the proximal end of the hub body.

Clause 23: In some examples of the modular medical lead system of any of clauses 1-22, the plurality of conductors extend out the distal end of the hub body in a distal arrangement.

Clause 24: In some examples of the modular medical lead system of clause 23, the distal arrangement is a substantially circular shape.

Clause 25: In some examples of the modular medical lead system of clause 24, the substantially circular shape includes a radius smaller than the common radius of the plurality of channels of the first conductor hub.

Clause 26: In some examples of the modular medical lead system of clause 24, the substantially circular shape includes a radius larger than the common radius of the plurality of channels of the first conductor hub.

Clause 27: In some examples of the modular medical lead system of clause 23, the distal arrangement is shaped to couple to a separate module, wherein the separate module includes one of an electrode module, a connector module, or another elongate portion.

Clause 28: In some examples of the modular medical lead system of any of clauses 1-27, the conductor hub exhibits a substantially cylindrically shape.

Clause 29: In some examples of the modular medical lead system of any of clauses 1-28, the plurality of conductors extend out the second end of the hub body in a direction relative to the longitudinal axis of the first conductor hub.

Clause 30: In some examples of the modular medical lead system of clause 29, the direction includes two non-zero angles in two respective dimensions.

Clause 31: In some examples of the modular medical lead system of any of clauses 1-29, the conductor hub is a single piece.

Clause 32: In some examples of the modular medical lead system of any of clauses 1-30, the conductor hub is configured to transition the plurality of conductors from a proximal arrangement to a distal arrangement.

Clause 33: In some examples of the modular medical lead system of clause 32, the proximal arrangement is a coiled arrangement, and the distal arrangement is a coiled arrangement.

Clause 34: In some examples of the modular medical lead system of clause 32, the proximal arrangement is a coiled arrangement, and the distal arrangement is a straight arrangement.

Clause 35: In some examples of the modular medical lead system of clause 32, the proximal arrangement is a straight arrangement, and the distal arrangement is a straight arrangement.

Clause 36: In some examples of the modular medical lead system of any of clauses 1-35, a through-hole of the hub body is sized to fit a mandrel within the through-hole.

Clause 37: In some examples of the modular medical lead system of any of clauses 1-36, the first conductor hub is configured to couple to a drive component, and wherein the first conductor hub is configured to wind the plurality of conductors around a mandrel to manufacture the elongate portion.

Clause 38: In some examples of the modular medical lead system of clause 37, a portion of the drive component is positioned within a through-hole of the hub body, and wherein the drive component extends at least partially into the through-hole of the hub body.

Clause 39: In some examples of the modular medical lead system of clause 37, the first conductor hub is configured to fit within the drive component, wherein the drive component comprises an external drive component.

Clause 40: In some examples of the modular medical lead system of clause 2, the plurality of conductors are coiled for a length between the second end of the first conductor hub and the first end of the second conductor hub, and wherein the length is about 6 inches to 36 inches.

Clause 41: In some examples of the modular medical lead system of any of clauses 1-40, the modular medical lead system further includes the lead end module, wherein, for each conductor, the portion of the conductor that extends beyond the first end of the conductor hub is coupled to the respective electrical conductor of the lead end module to allow respective electrical signals to be conducted between the respective conductors of the lead end module and the conductors of the elongate lead body module.

Clause 42: In some examples of the modular medical lead system of any of clauses 1-41, the modular medical system is any of a medical lead, a lead extension, a screening device, a diagnostic device or a monitoring device.

Clause 43: In some examples, a medical device systems comprises the modular medical lead system of any of clauses 1-42; and a medical device, wherein the medical device is configured to at least one of deliver electrical stimulation to a patient or sense electrical signal of the patient via the plurality of conductors.

Clause 44: In some examples, a method comprises at least one of delivering electrical stimulation to a patient or sensing electrical signals of the patient via the medical device system of clause 43.

Clause 45: In some examples, a method comprises forming the modular lead system of any of clauses 1-42, wherein forming the modular lead system includes: coiling the plurality of electrical conductors; and mechanically coupling the plurality of electrical conductors to the conductor hub such that the plurality of conductors are in a fixed arrangement relative one another.

Clause 46: In some examples of the method of clause 45, the plurality of electrical conductors are mechanically coupled to the conductor hub prior to coiling the plurality of electrical conductors.

Clause 47: In some examples of the method of clause 45, the plurality of electrical conductors are mechanically coupled to the conductor hub after coiling the plurality of electrical conductors.

Clause 48: In some examples of the method of any of clauses 45-47, the method further comprises coupling, for each conductor, the portion of the conductor that extends beyond the first end of the conductor hub to a respective electrical conductor of a lead end module to allow respective electrical signals to be conducted between the respective conductors of the lead end module and the conductors of the elongate lead body module.

Clause 49: In some examples a conductor hub for a modular medical lead system comprises a hub body including a through-hole extending from a first end of the hub body to a second end of the hub body; and a plurality of channels positioned around the conductor hub, wherein respective longitudinal axes of the plurality of channels are substantially parallel to a longitudinal axis of the conductor hub, wherein the plurality of channels are positioned at a common radius from the longitudinal axis of the conductor hub.

Clause 50: In some examples of the conductor hub of clause 49, each channel defines a through-hole extending from the first end of the hub body to the second end of the hub body.

Clause 51: In some examples of the conductor hub of clause 49 or 50, each channel defines a groove on an outer surface of the hub body, each groove extending from the first end of the hub body to the second end of the hub body, wherein an outer profile of the hub body includes the grooves.

Clause 52: In some examples of the conductor hub of any of clauses 49-51, the plurality of channels includes 8 channels to 16 channels.

Clause 53: In some examples of the conductor hub of any of clauses 49-52, the conductor hub is substantially cylindrically shaped.

Clause 54: In some examples of the conductor hub of any of clauses 49-53, a radius of the through-hole of the hub body is smaller than the common radius of the plurality of channels.

Clause 55: In some examples of the conductor hub of any of clauses 49-54, the plurality of channels are circumferentially equidistant from one another.

Clause 56: In some examples of the conductor hub of any of clauses 49-55, a diameter of each channel is about 0.152 millimeters.

Clause 57: In some examples of the conductor hub of any of clauses 49-56, a diameter of a circle defined by the plurality of channels is about 0.762 millimeters.

Clause 58: In some examples of the conductor hub of any of clauses 49-57, the through-hole of the hub body is configured to fit over a mandrel used to assemble the modular medical lead system.

Clause 59: In some examples of the conductor hub of any of clauses 49-58, the conductor hub is configured to couple to a drive component, and wherein the conductor hub is configured to wind a plurality of conductors around a mandrel to manufacture the modular medical lead system.

Clause 60: In some examples of the conductor hub of clause 59, the conductor hub comprises the drive component, wherein a portion of the drive component is positioned at least partially within the through-hole of the hub body, and wherein the drive component extends at least partially into the through-hole of the hub body.

Clause 61: In some examples of the conductor hub of clause 59, the conductor hub is configured to fit within the drive component, wherein the drive component is an external drive component.

Clause 62: In some examples of the conductor hub of any of clauses 49-61, the conductor hub is configured to house a plurality of conductors within the respective channels, and wherein the conductor hub is configured to direct the plurality of conductors to extend out of the channels in a direction relative to the longitudinal axis of the conductor hub.

Clause 63: In some examples of the conductor hub of clause 62, the direction relative to the longitudinal axis of the conductor hub is parallel to the longitudinal axis of the conductor hub.

Clause 64: In some examples of the conductor hub of clause 62, the direction relative to the longitudinal axis of the conductor hub is at a non-zero angle relative to the longitudinal axis of the conductor hub.

Clause 65: In some examples of the conductor hub of clause 62, the direction relative to the longitudinal axis is angled such that the plurality of conductors form a coiled configuration Clause 66: In some examples of the conductor hub of any of clauses 49-65, the plurality of channels are substantially straight from the first end of the hub body to the second end of the hub body Clause 67: In some examples of the conductor hub of any of clauses 49-66, the through-hole of the hub body includes a portion with an increasing diameter, wherein the diameter of the through-hole increases from a medial portion of the hub body toward the second end of the hub body.

Clause 68: In some examples of the conductor hub of any of clauses 49-67, the conductor hub is configured to be placed within an outer jacket.

Clause 69: In some examples of the conductor hub of any of clauses 49-68, the first end of the hub body has a different outer diameter than the second end of the hub body.

Clause 70: In some examples, a method for forming an elongate lead body module of a modular lead comprises rotating a mandrel, wherein the mandrel extends through a through-hole of a conductor hub, wherein a plurality of conductors extend through a respective plurality of channels of the conductor hub, the conductors extending from a respective plurality of bobbins to the channels, wherein the bobbins are coupled to a carriage, the carriage defining central opening through which the mandrel passes; and moving the carriage away from the conductor hub along a length of the mandrel while the mandrel rotates causing the conductors to coil around the mandrel.

Clause 71: In some examples of the method of clause 70, the method further comprises coupling the conductor hub with the mandrel.

Clause 72: In some examples of the method of clause 70 or 71, a starting position of the carriage is adjacent to the conductor hub in a direction of a longitudinal axis of the mandrel, such that the conductors begin to coil around the mandrel adjacent to the conductor hub.

Clause 73: In some examples of the method of any of clauses 70-72, rotating the mandrel includes using a motor, wherein the mandrel is coupled to the motor, and wherein the mandrel rotates at the same rate as the motor.

Clause 74: In some examples of the method of any of clauses 70-73, the method further comprises threading the plurality of conductors within the respective plurality of channels.

Clause 75: In some examples of the method of clause 74, the threading is performed by a robotic assembly machine.

Clause 76: In some examples of the method of any of clauses 70-75, the method further comprises automating the forming of the elongate portion using processor circuitry, the processor circuitry communicatively coupled to the robotic assembly machine.

Clause 77: In some examples of the method of any of clauses 70-76, the method further comprises controlling a rate at which the bobbins dispense the conductors while moving the carriage.

Clause 78: In some examples of the method of clause 77, controlling the rate at which the bobbins dispense the conductors includes using a plurality of brakes, each bobbin coupled to a respective brake.

Clause 79: In some examples of the method of any of clauses 70-78, the method further comprises stabilizing the conductors using a stabilizer once a coiled section of the elongate portion has reached a specified length, wherein stabilizing the conductors includes fixing the conductors in respective channels of the stabilizer to maintain the coiled configuration of the coiled section.

Clause 80: In some examples of the method of any of clauses 70-79, the method further comprises stabilizing the conductors using a second conductor hub once a coiled section of the elongate portion has reached a specified length, wherein stabilizing the conductors includes coupling the conductors with respective channels of the second conductor hub, and wherein the channels of the second conductor hub are grooved channels.

Clause 81: In some examples of the method of any of clauses 70-80, the method further comprises assembling the carriage, the bobbins, and a threaded conductor hub on an assembly.

Clause 82: In some examples of the method of clause 82, the method further comprises transferring the assembly to a system including the motor for rotating the mandrel with the assembly.

Clause 83: In some examples of the method of clause 74, threading is performed by an automated assembly machine.

Clause 84: In some examples, a method for forming a modular lead comprises coiling a plurality of electrical conductors around a mandrel, wherein the mandrel is coupled to a conductor hub, wherein the conductors are mechanically coupled to the conductor hub such that the plurality of conductors are in a fixed arrangement relative to one another, wherein coiling the conductors includes coiling the conductors along a length of the mandrel, wherein the plurality of conductors extend from a respective plurality of bobbins coupled to a carriage, the carriage defining a central opening through which the mandrel extends, and wherein coiling the conductors includes moving at least one of the mandrel and the carriage relative to each other angularly and longitudinally, wherein the relative longitudinal movement occurs along a longitudinal axis of the mandrel, and wherein the relative angular movement occurs such that an orientation of the mandrel and an orientation of the carriage rotate relative to each other.

Clause 85: In some examples of the method of clause 84, moving the mandrel and the carriage relative to each other includes rotating the mandrel around the longitudinal axis of the mandrel and maintaining the orientation of the carriage, and wherein the carriage moves in a direction away from the conductor hub along the longitudinal axis of the mandrel.

Clause 86: In some examples of the method of clause 84 or 85, the method further comprises mechanically coupling the conductors to the conductor hub before coiling the conductors around the mandrel.

Clause 87: In some examples of the method of clause 86, mechanically coupling comprises mating the conductors with a respective plurality of channels extending between a first end of the conductor hub to a second end of the conductor hub.

Clause 88: In some examples of the method of clause 86, mechanically coupling the conductors to the conductor hub includes positioning the conductors into a respective plurality of through-hole channels extending between a first end of the conductor hub to a second hub of the conductor hub.

Clause 89: In some examples of the method of clause 86, mechanically coupling the conductors to the conductor hub includes robotically positioning the conductors into a respective plurality of channels extending between a first end of the conductor hub to a second hub of the conductor hub, and wherein robotically positioning the conductors includes using a robotic conductor positioning arm.

Clause 90: In some examples of the method of any of clauses 84-89, moving at least one of the mandrel and the carriage includes causing the conductors to unwind from the bobbins.

Clause 91: In some examples of the method of clause 90, unwinding the conductors from the bobbins includes controlling an angular velocity of the bobbins using a respective plurality of brakes, each bobbin coupled to a respective brake.

Clause 92: In some examples of the method of any of clauses 85-91, the method further comprises coupling the conductor hub with the mandrel before rotating the mandrel.

Clause 93: In some examples of the method of any of clauses 84-92, the method further comprises winding the conductors around the bobbins.

Clause 94: In some examples of the method of any of clauses 84-93, the bobbins are coupled to the carriage by positioning the bobbins on the carriage in a radially symmetric arrangement on the carriage.

Clause 95: In some examples of the method of any of clauses 84-94, the method further comprises positioning the carriage on a winding apparatus, wherein the winding apparatus includes the mandrel.

Clause 96: In some examples of the method of any of clauses 84-95, the carriage moves in a direction away from the conductor hub along the longitudinal axis of the mandrel, and wherein a starting position of the carriage is adjacent to the conductor hub in a direction of a longitudinal axis of the mandrel, such that the conductors begin coiling around the mandrel adjacent to the conductor hub.

Clause 97: In some examples of the method of any of clauses 85-96, rotating the mandrel includes using a motor, wherein the mandrel is coupled to the motor.

Clause 98: In some examples of the method of any of clauses 84-97, the method further comprises forming an end section of the modular lead after coiling the conductors along the length, wherein the conductor hub comprises a first conductor hub, wherein forming the end section of the modular lead includes coupling a second conductor hub to the plurality of conductors at the end section.

Clause 99: In some examples of the method of clause 98, the method further comprises coupling the conductors to a respective plurality of channels of the second conductor hub.

Clause 100: In some examples of the method of clause 99, the method further comprises coupling the conductors to the respective channels, wherein the channels are grooves, and wherein coupling the conductors to the respective channels includes mating the conductors to the respective grooves.

Clause 101: In some examples of the method of clause 100, the method further comprises capturing the conductors within a plurality of respective slots defined by a respective plurality of protrusions of the second conductor hub, wherein the grooves include the slots.

Clause 102: In some examples of the method of clause 103, the method further comprises securing the conductors to the second conductor hub by at least one of: pressing the conductors into the grooves, dispensing an adhesive to secure the conductors within the grooves, providing a pressure onto the conductors to snap-fit the conductors within the grooves, or staking the conductors using heat.

Clause 103: In some examples of the method of any of clauses 98-102, coupling the second conductor hub to the conductors includes maintaining an arrangement of the conductors using a stabilizer hub after coiling the conductors along the length.

Clause 104: In some examples of the method of clause 90, unwinding the conductors from the bobbins includes controlling a tension of the conductors using a respective plurality of brakes, each bobbin coupled to a respective break.

Clause 105: In some examples of the method of any of clauses 84-104, the method further comprises interlocking the carriage on a winder apparatus such that the mandrel, the conductor hub, and the winder apparatus are coupled to one another, wherein the winder apparatus includes the mandrel.

Clause 106: In some examples a system for assembling a modular medical lead comprises, a winder apparatus including a mandrel extending from a first section to a second section of the winder apparatus, a motor coupled to the mandrel in the first section, a carriage mount configured to couple to a carriage, wherein the mandrel extends through an opening defined by the carriage, and wherein the carriage mount is configured to move along in a direction of a longitudinal axis of the mandrel.

Clause 107: In some examples of the system of clause 106, the system further comprises an assembly apparatus including a base configured to couple to a carriage, the based configured to secure the carriage while coupling bobbins to the carriage and while coupling conductors extending from the bobbins to a conductor hub.

Clause 108: In some examples of the system of clause 107, the system further comprises a robotic arm configured to couple the conductors to the conductor hub.

Clause 109: In some examples of the system of any of clauses 106-108, the system further comprises brakes coupled to the carriage mount, the brakes coupled to respective bobbins to control an angular velocity of the bobbins.

Clause 110: In some examples of the system of clauses 107, the system further comprises an automation system configured to couple the conductors to the conductor hub.

Clause 111: In some examples of the system of any of clauses 106-110, the system further comprises brakes coupled to the carriage mount, the brakes coupled to respective bobbins to control a tension of the conductors.

Clause 112: In some examples, a modular medical system comprises an elongate body module including one or more coiled electrical conductors extending from a first end to a second end of the elongate body module, and a conductor hub adjacent the first end of the elongate body module, wherein the one or more conductors are electrically isolated from any other of the one or more conductors and mechanically coupled to the conductor hub such that the one or more conductors are in a fixed arrangement, wherein a first end of the conductor hub is nearer the first end of the elongate body module than a second end of the conductor hub, wherein each of the one or more conductors extend from the first end to the second end of the conductor hub relative a longitudinal axis of the elongate body module such that a portion of the conductors extend beyond the first end of the conductor hub, and wherein, for each conductor, the portion of the conductor that extends beyond the first end of the conductor hub is configured to be coupled to a respective electrical conductor of a lead end module to allow respective electrical signals to be conducted between the respective conductors of the lead end module and the conductors of the elongate body module.

Clause 113: In some examples of the modular medical system of clause 112, the conductor hub comprises a first conductor hub, the elongate body module further comprising a second conductor hub adjacent the second end of the elongate body, wherein the one or more conductors are electrically isolated from one another and mechanically coupled to the second conductor hub such that the one or more conductors are in a fixed arrangement relative to one another, wherein a second end of the second conductor hub is nearer the second end of the elongate body module than a first end of the second conductor hub, and wherein the one or more conductors extend from the first end to the second end of the second conductor hub relative to the longitudinal axis of the elongate body module.

Clause 114: In some examples of the modular medical system of clause 113, each of the one or more conductors extend from the first end to the second end of the second conductor hub such that a second portion of the conductors extend beyond the second end of the second conductor hub.

Clause 115: In some examples of the modular medical system of clause 114, the modular medical system further comprises another lead end module, wherein, for each conductor, the second portion of the one or more conductors that extend beyond the second end of the second conductor hub is coupled to a respective electrical conductor of the another lead end module to allow the electrical signals to be conducted between the respective electrical conductor of the another lead end module and the conductor of the elongate body module.

Clause 116: In some examples of the modular medical system of any of clauses 112-115, the conductor hub includes one or more channels extending between the first end and the second of the conductor hub, wherein, each conductor is configured to mate with a corresponding channel of the one or more channels of the conductor hub.

Clause 117: In some examples of the modular medical system of clause 116, the one or more channels comprises at least one through-hole extending from the first end of the conductor hub to the second end of the conductor hub.

Clause 118: In some examples of the modular medical system of clause 116, the one or more channels comprises at least one groove into an outer surface of the conductor hub from first end of the conductor hub to the second end of the conductor hub.

Clause 119: In some examples of the modular medical system of clause 116, the one or more channels includes 8 channels to 16 channels.

Clause 120: In some examples of the modular medical system of clause 116, a total number of channels of the conductor hub is equal to a total number of conductors of the one or more coiled electrical conductors.

Clause 121: In some examples of the modular medical system of any of clauses 112-120, the conductor hub exhibits an annular cross section along a plane substantially orthogonal to the longitudinal axis of the elongate body module.

Clause 122: In some examples of the modular medical system of clause 121, an outer diameter of the annular cross section is smaller than an outer diameter defined by the one or more channels.

Clause 123: In some examples of the modular medical system of any of clauses 112-122, the one or more conductors are arranged substantially circumferentially equidistant from one another around the conductor hub.

Clause 124: In some examples of the modular medical system of any of clauses 112-123, the one or more conductors extend from the first end to the second end of the conductor hub in a direction substantially parallel to the longitudinal axis of the elongate body module.

Clause 125: In some examples of the modular medical system of any of clauses 112-124, the portion of the one or more conductors that extend beyond the first end extend in a direction relative to the longitudinal axis of the elongate body module.

Clause 126: In some examples of the modular medical system of clause 125, the direction relative to the longitudinal axis is a non-zero angle relative to the longitudinal axis.

Clause 127: In some examples of the modular medical system of clause 125, the direction relative to the longitudinal axis is substantially parallel to the longitudinal axis.

Clause 128: In some examples of the modular medical system of any of clauses 112-127, the one or more coiled conductors in the elongate portion define an inner lumen, and wherein the conductor hub includes an aperture that is aligned substantially co-axially with the inner lumen.

Clause 129: In some examples of the modular medical system of any of clauses 112-128, each conductor comprises a single conductive filament.

Clause 130: In some examples of the modular medical system of any of clauses 112-129, at least one of the one or more conductors comprises a cable, wherein the cable includes more than one conductive filar.

Clause 131: In some examples of the modular medical system of any of clauses 112-130, the modular medical system further comprises an outer jacket covering the one or more coiled conductors and the conductor hub of the elongate body module, and wherein the jacket is comprised of an electrically non-conducting material, and wherein the jacket is biocompatible.

Clause 132: In some examples of the modular medical system of any of clauses 112-131, the first end of the conductor hub has a different outer diameter than the second end of the conductor hub.

Clause 133: In some examples of the modular medical system of any of clauses 112-132, the through-hole of the hub body includes a portion with an increasing diameter, wherein the diameter of the portion with the increasing diameter increases from a distal fiducial relative to the proximal end of the hub body toward the proximal end of the hub body.

Clause 134: In some examples of the modular medical system of any of clauses 112-133, the one or more conductors extend out the distal end of the hub body in a distal arrangement.

Clause 135: In some examples of the modular medical system of clause 134, the distal arrangement is a substantially circular shape.

Clause 136: In some examples of the modular medical system of clause 135 the substantially circular shape includes a radius smaller than the common radius of the one or more channels of the first conductor hub.

Clause 137: In some examples of the modular medical system of clause 135, the substantially circular shape includes a radius larger than the common radius of the one or more channels of the first conductor hub.

Clause 138: In some examples of the modular medical system of clause 134 the distal arrangement is shaped to couple to a separate module, wherein the separate module includes one of an electrode module, a connector module, or another elongate portion.

Clause 139: In some examples of the modular medical system of any of clauses 112-138, the conductor hub exhibits a substantially cylindrically shape.

Clause 140: In some examples of the modular medical system of any of clauses 112-139, the one or more conductors extend out the second end of the hub body in a direction relative to the longitudinal axis of the first conductor hub.

Clause 141: In some examples of the modular medical system of clause 140, the direction includes two non-zero angles in two respective dimensions.

Clause 142: In some examples of the modular medical system of any of clauses 112-141, the conductor hub is a single piece.

Clause 143: In some examples of the modular medical system of any of clauses 112-142, the conductor hub is configured to transition the one or more conductors from a proximal arrangement to a distal arrangement.

Clause 144: In some examples of the modular medical system of clause 143, the proximal arrangement is a coiled arrangement, and the distal arrangement is a coiled arrangement.

Clause 145: In some examples of the modular medical system of clause 143, the proximal arrangement is a coiled arrangement, and the distal arrangement is a straight arrangement.

Clause 146: In some examples of the modular medical system of clause 143, the proximal arrangement is a straight arrangement, and the distal arrangement is a straight arrangement.

Clause 147: In some examples of the modular medical system of any of clauses 112-146, a through-hole of the hub body is sized to fit a mandrel within the through-hole.

Clause 148: In some examples of the modular medical system of any of clauses 112-147, the first conductor hub is configured to couple to a drive component, and wherein the first conductor hub is configured to wind the one or more conductors around a mandrel to manufacture the elongate portion.

Clause 149: In some examples of the modular medical system of clause 148, a portion of the drive component is positioned within a through-hole of the hub body, and wherein the drive component extends at least partially into the through-hole of the hub body.

Clause 150: In some examples of the modular medical system of clause 148, the first conductor hub is configured to fit within the drive component, wherein the drive component comprises an external drive component.

Clause 151: In some examples of the modular medical system of clause 113, the one or more conductors are coiled for a length between the second end of the first conductor hub and the first end of the second conductor hub, and wherein the length is about 6 inches to about 36 inches.

Clause 152: In some examples of the modular medical system of any of clauses 112-152, the modular medical system further comprises the lead end module, wherein, for each conductor, the portion of the conductor that extends beyond the first end of the conductor hub is coupled to the respective electrical conductor of the lead end module to allow respective electrical signals to be conducted between the respective conductors of the lead end module and the conductors of the elongate body module.

Clause 153: In some examples of the modular medical system of any of clauses 112-152, the modular medical system is any of a medical lead, a lead extension, a screening device, a diagnostic device or a monitoring device.

Clause 154: In some examples, a medical device system comprises the modular medical lead system of any of clauses 112-153; and a medical device, wherein the medical device is configured to at least one of deliver electrical stimulation to a patient or sense electrical signal of the patient via the plurality of conductors.

Clause 155: In some examples, a method comprises at least one of delivering electrical stimulation to a patient or sensing electrical signals of the patient via the medical device system of clause 154.

Clause 156: In some examples, a method comprises forming the modular lead system of any of clauses 112-153, wherein forming the modular lead system includes: coiling the one or more electrical conductors; and mechanically coupling the one or more electrical conductors to the conductor hub such that the one or more conductors are in a fixed arrangement relative one another.

Clause 157: In some examples of the method of clause 156, the one or more electrical conductors are mechanically coupled to the conductor hub prior to coiling the plurality of electrical conductors.

Clause 158: In some examples of the method of clause 156, the one or more conductors are mechanically coupled to the conductor hub after coiling the plurality of electrical conductors.

Clause 159: In some examples of the method of clause 156, the method further comprises coupling, for each conductor, the portion of the conductor that extends beyond the first end of the conductor hub to a respective electrical conductor of a lead end module to allow respective electrical signals to be conducted between the respective conductors of the lead end module and the one or more conductors of the elongate lead body module.

These examples may be combined in any permutation or combination.

Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated.

Various aspects of the disclosure have been described. These and other aspects are within the scope of the following claims.

What is claimed is:

1. A method for forming a modular lead, the method comprising coiling a plurality of electrical conductors around a mandrel, wherein the mandrel is coupled to a conductor hub, wherein the plurality of electrical conductors are mechanically coupled to the conductor hub such that the plurality of electrical conductors are in a fixed arrangement relative to one another,
wherein coiling the plurality of electrical conductors includes coiling the plurality of electrical conductors along a length of the mandrel, wherein the plurality of electrical conductors extend from a respective plurality of bobbins coupled to a carriage, the carriage defining a central opening through which the mandrel extends, and
wherein coiling the plurality of electrical conductors includes moving the mandrel and the carriage relative to each other angularly and longitudinally, wherein the relative longitudinal movement occurs along a longitudinal axis of the mandrel, and such that the carriage moves in a direction away from the conductor hub along the longitudinal axis of the mandrel, and wherein the relative angular movement occurs such that an orientation of the mandrel and an orientation of the carriage rotate relative to each other.

2. The method of claim 1, wherein moving the mandrel and the carriage relative to each other includes rotating the mandrel around the longitudinal axis of the mandrel and maintaining the orientation of the carriage.

3. The method of claim 1, further comprising mechanically coupling the plurality of electrical conductors to the conductor hub before coiling the conductors around the mandrel.

4. The method of claim 3, wherein mechanically coupling comprises mating each conductor of the plurality of electrical conductors with a respective channel of a plurality of channels extending between a first end of the conductor hub to a second end of the conductor hub.

5. The method of claim 4, further comprising coupling the conductors to the respective channels, wherein the channels are grooves, and wherein coupling the conductors to the respective channels includes mating the conductors to the respective grooves.

6. The method of claim 1, wherein moving at least one of the mandrel and the carriage includes causing the conductors to unwind from the bobbins.

7. The method of claim 6, wherein unwinding the conductors from the bobbins includes controlling an angular velocity of the bobbins using a respective plurality of brakes, each bobbin coupled to a respective brake.

8. The method of claim 6, wherein unwinding the plurality of electrical conductors from the bobbins includes controlling a tension of the conductors using a respective plurality of brakes, each bobbin coupled to a respective break.

9. The method of claim 1, further comprising coupling the conductor hub with the mandrel before rotating the mandrel.

10. The method of claim 1, wherein the bobbins are coupled to the carriage by positioning the bobbins on the carriage in a radially symmetric arrangement on the carriage.

11. The method of claim 1, further comprising positioning the carriage on a winding apparatus, wherein the winding apparatus includes the mandrel.

12. The method of claim 1, wherein a starting position of the carriage is adjacent to the conductor hub in a direction of a longitudinal axis of the mandrel such that the plurality of electrical conductors begin coiling around the mandrel adjacent to the conductor hub.

13. The method of claim 1, further comprising forming an end section of the modular lead after coiling the conductors along the length, wherein the conductor hub comprises a first conductor hub, wherein forming the end section of the modular lead includes coupling a second conductor hub to the plurality of conductors at the end section.

14. The method of claim 13, further comprising coupling each conductor of the plurality of electrical conductors to a respective channel of a plurality of channels of the second conductor hub.

15. The method of claim 13, wherein coupling the second conductor hub to the plurality of electrical conductors includes maintaining an arrangement of the plurality of electrical conductors using a stabilizer hub after coiling the conductors along the length.

16. A method for forming a modular lead, the method comprising coiling a plurality of electrical conductors around a mandrel, wherein the mandrel is coupled to a conductor hub, wherein the plurality of electrical conductors are mechanically coupled to the conductor hub such that the plurality of electrical conductors are in a fixed arrangement relative to one another,
wherein coiling the plurality of electrical conductors includes coiling the plurality of electrical conductors along a length of the mandrel, wherein the plurality of electrical conductors extend from a respective plurality of bobbins coupled to a carriage, the carriage defining a central opening through which the mandrel extends,
wherein coiling the plurality of electrical conductors includes moving the mandrel and the carriage relative to each other angularly and longitudinally, wherein the relative longitudinal movement occurs along a longitudinal axis of the mandrel, and such that the carriage moves in a direction away from the conductor hub along the longitudinal axis of the mandrel, and wherein the relative angular movement occurs such that an orientation of the mandrel and an orientation of the carriage rotate relative to each other, and wherein a starting position of the carriage is adjacent to the conductor hub in a direction of a longitudinal axis of the mandrel such that the plurality of electrical conductors begin coiling around the mandrel adjacent to the conductor hub.

17. The method of claim 16, wherein moving the mandrel and the carriage relative to each other includes rotating the mandrel around the longitudinal axis of the mandrel.

18. The method of claim 17, further comprising coupling the conductor hub with the mandrel before rotating the mandrel.

19. The method of claim 16, further comprising mechanically coupling the plurality of electrical conductors to the conductor hub before coiling the conductors around the mandrel.

20. The method of claim 16, further comprising forming an end section of the modular lead after coiling the conductors along the length of the mandrel, wherein the conductor hub comprises a first conductor hub, and wherein forming the end section of the modular lead includes coupling a second conductor hub to the plurality of electrical conductors at the end section.

21. A method for forming a modular lead, the method comprising:

coiling a plurality of electrical conductors around a mandrel, wherein the mandrel is coupled to a first conductor hub, wherein the plurality of electrical conductors are mechanically coupled to the first conductor hub such that the plurality of electrical conductors are in a fixed arrangement relative to one another, wherein coiling the plurality of electrical conductors includes coiling the plurality of electrical conductors along a length of the mandrel, wherein the plurality of electrical conductors extend from a respective plurality of bobbins coupled to a carriage, the carriage defining a central opening through which the mandrel extends, wherein coiling the plurality of electrical conductors includes moving the mandrel and the carriage relative to each other angularly and longitudinally, wherein the relative longitudinal movement occurs along a longitudinal axis of the mandrel, and wherein the relative angular movement occurs such that an orientation of the mandrel and an orientation of the carriage rotate relative to each other; and forming an end section of the modular lead after coiling the conductors along the length, wherein forming the end section of the modular lead includes coupling a second conductor hub to the plurality of electrical conductors at the end section.

22. The method of claim 21, further comprising coupling each conductor of the plurality of electrical conductors to a respective channel of a plurality of channels of the second conductor hub.

23. The method of claim 21, wherein coupling the second conductor hub to the plurality of electrical conductors includes maintaining an arrangement of the plurality of electrical conductors using a stabilizer hub after coiling the electrical conductors along the length of the mandrel.

24. The method of claim 21, wherein moving the mandrel and the carriage relative to each other includes rotating the mandrel around the longitudinal axis of the mandrel.

25. The method of claim 21, further comprising mechanically coupling the plurality of electrical conductors to the first conductor hub before coiling the conductors around the mandrel.

26. The method of claim 21, further comprising coupling the first conductor hub with the mandrel before rotating the mandrel.

27. The method of claim 21, wherein moving the mandrel and the carriage relative to each other includes rotating the mandrel around the longitudinal axis of the mandrel and maintaining the orientation of the carriage, and moving the carriage in a direction away from the conductor hub along the longitudinal axis of the mandrel.

28. The method of claim 21, further comprising forming an end section of the modular lead after coiling the conductors along the length, wherein the conductor hub comprises a first conductor hub, wherein forming the end section of the modular lead includes coupling a second conductor hub to the plurality of conductors at the end section.

29. A method for forming a modular lead, the method comprising:

coiling a plurality of electrical conductors around a mandrel, wherein the mandrel is coupled to a conductor hub, wherein the plurality of electrical conductors are mechanically coupled to the conductor hub such that the plurality of electrical conductors are in a fixed arrangement relative to one another, wherein coiling the plurality of electrical conductors includes coiling the plurality of electrical conductors along a length of the mandrel, wherein the plurality of electrical conductors extend from a respective plurality of bobbins coupled to a carriage, the carriage defining a central opening through which the mandrel extends, and wherein coiling the plurality of electrical conductors includes moving the mandrel and the carriage relative to each other angularly and longitudinally, wherein the relative longitudinal movement occurs along a longitudinal axis of the mandrel, and wherein the relative angular movement occurs such that an orientation of the mandrel and an orientation of the carriage rotate relative to each other;

mechanically coupling the plurality of electrical conductors to the conductor hub before coiling the conductors around the mandrel, wherein mechanically coupling comprises mating each conductor of the plurality of electrical conductors with a respective channel of a plurality of channels extending between a first end of the conductor hub and a second end of the conductor hub; and wherein the channels are grooves, and wherein mating each conductor of the plurality of electrical conductors with the respective channel of the plurality of channels includes mating each conductor of the plurality of electrical conductors to the respective grooves.

* * * * *